(12) United States Patent
Noda et al.

(10) Patent No.: US 8,110,722 B2
(45) Date of Patent: Feb. 7, 2012

(54) AROMATIC ACYLTRANSFERASE GENES

(75) Inventors: Naonobu Noda, Aomori (JP); Kohei Kazuma, Aomori (JP); Takeshi Sasaki, Aomori (JP); Koichiro Kogawa, Misawa (JP); Masahiko Suzuki, Aomori (JP)

(73) Assignee: Local Independent Administrative Institution Aomori Prefectural Industrial Technology Research Center, Aomori (JP)

(*) Notice: Subject to any disclaimer, the term of this patent is extended or adjusted under 35 U.S.C. 154(b) by 339 days.

(21) Appl. No.: 12/083,581

(22) PCT Filed: Oct. 20, 2005

(86) PCT No.: PCT/JP2005/019291
§ 371 (c)(1),
(2), (4) Date: Jun. 6, 2008

(87) PCT Pub. No.: WO2007/046148
PCT Pub. Date: Apr. 26, 2007

(65) Prior Publication Data
US 2009/0288225 A1 Nov. 19, 2009

(51) Int. Cl.
 A01H 5/00 (2006.01)
 C12N 15/82 (2006.01)
 C12N 15/52 (2006.01)
 C12N 15/29 (2006.01)
 C07K 1/00 (2006.01)
 C07K 14/415 (2006.01)

(52) U.S. Cl. ........ 800/278; 800/282; 800/295; 800/298; 435/183; 435/320.1; 435/419; 536/23.2; 536/23.6; 530/370

(58) Field of Classification Search .................. None
See application file for complete search history.

(56) References Cited

U.S. PATENT DOCUMENTS

| 5,756,328 | A | 5/1998 | Steffens et al. |
| 6,723,839 | B1 * | 4/2004 | Ranu ............................ 536/23.6 |
| 7,102,056 | B1 * | 9/2006 | Lemaux et al. ............... 800/278 |
| 2004/0031072 | A1 * | 2/2004 | La Rosa et al. ............... 800/278 |
| 2005/0182570 | A1 * | 8/2005 | Geourjon et al. ............... 702/19 |

FOREIGN PATENT DOCUMENTS

| WO | WO-97/48811 A1 | 12/1997 |
| WO | WO-02/04614 A2 | 1/2002 |
| WO | WO-02/04653 A2 | 1/2002 |

OTHER PUBLICATIONS

Accession No. AAG30990, Lin et al., Nov. 2000.*
Li A. X., et al., "An acyltransferase catalyzing the formation of diacyglucose is a serine carboxypeptidase-like protein" Proceeding of the National Academy of Sciences of the United States of America, vol. 97 No. 12, Jun. 2000, pp. 6902-6907. XP-002519325.
Milkowski C., et al., "Serine carboxypeptidase-like acyltransferases" Phytochemistry, vol. 65, No. 5, Mar. 2004, pp. 517-524. XP-004492819.
Milkowski et al., "Serine carboxypeptidase-like acyltransferases," Phytochemistry, vol. 65, 2004, pp. 517-524.
Glaessgen et al., "Acylation of anthocyanins with hydroxycinnamic acids via 1-O-acylglucosides by protein preparations from cell cultures of *Daucus carota* L," Planta, vol. 186, 1992, pp. 582-585.
Fujiwara et al., "cDNA cloning, gene expression and subcellular localization of anthocyanin 5-aromatic acyltransferase from *Gentiana triflora*," The Plant Journal, vol. 16, No. 4, 1998, pp. 421-431.
Nakatsuka et al., "Temporal expression of flavonoid biosynthesis-related genes regulates flower pigmentation in gentian plants," Plant Science, vol. 168, No. 5, 2005, pp. 1309-1318.
Gong et al., "Cloning and molecular analysis of structural genes involved in anthocyanin biosynthesis and expressed in a forma-specific manner in *Perilla frutescens*," Plant Molecular Biology, vol. 35, No. 6, 1997, pp. 915-927.
Kazuma et al., "The early steps of ternatins biosynthetic pathway in the flower of *Clitoria Tematea*," Proceedings of the 2002 Spring Meeting of the Japanese Society for Horticultural Science, 2002, vol. 71, No. 2, 2002, p. 200.

* cited by examiner

*Primary Examiner* — Eileen B O Hara
(74) *Attorney, Agent, or Firm* — Birch, Stewart, Kolasch & Birch, LLP

(57) ABSTRACT

The present invention provides a protein having the amino acid sequence as shown in SEQ ID NO: 2, 4, 6, 8, 10 or 12 or a protein having a modified amino acid sequence thereof and having an activity of transferring an aromatic acyl group to a sugar residue of a flavonoid; a gene, especially cDNA, encoding the protein; and use thereof. For example, by introducing the above gene into a plant expressing hydroxycinnamate 1-O-glucosyltransferase gene, optionally together with a cDNA encoding a protein having the amino acid sequence as shown in SEQ ID NO: 14, 16 or 18 or a protein having an amino acid sequence derived therefrom by modification and having an activity of glucosylating a hydroxyl group at position 1 of hydroxycinnamic acid, and then expressing the introduced gene(s), it is possible to acylate the sugar residue of flavonoids in flowers of the plant to thereby confer a blue color on the flowers.

14 Claims, No Drawings

SEQUENCE LISTING

<160> NUMBER OF SEQ ID NOS: 78

<210> SEQ ID NO 1
<211> LENGTH: 1464
<212> TYPE: DNA
<213> ORGANISM: Clitoria ternatea cv. Double Blue

```
<220> FEATURE:
<221> NAME/KEY: CDS
<222> LOCATION: (1)..(1461)
<223> OTHER INFORMATION: Nucleotide sequence of gene coding for
      1-O-acyl-Beta-D-glucose:anthocyanin-O-acyltansferase

<400> SEQUENCE: 1 atg gca gcc ttc agt tca act cat agt gct tgt ggg att tta ctt ctt      48
Met Ala Ala Phe Ser Ser Thr His Ser Ala Cys Gly Ile Leu Leu Leu
1               5                   10                  15 ccc ctt gtt gtg tca tca ctg att tgc ttt caa ctt gca tcg tgt ggc      96
Pro Leu Val Val Ser Ser Leu Ile Cys Phe Gln Leu Ala Ser Cys Gly
                20                  25                  30 acc ata gta gag ttc ctt cct gga ttt gat gga cct ctt cct ttt gtt     144
Thr Ile Val Glu Phe Leu Pro Gly Phe Asp Gly Pro Leu Pro Phe Val
            35                  40                  45 ctt gaa act ggt tat gtt gga gtt ggt gaa gga gag gat gtg cag gtc     192
Leu Glu Thr Gly Tyr Val Gly Val Gly Glu Gly Glu Asp Val Gln Val
        50                  55                  60 ttc tac tac ttc gtt gaa tct gag aac aac cca aat gag gat cct ctc     240
Phe Tyr Tyr Phe Val Glu Ser Glu Asn Asn Pro Asn Glu Asp Pro Leu
65                  70                  75                  80 atg ctt tgg ctt act ggt ggt cct ggt tgc tct gca ttt tct ggc cta     288
Met Leu Trp Leu Thr Gly Gly Pro Gly Cys Ser Ala Phe Ser Gly Leu
                85                  90                  95 gca ctt gaa ata ggt cca ctt ata ttt aaa agg gaa gaa tat aat ggg     336
Ala Leu Glu Ile Gly Pro Leu Ile Phe Lys Arg Glu Glu Tyr Asn Gly
            100                 105                 110 ggc ttg cct aat ttg atc ttg agg cca cac tca tgg aca aag gtg agt     384
Gly Leu Pro Asn Leu Ile Leu Arg Pro His Ser Trp Thr Lys Val Ser
        115                 120                 125 agc att ata ttt gta gac ttg cct gtt tcc acc ggc ttc act tat gct     432
Ser Ile Ile Phe Val Asp Leu Pro Val Ser Thr Gly Phe Thr Tyr Ala
130                 135                 140 aga aca gat gct gca gct caa aga agt gac tgg aca tta gtt cac cat     480
Arg Thr Asp Ala Ala Ala Gln Arg Ser Asp Trp Thr Leu Val His His
145                 150                 155                 160 gcc cat gaa ttt ctt agg aag tgg ttg att gat cat cca aaa ttt ctg     528
Ala His Glu Phe Leu Arg Lys Trp Leu Ile Asp His Pro Lys Phe Leu
                165                 170                 175 caa aat gaa ctt tac att ggt ggc gat tct tac tct ggt att ccc att     576
Gln Asn Glu Leu Tyr Ile Gly Gly Asp Ser Tyr Ser Gly Ile Pro Ile
            180                 185                 190 cca gta att gtt caa gaa att tcc caa gaa aat gaa aag gga atc caa     624
Pro Val Ile Val Gln Glu Ile Ser Gln Glu Asn Glu Lys Gly Ile Gln
        195                 200                 205 cca tgg ata aat ctc cag gga tac att cta ggg aat gca ata aca aca     672
Pro Trp Ile Asn Leu Gln Gly Tyr Ile Leu Gly Asn Ala Ile Thr Thr
210                 215                 220 aga agg gaa aaa ggc tat tca ata cct ttt gca cat gga atg gca ctt     720
Arg Arg Glu Lys Gly Tyr Ser Ile Pro Phe Ala His Gly Met Ala Leu
225                 230                 235                 240 att tct gat gaa cta tat gag tca ctc cga aag aac tgt aaa gga gag     768
Ile Ser Asp Glu Leu Tyr Glu Ser Leu Arg Lys Asn Cys Lys Gly Glu
                245                 250                 255 tac cta aat gta gac ccc gaa aat gta tta tgt tct aga gat ata gac     816
Tyr Leu Asn Val Asp Pro Glu Asn Val Leu Cys Ser Arg Asp Ile Asp
            260                 265                 270 tca tac agt aag gct aca tca aga att tct ttt gcc cat att ttg gaa     864
Ser Tyr Ser Lys Ala Thr Ser Arg Ile Ser Phe Ala His Ile Leu Glu
        275                 280                 285
```

```
cga aca tgt aac tcg ggt gac att aaa aca tct ctg agg aga tct aca    912
Arg Thr Cys Asn Ser Gly Asp Ile Lys Thr Ser Leu Arg Arg Ser Thr
    290                 295                 300 ata cag aga cat cac acg aag aag ttc ctt aat act aat ctc aaa ttg    960
Ile Gln Arg His His Thr Lys Lys Phe Leu Asn Thr Asn Leu Lys Leu
305                 310                 315                 320 cca ccc tta act tgt cga act tat gca aac ttc caa tgc ggt ctt tgg   1008
Pro Pro Leu Thr Cys Arg Thr Tyr Ala Asn Phe Gln Cys Gly Leu Trp
                325                 330                 335 gcc aac gat gat aat gtt cgc agt gca cta cac att cat aag gga agt   1056
Ala Asn Asp Asp Asn Val Arg Ser Ala Leu His Ile His Lys Gly Ser
            340                 345                 350 att ggt gaa tgg cac cgg tgt agc atc cgt tta cct ttc acg tcg gac   1104
Ile Gly Glu Trp His Arg Cys Ser Ile Arg Leu Pro Phe Thr Ser Asp
        355                 360                 365 att cct aac agc ttt gag tat cat gta aat ctg agt aga aaa gga tat   1152
Ile Pro Asn Ser Phe Glu Tyr His Val Asn Leu Ser Arg Lys Gly Tyr
    370                 375                 380 tac cgt tca ttg ata tac agt ggc gat cat gac atg atg gtt cct ttc   1200
Tyr Arg Ser Leu Ile Tyr Ser Gly Asp His Asp Met Met Val Pro Phe
385                 390                 395                 400 ttg ggg act caa gca tgg ata aga tct tta aac tac tcc att gtg gat   1248
Leu Gly Thr Gln Ala Trp Ile Arg Ser Leu Asn Tyr Ser Ile Val Asp
                405                 410                 415 gat tgg agg cca tgg aat aca aat ggc caa gtt gca gga tac acg agg   1296
Asp Trp Arg Pro Trp Asn Thr Asn Gly Gln Val Ala Gly Tyr Thr Arg
            420                 425                 430 act tac tct aat cgg atg aca tat gca act atc aag ggc gga ggt cac   1344
Thr Tyr Ser Asn Arg Met Thr Tyr Ala Thr Ile Lys Gly Gly Gly His
        435                 440                 445 aca gct cca gag ttc aag cct gaa gaa tgt ttt gcc atg tac agt aga   1392
Thr Ala Pro Glu Phe Lys Pro Glu Glu Cys Phe Ala Met Tyr Ser Arg
    450                 455                 460 tgg ata tcc aaa agg cct ttg tac gag aat aac aca atg agt tca tac   1440
Trp Ile Ser Lys Arg Pro Leu Tyr Glu Asn Asn Thr Met Ser Ser Tyr
465                 470                 475                 480 acc aac ttg gca tcc att cta taa                                   1464
Thr Asn Leu Ala Ser Ile Leu
                485

<210> SEQ ID NO 2
<211> LENGTH: 487
<212> TYPE: PRT
<213> ORGANISM: Clitoria ternatea cv. Double Blue
<220> FEATURE:
<221> NAME/KEY: misc_feature
<223> OTHER INFORMATION: Amino acid sequence of 1-O-acyl-Beta-D-glucose:
      anthocyanin-O-acyltansferase

<400> SEQUENCE: 2

Met Ala Ala Phe Ser Ser Thr His Ser Ala Cys Gly Ile Leu Leu Leu
1               5                   10                  15

Pro Leu Val Val Ser Ser Leu Ile Cys Phe Gln Leu Ala Ser Cys Gly
            20                  25                  30

Thr Ile Val Glu Phe Leu Pro Gly Phe Asp Gly Pro Leu Pro Phe Val
        35                  40                  45

Leu Glu Thr Gly Tyr Val Gly Val Gly Glu Gly Glu Asp Val Gln Val
    50                  55                  60

Phe Tyr Tyr Phe Val Glu Ser Glu Asn Asn Pro Asn Glu Asp Pro Leu
65                  70                  75                  80
```

-continued

```
Met Leu Trp Leu Thr Gly Gly Pro Gly Cys Ser Ala Phe Ser Gly Leu
                85                  90                  95
Ala Leu Glu Ile Gly Pro Leu Ile Phe Lys Arg Glu Glu Tyr Asn Gly
            100                 105                 110
Gly Leu Pro Asn Leu Ile Leu Arg Pro His Ser Trp Thr Lys Val Ser
        115                 120                 125
Ser Ile Ile Phe Val Asp Leu Pro Val Ser Thr Gly Phe Thr Tyr Ala
    130                 135                 140
Arg Thr Asp Ala Ala Ala Gln Arg Ser Asp Trp Thr Leu Val His His
145                 150                 155                 160
Ala His Glu Phe Leu Arg Lys Trp Leu Ile Asp His Pro Lys Phe Leu
                165                 170                 175
Gln Asn Glu Leu Tyr Ile Gly Gly Asp Ser Tyr Ser Gly Ile Pro Ile
            180                 185                 190
Pro Val Ile Val Gln Glu Ile Ser Gln Glu Asn Glu Lys Gly Ile Gln
        195                 200                 205
Pro Trp Ile Asn Leu Gln Gly Tyr Ile Leu Gly Asn Ala Ile Thr Thr
    210                 215                 220
Arg Arg Glu Lys Gly Tyr Ser Ile Pro Phe Ala His Gly Met Ala Leu
225                 230                 235                 240
Ile Ser Asp Glu Leu Tyr Glu Ser Leu Arg Lys Asn Cys Lys Gly Glu
                245                 250                 255
Tyr Leu Asn Val Asp Pro Glu Asn Val Leu Cys Ser Arg Asp Ile Asp
            260                 265                 270
Ser Tyr Ser Lys Ala Thr Ser Arg Ile Ser Phe Ala His Ile Leu Glu
        275                 280                 285
Arg Thr Cys Asn Ser Gly Asp Ile Lys Thr Ser Leu Arg Arg Ser Thr
    290                 295                 300
Ile Gln Arg His His Thr Lys Lys Phe Leu Asn Thr Asn Leu Lys Leu
305                 310                 315                 320
Pro Pro Leu Thr Cys Arg Thr Tyr Ala Asn Phe Gln Cys Gly Leu Trp
                325                 330                 335
Ala Asn Asp Asp Asn Val Arg Ser Ala Leu His Ile His Lys Gly Ser
            340                 345                 350
Ile Gly Glu Trp His Arg Cys Ser Ile Arg Leu Pro Phe Thr Ser Asp
        355                 360                 365
Ile Pro Asn Ser Phe Glu Tyr His Val Asn Leu Ser Arg Lys Gly Tyr
    370                 375                 380
Tyr Arg Ser Leu Ile Tyr Ser Gly Asp His Asp Met Met Val Pro Phe
385                 390                 395                 400
Leu Gly Thr Gln Ala Trp Ile Arg Ser Leu Asn Tyr Ser Ile Val Asp
                405                 410                 415
Asp Trp Arg Pro Trp Asn Thr Asn Gly Gln Val Ala Gly Tyr Thr Arg
            420                 425                 430
Thr Tyr Ser Asn Arg Met Thr Tyr Ala Thr Ile Lys Gly Gly Gly His
        435                 440                 445
Thr Ala Pro Glu Phe Lys Pro Glu Glu Cys Phe Ala Met Tyr Ser Arg
    450                 455                 460
Trp Ile Ser Lys Arg Pro Leu Tyr Glu Asn Asn Thr Met Ser Ser Tyr
465                 470                 475                 480
Thr Asn Leu Ala Ser Ile Leu
                485
```

```
<210> SEQ ID NO 3
<211> LENGTH: 1410
<212> TYPE: DNA
<213> ORGANISM: Clitoria ternatea cv. Double Blue
<220> FEATURE:
<221> NAME/KEY: CDS
<222> LOCATION: (1)..(1407)
<223> OTHER INFORMATION: Nucleotide sequence of gene coding for
      1-O-acyl-Beta-D-glucose:anthocyanin-O-acyltansferase

<400> SEQUENCE: 3 atg gcg agg ttt agt tca agt ctt ggt gct cgt gtg att ttg ctt ctt      48
Met Ala Arg Phe Ser Ser Ser Leu Gly Ala Arg Val Ile Leu Leu Leu
1               5                   10                  15 ccc ctt tta ttt tca tca ctg att tcc ttt caa ctt gca tcg tgt ggc      96
Pro Leu Leu Phe Ser Ser Leu Ile Ser Phe Gln Leu Ala Ser Cys Gly
            20                  25                  30 acc aca gta gat ttc ctt cct gga ttt gat gga cct ctt cct ttt gtt     144
Thr Thr Val Asp Phe Leu Pro Gly Phe Asp Gly Pro Leu Pro Phe Val
        35                  40                  45 ctt gaa act ggt tat gtc gga gtt ggt gaa gga gag gat gtg cag gcc     192
Leu Glu Thr Gly Tyr Val Gly Val Gly Glu Gly Glu Asp Val Gln Ala
 50                  55                  60 tac tac tac ttc gtt gaa tct gag aac aac ccg aat gag gat cct ctc     240
Tyr Tyr Tyr Phe Val Glu Ser Glu Asn Asn Pro Asn Glu Asp Pro Leu
65                  70                  75                  80 atg ctt tgg ctt act ggt ggt cct ggc tgc tct tca ttt tct ggt ctc     288
Met Leu Trp Leu Thr Gly Gly Pro Gly Cys Ser Ser Phe Ser Gly Leu
                85                  90                  95 gta ctt gaa att ggt cca ctt ata ttt aaa agg gaa gaa tac aat ggg     336
Val Leu Glu Ile Gly Pro Leu Ile Phe Lys Arg Glu Glu Tyr Asn Gly
            100                 105                 110 agc ttg cct aat ttg atc ttg agg ccc cac tca tgg aca aag gtg agt     384
Ser Leu Pro Asn Leu Ile Leu Arg Pro His Ser Trp Thr Lys Val Ser
        115                 120                 125 agc att ata ttt tta gac ttg cct gtt tcc aca ggc ttc act tat gcc     432
Ser Ile Ile Phe Leu Asp Leu Pro Val Ser Thr Gly Phe Thr Tyr Ala
    130                 135                 140 agg aca gag gtt gca gct caa aaa agt gac ttg aaa tta gtt cac caa     480
Arg Thr Glu Val Ala Ala Gln Lys Ser Asp Leu Lys Leu Val His Gln
145                 150                 155                 160 gcc cat gaa ttt ctt agg aag tgg ttg att gat cat cca aaa ttt ttg     528
Ala His Glu Phe Leu Arg Lys Trp Leu Ile Asp His Pro Lys Phe Leu
                165                 170                 175 tca aat gaa gtt tac att ggt ggt gat tct tac tct ggc att act gtt     576
Ser Asn Glu Val Tyr Ile Gly Gly Asp Ser Tyr Ser Gly Ile Thr Val
            180                 185                 190 cca gca att gtt caa gaa att tca caa gga aat gaa aag ggg atc caa     624
Pro Ala Ile Val Gln Glu Ile Ser Gln Gly Asn Glu Lys Gly Ile Gln
        195                 200                 205 cct tcg ata aat ctc cag gga tac att cta ggg aat gca ttt aca aca     672
Pro Ser Ile Asn Leu Gln Gly Tyr Ile Leu Gly Asn Ala Phe Thr Thr
    210                 215                 220 aga aag gaa gaa aac tat gca ata cct ttt gca cat gga atg gca ctt     720
Arg Lys Glu Glu Asn Tyr Ala Ile Pro Phe Ala His Gly Met Ala Leu
225                 230                 235                 240 att tct gat gaa cta tac gag tca ctg caa aag aac tgt aaa ggg gag     768
Ile Ser Asp Glu Leu Tyr Glu Ser Leu Gln Lys Asn Cys Lys Gly Glu
                245                 250                 255 tac ata gac gta gac acc aaa aat gca ttg tgc tct aga gtt atg gag     816
Tyr Ile Asp Val Asp Thr Lys Asn Ala Leu Cys Ser Arg Val Met Glu
            260                 265                 270
```

| | | |
|---|---|---|
| tca tac aat gag gtt ata tca gga att tct ttt tcc cat att ttg gaa<br>Ser Tyr Asn Glu Val Ile Ser Gly Ile Ser Phe Ser His Ile Leu Glu<br>     275                    280                    285 | | 864 |
| cca aac tgt gac tgg gtc gac act gaa aca tct tta agg aga tct tta<br>Pro Asn Cys Asp Trp Val Asp Thr Glu Thr Ser Leu Arg Arg Ser Leu<br>     290                    295                    300 | | 912 |
| att cag aga cat cac ggg aaa aag ttc ctc aat act aga ttg cca gcc<br>Ile Gln Arg His His Gly Lys Lys Phe Leu Asn Thr Arg Leu Pro Ala<br>305                    310                    315                    320 | | 960 |
| tta agc tgt cga act tac gca aac ttc caa tcc agt ttt tgg gct aac<br>Leu Ser Cys Arg Thr Tyr Ala Asn Phe Gln Ser Ser Phe Trp Ala Asn<br>                  325                    330                    335 | | 1008 |
| gat gat aat gtt cgt agt gca cta cac att cgt aag gga agt att ggt<br>Asp Asp Asn Val Arg Ser Ala Leu His Ile Arg Lys Gly Ser Ile Gly<br>                  340                    345                    350 | | 1056 |
| aaa tgg cgt cga tgt acc cgt aat tta cct tac acg gaa gat atc cct<br>Lys Trp Arg Arg Cys Thr Arg Asn Leu Pro Tyr Thr Glu Asp Ile Pro<br>     355                    360                    365 | | 1104 |
| tct agc ttt gag tat cat gta aac ctc agt gga aaa ggc tat tat cgt<br>Ser Ser Phe Glu Tyr His Val Asn Leu Ser Gly Lys Gly Tyr Tyr Arg<br>370                    375                    380 | | 1152 |
| tcg ttg gta tac agt ggc gat cat gac ttg atg gtt cct ttc ttg ggg<br>Ser Leu Val Tyr Ser Gly Asp His Asp Leu Met Val Pro Phe Leu Gly<br>385                    390                    395                    400 | | 1200 |
| act caa gca tgg att aga tct ctg aac tat tcc att gtg gat gat tgg<br>Thr Gln Ala Trp Ile Arg Ser Leu Asn Tyr Ser Ile Val Asp Asp Trp<br>                  405                    410                    415 | | 1248 |
| agg caa tgg aat aca aat ggc caa gtt gca gga tac aca agg act tac<br>Arg Gln Trp Asn Thr Asn Gly Gln Val Ala Gly Tyr Thr Arg Thr Tyr<br>                  420                    425                    430 | | 1296 |
| tct aat cgg atg aca ttt gca act gtg aag ggt gga ggt cac aca gct<br>Ser Asn Arg Met Thr Phe Ala Thr Val Lys Gly Gly Gly His Thr Ala<br>     435                    440                    445 | | 1344 |
| ccg gag ttc aaa cct gaa gaa tgt ttt gcc atg tac agt aga tgg ata<br>Pro Glu Phe Lys Pro Glu Glu Cys Phe Ala Met Tyr Ser Arg Trp Ile<br>450                    455                    460 | | 1392 |
| tct aaa agg cct ttg taa<br>Ser Lys Arg Pro Leu<br>465 | | 1410 |

<210> SEQ ID NO 4
<211> LENGTH: 469
<212> TYPE: PRT
<213> ORGANISM: Clitoria ternatea cv. Double Blue
<220> FEATURE:
<221> NAME/KEY: misc_feature
<223> OTHER INFORMATION: Amino acid sequence of 1-O-acyl-Beta-D-glucose:
     anthocyanin-O-acyltansferase

<400> SEQUENCE: 4

Met Ala Arg Phe Ser Ser Leu Gly Ala Arg Val Ile Leu Leu Leu
1                5                    10                    15

Pro Leu Leu Phe Ser Ser Leu Ile Ser Phe Gln Leu Ala Ser Cys Gly
                20                    25                    30

Thr Thr Val Asp Phe Leu Pro Gly Phe Asp Gly Pro Leu Pro Phe Val
                35                    40                    45

Leu Glu Thr Gly Tyr Val Gly Val Gly Glu Gly Glu Asp Val Gln Ala
     50                    55                    60

Tyr Tyr Tyr Phe Val Glu Ser Glu Asn Asn Pro Asn Glu Asp Pro Leu
65                    70                    75                    80

-continued

```
Met Leu Trp Leu Thr Gly Gly Pro Gly Cys Ser Ser Phe Ser Gly Leu
                85                  90                  95

Val Leu Glu Ile Gly Pro Leu Ile Phe Lys Arg Glu Glu Tyr Asn Gly
            100                 105                 110

Ser Leu Pro Asn Leu Ile Leu Arg Pro His Ser Trp Thr Lys Val Ser
        115                 120                 125

Ser Ile Ile Phe Leu Asp Leu Pro Val Ser Thr Gly Phe Thr Tyr Ala
    130                 135                 140

Arg Thr Glu Val Ala Ala Gln Lys Ser Asp Leu Lys Leu Val His Gln
145                 150                 155                 160

Ala His Glu Phe Leu Arg Lys Trp Leu Ile Asp His Pro Lys Phe Leu
                165                 170                 175

Ser Asn Glu Val Tyr Ile Gly Gly Asp Ser Tyr Ser Gly Ile Thr Val
            180                 185                 190

Pro Ala Ile Val Gln Glu Ile Ser Gln Gly Asn Glu Lys Gly Ile Gln
        195                 200                 205

Pro Ser Ile Asn Leu Gln Gly Tyr Ile Leu Gly Asn Ala Phe Thr Thr
    210                 215                 220

Arg Lys Glu Glu Asn Tyr Ala Ile Pro Phe Ala His Gly Met Ala Leu
225                 230                 235                 240

Ile Ser Asp Glu Leu Tyr Glu Ser Leu Gln Lys Asn Cys Lys Gly Glu
                245                 250                 255

Tyr Ile Asp Val Asp Thr Lys Asn Ala Leu Cys Ser Arg Val Met Glu
            260                 265                 270

Ser Tyr Asn Glu Val Ile Ser Gly Ile Ser Phe Ser His Ile Leu Glu
        275                 280                 285

Pro Asn Cys Asp Trp Val Asp Thr Glu Thr Ser Leu Arg Arg Ser Leu
    290                 295                 300

Ile Gln Arg His His Gly Lys Lys Phe Leu Asn Thr Arg Leu Pro Ala
305                 310                 315                 320

Leu Ser Cys Arg Thr Tyr Ala Asn Phe Gln Ser Ser Phe Trp Ala Asn
                325                 330                 335

Asp Asp Asn Val Arg Ser Ala Leu His Ile Arg Lys Gly Ser Ile Gly
            340                 345                 350

Lys Trp Arg Arg Cys Thr Arg Asn Leu Pro Tyr Thr Glu Asp Ile Pro
        355                 360                 365

Ser Ser Phe Glu Tyr His Val Asn Leu Ser Lys Gly Tyr Tyr Arg
    370                 375                 380

Ser Leu Val Tyr Ser Gly Asp His Asp Leu Met Val Pro Phe Leu Gly
385                 390                 395                 400

Thr Gln Ala Trp Ile Arg Ser Leu Asn Tyr Ser Ile Val Asp Asp Trp
                405                 410                 415

Arg Gln Trp Asn Thr Asn Gly Gln Val Ala Gly Tyr Thr Arg Thr Tyr
            420                 425                 430

Ser Asn Arg Met Thr Phe Ala Thr Val Lys Gly Gly His Thr Ala
        435                 440                 445

Pro Glu Phe Lys Pro Glu Glu Cys Phe Ala Met Tyr Ser Arg Trp Ile
    450                 455                 460

Ser Lys Arg Pro Leu
465
```

<210> SEQ ID NO 5
<211> LENGTH: 1473
<212> TYPE: DNA
<213> ORGANISM: Gentiana triflora cv. Hakkoda

```
<220> FEATURE:
<221> NAME/KEY: CDS
<222> LOCATION: (1)..(1470)
<223> OTHER INFORMATION: Nucleotide sequence of gene coding for
      1-O-acyl-Beta-D-glucose:anthocyanin-O-acyltansferase

<400> SEQUENCE: 5 atg gcg gtg ccg gcg gtg ccg gcg gtg ccg gcg gtg ccg gcg gtg ccc    48
Met Ala Val Pro Ala Val Pro Ala Val Pro Ala Val Pro Ala Val Pro
1               5                   10                  15 tcc gaa ggt cat gaa gaa caa cat aag tca aca agc agc ttt gga ata    96
Ser Glu Gly His Glu Glu Gln His Lys Ser Thr Ser Ser Phe Gly Ile
            20                  25                  30 gga agc att aag ttt cag tgc tct ttg ttt gct gtt cta ctt ttt gca   144
Gly Ser Ile Lys Phe Gln Cys Ser Leu Phe Ala Val Leu Leu Phe Ala
        35                  40                  45 ctt tta tac agc tca tca tcc cag tcc att gtc aaa act tta ccg gga   192
Leu Leu Tyr Ser Ser Ser Ser Gln Ser Ile Val Lys Thr Leu Pro Gly
    50                  55                  60 ttt cat gga tct cta ccc ttc aca ctt gag agt ggc tat gtt ggt gtc   240
Phe His Gly Ser Leu Pro Phe Thr Leu Glu Ser Gly Tyr Val Gly Val
65                  70                  75                  80 gga gag aat gaa gag ttg cag tta ttc tac tat ttc att gag tcg gag   288
Gly Glu Asn Glu Glu Leu Gln Leu Phe Tyr Tyr Phe Ile Glu Ser Glu
                85                  90                  95 aga gat ccg gcg aat gac cct ctc gtc att tgg ctc acc ggt ggc cct   336
Arg Asp Pro Ala Asn Asp Pro Leu Val Ile Trp Leu Thr Gly Gly Pro
            100                 105                 110 ggc tgt tct gcc ttc tcc ggt ctt att ttc gag ata ggt cca ttg acc   384
Gly Cys Ser Ala Phe Ser Gly Leu Ile Phe Glu Ile Gly Pro Leu Thr
        115                 120                 125 ttt gat ttt gag agt tac caa ggg ggc gta cct acc ttg aat tac aac   432
Phe Asp Phe Glu Ser Tyr Gln Gly Gly Val Pro Thr Leu Asn Tyr Asn
130                 135                 140 cca cac tcc tgg aca aag gaa gct agc att ata ttt gta gat tca ccg   480
Pro His Ser Trp Thr Lys Glu Ala Ser Ile Ile Phe Val Asp Ser Pro
145                 150                 155                 160 gtg ggt acc gga tat tcc tat tca aat aca ttt gaa ggt tac cat tcc   528
Val Gly Thr Gly Tyr Ser Tyr Ser Asn Thr Phe Glu Gly Tyr His Ser
                165                 170                 175 act gat cac aaa gca tca gac gat ctc tat gca ttt ctc cga aag tgg   576
Thr Asp His Lys Ala Ser Asp Asp Leu Tyr Ala Phe Leu Arg Lys Trp
            180                 185                 190 ctg ctg aaa cat ccc aag ttt ctt aaa aat cca gtt tat gtt gga ggt   624
Leu Leu Lys His Pro Lys Phe Leu Lys Asn Pro Val Tyr Val Gly Gly
        195                 200                 205 gac tca tat ggc gga aag ttc gtt gca ctt gtc acc tgg aga ata tct   672
Asp Ser Tyr Gly Gly Lys Phe Val Ala Leu Val Thr Trp Arg Ile Ser
210                 215                 220 caa ggt att gat gct ggt cat gag cca aga att aat ctt cag gga tac   720
Gln Gly Ile Asp Ala Gly His Glu Pro Arg Ile Asn Leu Gln Gly Tyr
225                 230                 235                 240 att gta ggg aat cct gtg gct gat ggc ttc att gat gga aat gcg ccc   768
Ile Val Gly Asn Pro Val Ala Asp Gly Phe Ile Asp Gly Asn Ala Pro
                245                 250                 255 cta ccg ttt gct cat cgt atg ggt cta ata tca gat gac atc cac aag   816
Leu Pro Phe Ala His Arg Met Gly Leu Ile Ser Asp Asp Ile His Lys
            260                 265                 270 atg gcg gaa gaa aac tgt aat ggg aac tat ata aag gcg gat caa agc   864
Met Ala Glu Glu Asn Cys Asn Gly Asn Tyr Ile Lys Ala Asp Gln Ser
        275                 280                 285
```

```
aac ggt tta tgc ctt gaa gcc atc aag cag tac gaa gag tgc act gct    912
Asn Gly Leu Cys Leu Glu Ala Ile Lys Gln Tyr Glu Glu Cys Thr Ala
    290             295                 300 gat ata tgc ttt gat aac att ttg gaa ccc aat tgc caa gag aaa atg    960
Asp Ile Cys Phe Asp Asn Ile Leu Glu Pro Asn Cys Gln Glu Lys Met
305             310                 315                 320 aca tct cat gac atc tcc ctt cta aaa ctt cca tca gag cta aag gaa   1008
Thr Ser His Asp Ile Ser Leu Leu Lys Leu Pro Ser Glu Leu Lys Glu
                325                 330                 335 gag cca tgg tgc cga aaa gat tca tac ttt ctg act cat gtt tgg gca   1056
Glu Pro Trp Cys Arg Lys Asp Ser Tyr Phe Leu Thr His Val Trp Ala
            340                 345                 350 aat gat cca tcc gtc cag aag gct ctt cat atc cga gaa gga aca att   1104
Asn Asp Pro Ser Val Gln Lys Ala Leu His Ile Arg Glu Gly Thr Ile
        355                 360                 365 aaa gag tgg gtg aga tgc aat tat agt ata tca tac agc gag aag cta   1152
Lys Glu Trp Val Arg Cys Asn Tyr Ser Ile Ser Tyr Ser Glu Lys Leu
    370                 375                 380 gat aca gtt ctt gag tat cat cac ctt cta agt aag cgt gga tac aaa   1200
Asp Thr Val Leu Glu Tyr His His Leu Leu Ser Lys Arg Gly Tyr Lys
385             390                 395                 400 aca ttg gca tac agt ggc gac cat gat ctg tat att ccg tac aca gca   1248
Thr Leu Ala Tyr Ser Gly Asp His Asp Leu Tyr Ile Pro Tyr Thr Ala
                405                 410                 415 aca cta gaa tgg att cac aca ctc aat cta cct gtt gct gat gag tgg   1296
Thr Leu Glu Trp Ile His Thr Leu Asn Leu Pro Val Ala Asp Glu Trp
            420                 425                 430 cgt cca tgg aaa gtt gat aat caa gtt gct gga tat act aaa agg ttt   1344
Arg Pro Trp Lys Val Asp Asn Gln Val Ala Gly Tyr Thr Lys Arg Phe
        435                 440                 445 att cac aat gaa act gga aaa tat gtg aca ttt gca act gtg aag gct   1392
Ile His Asn Glu Thr Gly Lys Tyr Val Thr Phe Ala Thr Val Lys Ala
    450                 455                 460 gca ggc cat aca gca cct gag tat aag cgt aga gaa tgc tta gct atg   1440
Ala Gly His Thr Ala Pro Glu Tyr Lys Arg Arg Glu Cys Leu Ala Met
465             470                 475                 480 gtt gcc cgg ttt ttc tcg gat tct cca ttg taa                       1473
Val Ala Arg Phe Phe Ser Asp Ser Pro Leu
                485                 490
```

<210> SEQ ID NO 6
<211> LENGTH: 490
<212> TYPE: PRT
<213> ORGANISM: Gentiana triflora cv. Hakkoda
<220> FEATURE:
<221> NAME/KEY: misc_feature
<223> OTHER INFORMATION: Amino acid sequence of 1-O-acyl-Beta-D-glucose:
    anthocyanin-O-acyltansferase

<400> SEQUENCE: 6

```
Met Ala Val Pro Ala Val Pro Ala Val Pro Ala Val Pro Ala Val Pro
1               5                   10                  15

Ser Glu Gly His Glu Glu Gln His Lys Ser Thr Ser Ser Phe Gly Ile
                20                  25                  30

Gly Ser Ile Lys Phe Gln Cys Ser Leu Phe Ala Val Leu Leu Phe Ala
            35                  40                  45

Leu Leu Tyr Ser Ser Ser Ser Gln Ser Ile Val Lys Thr Leu Pro Gly
        50                  55                  60

Phe His Gly Ser Leu Pro Phe Thr Leu Glu Ser Gly Tyr Val Gly Val
65                  70                  75                  80
```

```
Gly Glu Asn Glu Glu Leu Gln Leu Phe Tyr Tyr Phe Ile Glu Ser Glu
                85                  90                  95

Arg Asp Pro Ala Asn Asp Pro Leu Val Ile Trp Leu Thr Gly Gly Pro
            100                 105                 110

Gly Cys Ser Ala Phe Ser Gly Leu Ile Phe Glu Ile Gly Pro Leu Thr
        115                 120                 125

Phe Asp Phe Glu Ser Tyr Gln Gly Gly Val Pro Thr Leu Asn Tyr Asn
    130                 135                 140

Pro His Ser Trp Thr Lys Glu Ala Ser Ile Ile Phe Val Asp Ser Pro
145                 150                 155                 160

Val Gly Thr Gly Tyr Ser Tyr Ser Asn Thr Phe Glu Gly Tyr His Ser
                165                 170                 175

Thr Asp His Lys Ala Ser Asp Asp Leu Tyr Ala Phe Leu Arg Lys Trp
            180                 185                 190

Leu Leu Lys His Pro Lys Phe Leu Lys Asn Pro Val Tyr Val Gly Gly
        195                 200                 205

Asp Ser Tyr Gly Gly Lys Phe Val Ala Leu Val Thr Trp Arg Ile Ser
    210                 215                 220

Gln Gly Ile Asp Ala Gly His Glu Pro Arg Ile Asn Leu Gln Gly Tyr
225                 230                 235                 240

Ile Val Gly Asn Pro Val Ala Asp Gly Phe Ile Asp Gly Asn Ala Pro
                245                 250                 255

Leu Pro Phe Ala His Arg Met Gly Leu Ile Ser Asp Asp Ile His Lys
            260                 265                 270

Met Ala Glu Glu Asn Cys Asn Gly Asn Tyr Ile Lys Ala Asp Gln Ser
        275                 280                 285

Asn Gly Leu Cys Leu Glu Ala Ile Lys Gln Tyr Glu Glu Cys Thr Ala
    290                 295                 300

Asp Ile Cys Phe Asp Asn Ile Leu Glu Pro Asn Cys Gln Glu Lys Met
305                 310                 315                 320

Thr Ser His Asp Ile Ser Leu Leu Lys Leu Pro Ser Glu Leu Lys Glu
                325                 330                 335

Glu Pro Trp Cys Arg Lys Asp Ser Tyr Phe Leu Thr His Val Trp Ala
            340                 345                 350

Asn Asp Pro Ser Val Gln Lys Ala Leu His Ile Arg Glu Gly Thr Ile
        355                 360                 365

Lys Glu Trp Val Arg Cys Asn Tyr Ser Ile Ser Tyr Ser Glu Lys Leu
    370                 375                 380

Asp Thr Val Leu Glu Tyr His His Leu Leu Ser Lys Arg Gly Tyr Lys
385                 390                 395                 400

Thr Leu Ala Tyr Ser Gly Asp His Asp Leu Tyr Ile Pro Tyr Thr Ala
                405                 410                 415

Thr Leu Glu Trp Ile His Thr Leu Asn Leu Pro Val Ala Asp Glu Trp
            420                 425                 430

Arg Pro Trp Lys Val Asp Asn Gln Val Ala Gly Tyr Thr Lys Arg Phe
        435                 440                 445

Ile His Asn Glu Thr Gly Lys Tyr Val Thr Phe Ala Thr Val Lys Ala
    450                 455                 460

Ala Gly His Thr Ala Pro Glu Tyr Lys Arg Arg Glu Cys Leu Ala Met
465                 470                 475                 480

Val Ala Arg Phe Phe Ser Asp Ser Pro Leu
                485                 490
```

<210> SEQ ID NO 7
<211> LENGTH: 1485
<212> TYPE: DNA
<213> ORGANISM: Gentiana triflora cv. Hakkoda
<220> FEATURE:
<221> NAME/KEY: CDS
<222> LOCATION: (1)..(1482)
<223> OTHER INFORMATION: Nucleotide sequence of gene coding for
    1-O-acyl-Beta-D-glucose:anthocyanin-O-acyltansferase

<400> SEQUENCE: 7

```
atg gcg gat aca aac ggc aca gcc aag acg acg agc agg gta aaa tgg        48
Met Ala Asp Thr Asn Gly Thr Ala Lys Thr Thr Ser Arg Val Lys Trp
1               5                   10                  15 tac tta tac ctc tac tgc aac gtc att acg ggg ctg ctt tat ctt caa        96
Tyr Leu Tyr Leu Tyr Cys Asn Val Ile Thr Gly Leu Leu Tyr Leu Gln
            20                  25                  30 cat tct ctt cta caa gta gag gct gct gat tca aca aca gtg aag ttt       144
His Ser Leu Leu Gln Val Glu Ala Ala Asp Ser Thr Thr Val Lys Phe
        35                  40                  45 ctc cct ggt ttt aaa ggc ccc ctt cct ttc gaa ctc gaa acc ggg tat       192
Leu Pro Gly Phe Lys Gly Pro Leu Pro Phe Glu Leu Glu Thr Gly Tyr
    50                  55                  60 att ggg gtg gat aaa gga gaa aat gtg cag ctt ttt tac tat ttt gta       240
Ile Gly Val Asp Lys Gly Glu Asn Val Gln Leu Phe Tyr Tyr Phe Val
65                  70                  75                  80 aag tca tat tct gat tat caa att gat cct ctt gtg cta tgg atg act       288
Lys Ser Tyr Ser Asp Tyr Gln Ile Asp Pro Leu Val Leu Trp Met Thr
                85                  90                  95 gga ggt cct ggt tgt tct gct tta aca gca ttt gcc tat gag ata ggg       336
Gly Gly Pro Gly Cys Ser Ala Leu Thr Ala Phe Ala Tyr Glu Ile Gly
            100                 105                 110 cca ata gct ttt gag gaa gtc ttc tcc aat ggc gac gtt cca cga tta       384
Pro Ile Ala Phe Glu Glu Val Phe Ser Asn Gly Asp Val Pro Arg Leu
        115                 120                 125 gtg atg aac cct tat tca tgg aca cag gaa gca agc ata gtt ttc gtt       432
Val Met Asn Pro Tyr Ser Trp Thr Gln Glu Ala Ser Ile Val Phe Val
    130                 135                 140 gat gcc ccg gtt ggc acc gga ttt tcg tat ccg aga tct sca gaa gca       480
Asp Ala Pro Val Gly Thr Gly Phe Ser Tyr Pro Arg Ser Xaa Glu Ala
145                 150                 155                 160 ttt aga tct act ggg ttg caa aca tgt aat caa att tat cag ttt ctc       528
Phe Arg Ser Thr Gly Leu Gln Thr Cys Asn Gln Ile Tyr Gln Phe Leu
                165                 170                 175 aaa aag ttt tta gtc cat cac ccg gaa ttc cta tcc aat ccg tta tat       576
Lys Lys Phe Leu Val His His Pro Glu Phe Leu Ser Asn Pro Leu Tyr
            180                 185                 190 gtc ggc ggc gat tcg tac gcg ggc ctt ttc gtt ccc gtt gta gct gaa       624
Val Gly Gly Asp Ser Tyr Ala Gly Leu Phe Val Pro Val Val Ala Glu
        195                 200                 205 ttg ata gct cat gga aat gaa aac ggg atc gaa cca tcg att aat ctt       672
Leu Ile Ala His Gly Asn Glu Asn Gly Ile Glu Pro Ser Ile Asn Leu
    210                 215                 220 aag ata ttt cct tct gaa tgc ttt ttc gat ctg gga tat gtt ctt ggt       720
Lys Ile Phe Pro Ser Glu Cys Phe Phe Asp Leu Gly Tyr Val Leu Gly
225                 230                 235                 240 aac cct ctt aca acc cca tat gat gta gat tat cga gtg ccc ttt tct       768
Asn Pro Leu Thr Thr Pro Tyr Asp Val Asp Tyr Arg Val Pro Phe Ser
                245                 250                 255 cat gga atg ggt att atc tct gat gag ctt tat gag tcc ttg aag ttg       816
His Gly Met Gly Ile Ile Ser Asp Glu Leu Tyr Glu Ser Leu Lys Leu
            260                 265                 270
```

```
aac tgc aat ggt gtg tac cat gat gta gat cct act aac aca aag tgt      864
Asn Cys Asn Gly Val Tyr His Asp Val Asp Pro Thr Asn Thr Lys Cys
        275                 280                 285 ttg aat gat ata gac act ttc aaa cag gtg ttt cac ggc att cga cgt      912
Leu Asn Asp Ile Asp Thr Phe Lys Gln Val Phe His Gly Ile Arg Arg
    290                 295                 300 tca cat ata ctg gag ccc tat tgt gta tcg gta cta cca gaa caa cag      960
Ser His Ile Leu Glu Pro Tyr Cys Val Ser Val Leu Pro Glu Gln Gln
305                 310                 315                 320 atg ctt agt acc gaa aga cag cgt tct ctc cat gaa aac aac ctc cgg     1008
Met Leu Ser Thr Glu Arg Gln Arg Ser Leu His Glu Asn Asn Leu Arg
                325                 330                 335 att cct gac gtg ctt aac atg cat cat aca ttt aga tgc cgt act gat     1056
Ile Pro Asp Val Leu Asn Met His His Thr Phe Arg Cys Arg Thr Asp
    340                 345                 350 gga tac ata cct gct tat tac tgg gct aac gat gat cgt gtc cgc gag     1104
Gly Tyr Ile Pro Ala Tyr Tyr Trp Ala Asn Asp Asp Arg Val Arg Glu
355                 360                 365 gcc ctc cat att cat aag gga agc atc aag aac tgg gta cgt tgt aac     1152
Ala Leu His Ile His Lys Gly Ser Ile Lys Asn Trp Val Arg Cys Asn
        370                 375                 380 cgt tcg ttg cca ttc gaa gat tcg ata aga aac gtt gta cct tat cat     1200
Arg Ser Leu Pro Phe Glu Asp Ser Ile Arg Asn Val Val Pro Tyr His
385                 390                 395                 400 gca aac ctc agc aaa aaa gga tat aga tca ctt ata tac agc gga gat     1248
Ala Asn Leu Ser Lys Lys Gly Tyr Arg Ser Leu Ile Tyr Ser Gly Asp
                405                 410                 415 cat gac gcg atg gtg cca ttc atg gct act caa gca tgg ata aga tca     1296
His Asp Ala Met Val Pro Phe Met Ala Thr Gln Ala Trp Ile Arg Ser
    420                 425                 430 tta aac tac tcc att gtt gat gaa tgg cgc caa tgg att gtt gaa ggc     1344
Leu Asn Tyr Ser Ile Val Asp Glu Trp Arg Gln Trp Ile Val Glu Gly
435                 440                 445 caa gtt gct gga tat aca aga aca tat gct aac cag atg aca ttt gct     1392
Gln Val Ala Gly Tyr Thr Arg Thr Tyr Ala Asn Gln Met Thr Phe Ala
        450                 455                 460 aca gta aag gga ggt ggg cat act gct cct gaa tat aag cca aaa gaa     1440
Thr Val Lys Gly Gly Gly His Thr Ala Pro Glu Tyr Lys Pro Lys Glu
465                 470                 475                 480 tgc aaa gca atg ttt aaa agg tgg ata act cat aaa ccg ttg tag         1485
Cys Lys Ala Met Phe Lys Arg Trp Ile Thr His Lys Pro Leu
                485                 490
```

<210> SEQ ID NO 8
<211> LENGTH: 494
<212> TYPE: PRT
<213> ORGANISM: Gentiana triflora cv. Hakkoda
<220> FEATURE:
<221> NAME/KEY: misc_feature
<223> OTHER INFORMATION: Amino acid sequence of 1-O-acyl-Beta-D-glucose:
      anthocyanin-O-acyltansferase
<220> FEATURE:
<221> NAME/KEY: misc_feature
<222> LOCATION: (158)..(158)
<223> OTHER INFORMATION: The 'Xaa' at location 158 stands for Ala, or
      Pro.

<400> SEQUENCE: 8

```
Met Ala Asp Thr Asn Gly Thr Ala Lys Thr Thr Ser Arg Val Lys Trp
1               5                   10                  15

Tyr Leu Tyr Leu Tyr Cys Asn Val Ile Thr Gly Leu Leu Tyr Leu Gln
            20                  25                  30
```

```
His Ser Leu Leu Gln Val Glu Ala Ala Asp Ser Thr Thr Val Lys Phe
             35                  40                  45

Leu Pro Gly Phe Lys Gly Pro Leu Pro Phe Glu Leu Glu Thr Gly Tyr
 50                  55                  60

Ile Gly Val Asp Lys Gly Glu Asn Val Gln Leu Phe Tyr Tyr Phe Val
 65                  70                  75                  80

Lys Ser Tyr Ser Asp Tyr Gln Ile Asp Pro Leu Val Leu Trp Met Thr
                 85                  90                  95

Gly Gly Pro Gly Cys Ser Ala Leu Thr Ala Phe Ala Tyr Glu Ile Gly
            100                 105                 110

Pro Ile Ala Phe Glu Glu Val Phe Ser Asn Gly Asp Val Pro Arg Leu
        115                 120                 125

Val Met Asn Pro Tyr Ser Trp Thr Gln Glu Ala Ser Ile Val Phe Val
    130                 135                 140

Asp Ala Pro Val Gly Thr Gly Phe Ser Tyr Pro Arg Ser Xaa Glu Ala
145                 150                 155                 160

Phe Arg Ser Thr Gly Leu Gln Thr Cys Asn Gln Ile Tyr Gln Phe Leu
                165                 170                 175

Lys Lys Phe Leu Val His His Pro Glu Phe Leu Ser Asn Pro Leu Tyr
            180                 185                 190

Val Gly Gly Asp Ser Tyr Ala Gly Leu Phe Val Pro Val Val Ala Glu
        195                 200                 205

Leu Ile Ala His Gly Asn Glu Asn Gly Ile Glu Pro Ser Ile Asn Leu
    210                 215                 220

Lys Ile Phe Pro Ser Glu Cys Phe Phe Asp Leu Gly Tyr Val Leu Gly
225                 230                 235                 240

Asn Pro Leu Thr Thr Pro Tyr Asp Val Asp Tyr Arg Val Pro Phe Ser
                245                 250                 255

His Gly Met Gly Ile Ile Ser Asp Glu Leu Tyr Glu Ser Leu Lys Leu
            260                 265                 270

Asn Cys Asn Gly Val Tyr His Asp Val Asp Pro Thr Asn Thr Lys Cys
        275                 280                 285

Leu Asn Asp Ile Asp Thr Phe Lys Gln Val Phe His Gly Ile Arg Arg
    290                 295                 300

Ser His Ile Leu Glu Pro Tyr Cys Val Ser Val Leu Pro Glu Gln Gln
305                 310                 315                 320

Met Leu Ser Thr Glu Arg Gln Arg Ser Leu His Glu Asn Asn Leu Arg
                325                 330                 335

Ile Pro Asp Val Leu Asn Met His His Thr Phe Arg Cys Arg Thr Asp
            340                 345                 350

Gly Tyr Ile Pro Ala Tyr Tyr Trp Ala Asn Asp Asp Arg Val Arg Glu
        355                 360                 365

Ala Leu His Ile His Lys Gly Ser Ile Lys Asn Trp Val Arg Cys Asn
    370                 375                 380

Arg Ser Leu Pro Phe Glu Asp Ser Ile Arg Asn Val Val Pro Tyr His
385                 390                 395                 400

Ala Asn Leu Ser Lys Lys Gly Tyr Arg Ser Leu Ile Tyr Ser Gly Asp
                405                 410                 415

His Asp Ala Met Val Pro Phe Met Ala Thr Gln Ala Trp Ile Arg Ser
            420                 425                 430

Leu Asn Tyr Ser Ile Val Asp Glu Trp Arg Gln Trp Ile Val Glu Gly
        435                 440                 445

Gln Val Ala Gly Tyr Thr Arg Thr Tyr Ala Asn Gln Met Thr Phe Ala
    450                 455                 460
```

```
Thr Val Lys Gly Gly Gly His Thr Ala Pro Glu Tyr Lys Pro Lys Glu
465                 470                 475                 480

Cys Lys Ala Met Phe Lys Arg Trp Ile Thr His Lys Pro Leu
                485                 490

<210> SEQ ID NO 9
<211> LENGTH: 1455
<212> TYPE: DNA
<213> ORGANISM: Gentiana triflora cv. Hakkoda
<220> FEATURE:
<221> NAME/KEY: CDS
<222> LOCATION: (1)..(1452)
<223> OTHER INFORMATION: Nucleotide sequence of gene coding for
      1-O-acyl-Beta-D-glucose:anthocyanin-O-acyltansferase

<400> SEQUENCE: 9 atg gcg gat aca aac ggc aca gcc aag acg acg agc agg gta aaa tgg       48
Met Ala Asp Thr Asn Gly Thr Ala Lys Thr Thr Ser Arg Val Lys Trp
1               5                   10                  15 tac tta tac ctc tac tgc aac gtc att acg ggg ctg ctt tat ctt caa       96
Tyr Leu Tyr Leu Tyr Cys Asn Val Ile Thr Gly Leu Leu Tyr Leu Gln
                20                  25                  30 cat tct ctt cta caa gta gag gct gct gat tca aca aca gtg aag ttt      144
His Ser Leu Leu Gln Val Glu Ala Ala Asp Ser Thr Thr Val Lys Phe
            35                  40                  45 ctc cct ggt ttt aaa ggc ccc ctt cct ttc gaa ctc gaa acc ggg tat      192
Leu Pro Gly Phe Lys Gly Pro Leu Pro Phe Glu Leu Glu Thr Gly Tyr
    50                  55                  60 att ggg gtg gat aaa gga gaa aat gtg cag ctt ttt tac tat ttt gta      240
Ile Gly Val Asp Lys Gly Glu Asn Val Gln Leu Phe Tyr Tyr Phe Val
65                  70                  75                  80 aag tca tat tct gat tat caa att gat cct ctt gtg cta tgg atg act      288
Lys Ser Tyr Ser Asp Tyr Gln Ile Asp Pro Leu Val Leu Trp Met Thr
                85                  90                  95 gga ggt cct ggt tgt tct gct tta aca gca ttt gcc tat gag ata ggg      336
Gly Gly Pro Gly Cys Ser Ala Leu Thr Ala Phe Ala Tyr Glu Ile Gly
            100                 105                 110 cca ata gct ttt gag gaa gtc ttc tcc aat ggc gac gtt cca cga tta      384
Pro Ile Ala Phe Glu Glu Val Phe Ser Asn Gly Asp Val Pro Arg Leu
        115                 120                 125 gtg ttg aac cct tat tca tgg aca cag gaa gca agc ata gtt ttc gtt      432
Val Leu Asn Pro Tyr Ser Trp Thr Gln Glu Ala Ser Ile Val Phe Val
    130                 135                 140 gat gcc ccg gtt ggc acc gga ttt tcg tat ccg aga tct sca gaa gca      480
Asp Ala Pro Val Gly Thr Gly Phe Ser Tyr Pro Arg Ser Xaa Glu Ala
145                 150                 155                 160 ttt aga tct act ggg ttg caa aca tgt aat caa att tat cag ttt ctc      528
Phe Arg Ser Thr Gly Leu Gln Thr Cys Asn Gln Ile Tyr Gln Phe Leu
                165                 170                 175 aaa aag ttt tta gtc cat cac ccg gaa ttc cta tcc aat ccg tta tat      576
Lys Lys Phe Leu Val His His Pro Glu Phe Leu Ser Asn Pro Leu Tyr
            180                 185                 190 gtc ggc ggc gat tcg tac gcg ggc ctt ttc gtt ccc gtt gta gct gaa      624
Val Gly Gly Asp Ser Tyr Ala Gly Leu Phe Val Pro Val Val Ala Glu
        195                 200                 205 ttg ata gct cat gga aat gaa aac ggg atc gaa cca tcg att aat ctt      672
Leu Ile Ala His Gly Asn Glu Asn Gly Ile Glu Pro Ser Ile Asn Leu
    210                 215                 220 aag gga tat gtt ctt ggt aac cct ctt aca acc cca tat gat gta gat      720
Lys Gly Tyr Val Leu Gly Asn Pro Leu Thr Thr Pro Tyr Asp Val Asp
225                 230                 235                 240
```

| | | | | | | | | | | | | | | | | |
|---|---|---|---|---|---|---|---|---|---|---|---|---|---|---|---|---|
| tat | cga | gtg | ccc | ttt | tct | cat | gga | atg | ggt | att | atc | tct | gat | gag | ctt | 768 |
| Tyr | Arg | Val | Pro | Phe | Ser | His | Gly | Met | Gly | Ile | Ile | Ser | Asp | Glu | Leu | |
| | | | 245 | | | | | 250 | | | | | 255 | | | |
| tat | gag | tcc | ttg | aag | ttg | aac | tgc | aat | ggt | gtg | tac | cat | gat | gta | gat | 816 |
| Tyr | Glu | Ser | Leu | Lys | Leu | Asn | Cys | Asn | Gly | Val | Tyr | His | Asp | Val | Asp | |
| | 260 | | | | | 265 | | | | | 270 | | | | | |
| cct | act | aac | aca | aag | tgt | ttg | aat | gat | ata | gac | act | ttc | aaa | cag | gtg | 864 |
| Pro | Thr | Asn | Thr | Lys | Cys | Leu | Asn | Asp | Ile | Asp | Thr | Phe | Lys | Gln | Val | |
| 275 | | | | | 280 | | | | | 285 | | | | | | |
| ttt | cac | ggc | att | cga | cgt | tca | cat | ata | ctg | gag | ccc | tat | tgt | gta | tcg | 912 |
| Phe | His | Gly | Ile | Arg | Arg | Ser | His | Ile | Leu | Glu | Pro | Tyr | Cys | Val | Ser | |
| | 290 | | | | | 295 | | | | | 300 | | | | | |
| gta | cta | cca | gaa | caa | cag | atg | ctt | agt | acc | gaa | aga | cag | cgt | tct | ctc | 960 |
| Val | Leu | Pro | Glu | Gln | Gln | Met | Leu | Ser | Thr | Glu | Arg | Gln | Arg | Ser | Leu | |
| 305 | | | | | 310 | | | | | 315 | | | | | 320 | |
| cat | gaa | aac | aac | ctc | cgg | att | cct | gac | gtg | ctt | aac | atg | cat | cat | aca | 1008 |
| His | Glu | Asn | Asn | Leu | Arg | Ile | Pro | Asp | Val | Leu | Asn | Met | His | His | Thr | |
| | | | | 325 | | | | | 330 | | | | | 335 | | |
| ttt | aga | tgc | cgt | act | gat | gga | tac | ata | cct | gct | tat | tac | tgg | gct | aac | 1056 |
| Phe | Arg | Cys | Arg | Thr | Asp | Gly | Tyr | Ile | Pro | Ala | Tyr | Tyr | Trp | Ala | Asn | |
| | | | 340 | | | | | 345 | | | | | 350 | | | |
| gat | gat | cgt | gtc | cgc | gag | gcc | ctc | cat | att | cat | aag | gga | agc | atc | aag | 1104 |
| Asp | Asp | Arg | Val | Arg | Glu | Ala | Leu | His | Ile | His | Lys | Gly | Ser | Ile | Lys | |
| | | 355 | | | | | 360 | | | | | 365 | | | | |
| aac | tgg | gta | cgt | tgt | aac | cgt | tcg | ttg | cca | ttc | gaa | gat | tcg | ata | aga | 1152 |
| Asn | Trp | Val | Arg | Cys | Asn | Arg | Ser | Leu | Pro | Phe | Glu | Asp | Ser | Ile | Arg | |
| | 370 | | | | | 375 | | | | | 380 | | | | | |
| aac | gtt | gta | cct | tat | cat | gca | aac | ctc | agc | aaa | aaa | gga | tat | aga | tca | 1200 |
| Asn | Val | Val | Pro | Tyr | His | Ala | Asn | Leu | Ser | Lys | Lys | Gly | Tyr | Arg | Ser | |
| 385 | | | | | 390 | | | | | 395 | | | | | 400 | |
| ctt | ata | tac | agc | gga | gat | cat | gac | gcg | atg | gtg | cca | ttc | atg | gct | act | 1248 |
| Leu | Ile | Tyr | Ser | Gly | Asp | His | Asp | Ala | Met | Val | Pro | Phe | Met | Ala | Thr | |
| | | | | 405 | | | | | 410 | | | | | 415 | | |
| caa | gca | tgg | ata | aga | tca | tta | aac | tac | tcc | att | gtt | gat | gaa | tgg | cgc | 1296 |
| Gln | Ala | Trp | Ile | Arg | Ser | Leu | Asn | Tyr | Ser | Ile | Val | Asp | Glu | Trp | Arg | |
| | | | 420 | | | | | 425 | | | | | 430 | | | |
| caa | tgg | att | gtt | gaa | ggc | caa | gtt | gct | gga | tat | aca | aga | aca | tat | gct | 1344 |
| Gln | Trp | Ile | Val | Glu | Gly | Gln | Val | Ala | Gly | Tyr | Thr | Arg | Thr | Tyr | Ala | |
| | | 435 | | | | | 440 | | | | | 445 | | | | |
| aac | cag | atg | aca | ttt | gct | aca | gta | aag | gga | ggt | ggg | cat | act | gct | cct | 1392 |
| Asn | Gln | Met | Thr | Phe | Ala | Thr | Val | Lys | Gly | Gly | Gly | His | Thr | Ala | Pro | |
| | 450 | | | | | 455 | | | | | 460 | | | | | |
| gaa | tat | aag | cca | aaa | gaa | tgc | aaa | gca | atg | ttt | aaa | agg | tgg | ata | act | 1440 |
| Glu | Tyr | Lys | Pro | Lys | Glu | Cys | Lys | Ala | Met | Phe | Lys | Arg | Trp | Ile | Thr | |
| 465 | | | | | 470 | | | | | 475 | | | | | 480 | |
| cat | aaa | ccg | ttg | tag | | | | | | | | | | | | 1455 |
| His | Lys | Pro | Leu | | | | | | | | | | | | | |

```
<210> SEQ ID NO 10
<211> LENGTH: 484
<212> TYPE: PRT
<213> ORGANISM: Gentiana triflora cv. Hakkoda
<220> FEATURE:
<221> NAME/KEY: misc_feature
<223> OTHER INFORMATION: Amino acid sequence of 1-O-acyl-Beta-D-glucose:
      anthocyanin-O-acyltansferase
<220> FEATURE:
<221> NAME/KEY: misc_feature
<222> LOCATION: (158)..(158)
<223> OTHER INFORMATION: The 'Xaa' at location 158 stands for Ala, or
      Pro.
```

<400> SEQUENCE: 10

Met Ala Asp Thr Asn Gly Thr Ala Lys Thr Thr Ser Arg Val Lys Trp
1               5                   10                  15

Tyr Leu Tyr Leu Tyr Cys Asn Val Ile Thr Gly Leu Leu Tyr Leu Gln
            20                  25                  30

His Ser Leu Leu Gln Val Glu Ala Ala Asp Ser Thr Thr Val Lys Phe
        35                  40                  45

Leu Pro Gly Phe Lys Gly Pro Leu Pro Phe Glu Leu Glu Thr Gly Tyr
    50                  55                  60

Ile Gly Val Asp Lys Gly Glu Asn Val Gln Leu Phe Tyr Tyr Phe Val
65                  70                  75                  80

Lys Ser Tyr Ser Asp Tyr Gln Ile Asp Pro Leu Val Leu Trp Met Thr
                85                  90                  95

Gly Gly Pro Gly Cys Ser Ala Leu Thr Ala Phe Ala Tyr Glu Ile Gly
            100                 105                 110

Pro Ile Ala Phe Glu Glu Val Phe Ser Asn Gly Asp Val Pro Arg Leu
        115                 120                 125

Val Leu Asn Pro Tyr Ser Trp Thr Gln Glu Ala Ser Ile Val Phe Val
130                 135                 140

Asp Ala Pro Val Gly Thr Gly Phe Ser Tyr Pro Arg Ser Xaa Glu Ala
145                 150                 155                 160

Phe Arg Ser Thr Gly Leu Gln Thr Cys Asn Gln Ile Tyr Gln Phe Leu
                165                 170                 175

Lys Lys Phe Leu Val His His Pro Glu Phe Leu Ser Asn Pro Leu Tyr
            180                 185                 190

Val Gly Gly Asp Ser Tyr Ala Gly Leu Phe Val Pro Val Val Ala Glu
        195                 200                 205

Leu Ile Ala His Gly Asn Glu Asn Gly Ile Glu Pro Ser Ile Asn Leu
210                 215                 220

Lys Gly Tyr Val Leu Gly Asn Pro Leu Thr Thr Pro Tyr Asp Val Asp
225                 230                 235                 240

Tyr Arg Val Pro Phe Ser His Gly Met Gly Ile Ile Ser Asp Glu Leu
                245                 250                 255

Tyr Glu Ser Leu Lys Leu Asn Cys Asn Gly Val Tyr His Asp Val Asp
            260                 265                 270

Pro Thr Asn Thr Lys Cys Leu Asn Asp Ile Asp Thr Phe Lys Gln Val
        275                 280                 285

Phe His Gly Ile Arg Arg Ser His Ile Leu Glu Pro Tyr Cys Val Ser
    290                 295                 300

Val Leu Pro Glu Gln Gln Met Leu Ser Thr Glu Arg Gln Arg Ser Leu
305                 310                 315                 320

His Glu Asn Asn Leu Arg Ile Pro Asp Val Leu Asn Met His His Thr
                325                 330                 335

Phe Arg Cys Arg Thr Asp Gly Tyr Ile Pro Ala Tyr Tyr Trp Ala Asn
            340                 345                 350

Asp Asp Arg Val Arg Glu Ala Leu His Ile His Lys Gly Ser Ile Lys
        355                 360                 365

Asn Trp Val Arg Cys Asn Arg Ser Leu Pro Phe Glu Asp Ser Ile Arg
    370                 375                 380

Asn Val Val Pro Tyr His Ala Asn Leu Ser Lys Lys Gly Tyr Arg Ser
385                 390                 395                 400

Leu Ile Tyr Ser Gly Asp His Asp Ala Met Val Pro Phe Met Ala Thr
                405                 410                 415

-continued

```
Gln Ala Trp Ile Arg Ser Leu Asn Tyr Ser Ile Val Asp Glu Trp Arg
                420                 425                 430
Gln Trp Ile Val Glu Gly Gln Val Ala Gly Tyr Thr Arg Thr Tyr Ala
            435                 440                 445
Asn Gln Met Thr Phe Ala Thr Val Lys Gly Gly His Thr Ala Pro
450                 455                 460
Glu Tyr Lys Pro Lys Glu Cys Lys Ala Met Phe Lys Arg Trp Ile Thr
465                 470                 475                 480
His Lys Pro Leu

<210> SEQ ID NO 11
<211> LENGTH: 1446
<212> TYPE: DNA
<213> ORGANISM: Lobelia erinus cv. Riviera Midnight Blue
<220> FEATURE:
<221> NAME/KEY: CDS
<222> LOCATION: (1)..(1443)
<223> OTHER INFORMATION: Nucleotide sequence of gene coding for
      1-O-acyl-Beta-D-glucose:anthocyanin-O-acyltansferase

<400> SEQUENCE: 11 atg gcg ttt ggt atg cca ttt tcg tgg gac tgg aag ctc gga tgg gtg      48
Met Ala Phe Gly Met Pro Phe Ser Trp Asp Trp Lys Leu Gly Trp Val
1               5                   10                  15 ctg cag att atc ctc tta ctt gca gtt tcc acc att gtc gcg ccg cgg      96
Leu Gln Ile Ile Leu Leu Leu Ala Val Ser Thr Ile Val Ala Pro Arg
            20                  25                  30 tcg atc atc gac act tta ccg gga ttc aag ggc att ctt cct ttc aaa     144
Ser Ile Ile Asp Thr Leu Pro Gly Phe Lys Gly Ile Leu Pro Phe Lys
        35                  40                  45 ctt gag acc ggg tac ata agc gtc gga gaa tcg gat gaa att caa cta     192
Leu Glu Thr Gly Tyr Ile Ser Val Gly Glu Ser Asp Glu Ile Gln Leu
    50                  55                  60 ttc tac tac ttt ttt ccg tcg gag gga agt cct gag aaa gac cct ctt     240
Phe Tyr Tyr Phe Phe Pro Ser Glu Gly Ser Pro Glu Lys Asp Pro Leu
65                  70                  75                  80 atg att tgg ttc acg ggt ggc cct ggt tgt tct gga ctt tct gct ttt     288
Met Ile Trp Phe Thr Gly Gly Pro Gly Cys Ser Gly Leu Ser Ala Phe
                85                  90                  95 atg gaa aac aaa ggt cca ttg att ttc agt gat gaa tca cca ttt gat     336
Met Glu Asn Lys Gly Pro Leu Ile Phe Ser Asp Glu Ser Pro Phe Asp
            100                 105                 110 gga aac ttg cca cca ctt act aca aac cca cac aca tta aca aag gtt     384
Gly Asn Leu Pro Pro Leu Thr Thr Asn Pro His Thr Leu Thr Lys Val
        115                 120                 125 gca agt ata att ttc ata gat tca cca gtc aaa gca gga ttc tcc tat     432
Ala Ser Ile Ile Phe Ile Asp Ser Pro Val Lys Ala Gly Phe Ser Tyr
    130                 135                 140 gca act acg tat gaa ggt tac aac atg tca gat acg aaa aca gca aaa     480
Ala Thr Thr Tyr Glu Gly Tyr Asn Met Ser Asp Thr Lys Thr Ala Lys
145                 150                 155                 160 gaa gct acc acc ttc tta aag aag tgg ttg ttg gag cat ccc gag ttt     528
Glu Ala Thr Thr Phe Leu Lys Lys Trp Leu Leu Glu His Pro Glu Phe
                165                 170                 175 gac aaa aat cca ctt tat att gct ggt gat tcc tat gct gga ctt att     576
Asp Lys Asn Pro Leu Tyr Ile Ala Gly Asp Ser Tyr Ala Gly Leu Ile
            180                 185                 190 gta ccg atg gtt gtc ttt cac gtt tca aat gct att gaa gct gga cag     624
Val Pro Met Val Val Phe His Val Ser Asn Ala Ile Glu Ala Gly Gln
        195                 200                 205
```

```
atg cca aac acg aat ctc gag gga tac gtg cta ggc aac cca ttt aca      672
Met Pro Asn Thr Asn Leu Glu Gly Tyr Val Leu Gly Asn Pro Phe Thr
    210                 215                 220 gat aca ccc aat gat gta gga tca agg att cca tat gct aat aga atg      720
Asp Thr Pro Asn Asp Val Gly Ser Arg Ile Pro Tyr Ala Asn Arg Met
225                 230                 235                 240 gcg tta ata tct gat caa tat tat gag tgg gct aaa acg agc tgc caa      768
Ala Leu Ile Ser Asp Gln Tyr Tyr Glu Trp Ala Lys Thr Ser Cys Gln
                245                 250                 255 ggt gac tac agt cga caa gat cca agc aat aca aaa tgc ctt ctt cat      816
Gly Asp Tyr Ser Arg Gln Asp Pro Ser Asn Thr Lys Cys Leu Leu His
            260                 265                 270 ctt caa cta atc gac aag tgc att gaa gat ata tat atc gac tat att      864
Leu Gln Leu Ile Asp Lys Cys Ile Glu Asp Ile Tyr Ile Asp Tyr Ile
        275                 280                 285 ctg gga ccc aaa tgt aag aat ggt atg aat cta caa agt gga gac aaa      912
Leu Gly Pro Lys Cys Lys Asn Gly Met Asn Leu Gln Ser Gly Asp Lys
    290                 295                 300 ttc atg ttg gga aaa cag tct tcc caa gac atg atc cta tta cct tct      960
Phe Met Leu Gly Lys Gln Ser Ser Gln Asp Met Ile Leu Leu Pro Ser
305                 310                 315                 320 cta cgc gag gaa cat tcc gag cag tgt gag gag gaa cta aaa aca cat     1008
Leu Arg Glu Glu His Ser Glu Gln Cys Glu Glu Glu Leu Lys Thr His
                325                 330                 335 ctt tgc gaa ata tgg gct aac gag cca gtt gtc caa caa gcc ctc cac     1056
Leu Cys Glu Ile Trp Ala Asn Glu Pro Val Val Gln Gln Ala Leu His
            340                 345                 350 gta cga aag gga aca cta act tca gag tgg atg aga tgt aat aaa tct     1104
Val Arg Lys Gly Thr Leu Thr Ser Glu Trp Met Arg Cys Asn Lys Ser
        355                 360                 365 agt tca act tac att aat gat atg cca act agt ata gag tat cat cag     1152
Ser Ser Thr Tyr Ile Asn Asp Met Pro Thr Ser Ile Glu Tyr His Gln
    370                 375                 380 atc ctt agt aag aag acc tat cga gct tta ata tac agt ggt gac cat     1200
Ile Leu Ser Lys Lys Thr Tyr Arg Ala Leu Ile Tyr Ser Gly Asp His
385                 390                 395                 400 gac atg act gtg cca tac gtg ggt aca cta gct tgg ata cat aag ctt     1248
Asp Met Thr Val Pro Tyr Val Gly Thr Leu Ala Trp Ile His Lys Leu
                405                 410                 415 aac ttg agt ata gag gmg tac tgg agg ccg tgg ctc gtt gat aat caa     1296
Asn Leu Ser Ile Glu Xaa Tyr Trp Arg Pro Trp Leu Val Asp Asn Gln
            420                 425                 430 gct gca gga ttt act gag aag tat caa gga aaa aat gga ttc tcg ctt     1344
Ala Ala Gly Phe Thr Glu Lys Tyr Gln Gly Lys Asn Gly Phe Ser Leu
        435                 440                 445 acc ttt gga act gtc aag gga gca gga cat gta gca gca aga tac aag     1392
Thr Phe Gly Thr Val Lys Gly Ala Gly His Val Ala Ala Arg Tyr Lys
    450                 455                 460 cct aaa gga act tcc acc ata att gga agg tgg ctt act cgt agt tta     1440
Pro Lys Gly Thr Ser Thr Ile Ile Gly Arg Trp Leu Thr Arg Ser Leu
465                 470                 475                 480 ttg tga                                                              1446
Leu
```

<210> SEQ ID NO 12
<211> LENGTH: 481
<212> TYPE: PRT
<213> ORGANISM: Lobelia erinus cv. Riviera Midnight Blue
<220> FEATURE:
<221> NAME/KEY: misc_feature
<223> OTHER INFORMATION: Amino acid sequence of 1-O-acyl-Beta-D-glucose:
      anthocyanin-O-acyltansferase -continued

```
<220> FEATURE:
<221> NAME/KEY: misc_feature
<222> LOCATION: (422)..(422)
<223> OTHER INFORMATION: The 'Xaa' at location 422 stands for Glu, or
      Ala.

<400> SEQUENCE: 12

Met Ala Phe Gly Met Pro Phe Ser Trp Asp Trp Lys Leu Gly Trp Val
1               5                   10                  15

Leu Gln Ile Ile Leu Leu Ala Val Ser Thr Ile Val Ala Pro Arg
            20                  25                  30

Ser Ile Ile Asp Thr Leu Pro Gly Phe Lys Gly Ile Leu Pro Phe Lys
            35                  40                  45

Leu Glu Thr Gly Tyr Ile Ser Val Gly Glu Ser Asp Glu Ile Gln Leu
        50                  55                  60

Phe Tyr Tyr Phe Phe Pro Ser Glu Gly Ser Pro Glu Lys Asp Pro Leu
65                  70                  75                  80

Met Ile Trp Phe Thr Gly Gly Pro Gly Cys Ser Gly Leu Ser Ala Phe
                85                  90                  95

Met Glu Asn Lys Gly Pro Leu Ile Phe Ser Asp Glu Ser Pro Phe Asp
            100                 105                 110

Gly Asn Leu Pro Pro Leu Thr Thr Asn Pro His Thr Leu Thr Lys Val
        115                 120                 125

Ala Ser Ile Ile Phe Ile Asp Ser Pro Val Lys Ala Gly Phe Ser Tyr
130                 135                 140

Ala Thr Thr Tyr Glu Gly Tyr Asn Met Ser Asp Thr Lys Thr Ala Lys
145                 150                 155                 160

Glu Ala Thr Thr Phe Leu Lys Lys Trp Leu Leu Glu His Pro Glu Phe
                165                 170                 175

Asp Lys Asn Pro Leu Tyr Ile Ala Gly Asp Ser Tyr Ala Gly Leu Ile
            180                 185                 190

Val Pro Met Val Val Phe His Val Ser Asn Ala Ile Glu Ala Gly Gln
        195                 200                 205

Met Pro Asn Thr Asn Leu Glu Gly Tyr Val Leu Gly Asn Pro Phe Thr
210                 215                 220

Asp Thr Pro Asn Asp Val Gly Ser Arg Ile Pro Tyr Ala Asn Arg Met
225                 230                 235                 240

Ala Leu Ile Ser Asp Gln Tyr Tyr Glu Trp Ala Lys Thr Ser Cys Gln
                245                 250                 255

Gly Asp Tyr Ser Arg Gln Asp Pro Ser Asn Thr Lys Cys Leu Leu His
            260                 265                 270

Leu Gln Leu Ile Asp Lys Cys Ile Glu Asp Ile Tyr Ile Asp Tyr Ile
        275                 280                 285

Leu Gly Pro Lys Cys Lys Asn Gly Met Asn Leu Gln Ser Gly Asp Lys
    290                 295                 300

Phe Met Leu Gly Lys Gln Ser Ser Gln Asp Met Ile Leu Leu Pro Ser
305                 310                 315                 320

Leu Arg Glu Glu His Ser Glu Gln Cys Glu Glu Leu Lys Thr His
                325                 330                 335

Leu Cys Glu Ile Trp Ala Asn Glu Pro Val Val Gln Gln Ala Leu His
            340                 345                 350

Val Arg Lys Gly Thr Leu Thr Ser Glu Trp Met Arg Cys Asn Lys Ser
        355                 360                 365

Ser Ser Thr Tyr Ile Asn Asp Met Pro Thr Ser Ile Glu Tyr His Gln
    370                 375                 380
```

```
Ile Leu Ser Lys Lys Thr Tyr Arg Ala Leu Ile Tyr Ser Gly Asp His
385                 390                 395                 400

Asp Met Thr Val Pro Tyr Val Gly Thr Leu Ala Trp Ile His Lys Leu
                405                 410                 415

Asn Leu Ser Ile Glu Xaa Tyr Trp Arg Pro Trp Leu Val Asp Asn Gln
            420                 425                 430

Ala Ala Gly Phe Thr Glu Lys Tyr Gln Gly Lys Asn Gly Phe Ser Leu
        435                 440                 445

Thr Phe Gly Thr Val Lys Gly Ala Gly His Val Ala Ala Arg Tyr Lys
    450                 455                 460

Pro Lys Gly Thr Ser Thr Ile Ile Gly Arg Trp Leu Thr Arg Ser Leu
465                 470                 475                 480

Leu

<210> SEQ ID NO 13
<211> LENGTH: 1788
<212> TYPE: DNA
<213> ORGANISM: Clitoria ternatea cv. Double Blue
<220> FEATURE:
<221> NAME/KEY: CDS
<222> LOCATION: (71)..(1489)
<223> OTHER INFORMATION: Nucleotide sequence of gene coding for
      UDP-glucose:hydroxycinnamic acid 1-O-glucosyltransferase

<400> SEQUENCE: 13
ccatgctgca taaatattaa accccaagag aagaaaaaat atcaaagaaa gacatcgaag      60
agaaagaaaa atg ggg tct gaa gct tcg ttt cac gtt ctg atg gtt tcg        109
            Met Gly Ser Glu Ala Ser Phe His Val Leu Met Val Ser
            1               5                   10 ttt cca gca caa gga cac ata aac cct ctg cta aga cta ggc aag ttt       157
Phe Pro Ala Gln Gly His Ile Asn Pro Leu Leu Arg Leu Gly Lys Phe
15                  20                  25 ctt gct gca cag ggt ttg ttt gta acc ttt gct acc aca gaa acc gct       205
Leu Ala Ala Gln Gly Leu Phe Val Thr Phe Ala Thr Thr Glu Thr Ala
30                  35                  40                  45 ggt aaa aac atg cga acc gct aac gaa aac atc act aag aaa tca gtg       253
Gly Lys Asn Met Arg Thr Ala Asn Glu Asn Ile Thr Lys Lys Ser Val
                50                  55                  60 act cca ctt ggt gac ggt ttt ctc aag ttc gat ttc ttc gat gat ggt       301
Thr Pro Leu Gly Asp Gly Phe Leu Lys Phe Asp Phe Phe Asp Asp Gly
            65                  70                  75 ttg gca gag gat gat ccc atc aga aag aat cta agt gac ttt tgt gca       349
Leu Ala Glu Asp Asp Pro Ile Arg Lys Asn Leu Ser Asp Phe Cys Ala
        80                  85                  90 cag ctt gaa gtc gtt ggg aag aaa tat gtt tct gaa atg ata cac ttt       397
Gln Leu Glu Val Val Gly Lys Lys Tyr Val Ser Glu Met Ile His Phe
95                  100                 105 cat gtt gag tca aac cag cca att tcc tgc atc ata aac aac cct ttt       445
His Val Glu Ser Asn Gln Pro Ile Ser Cys Ile Ile Asn Asn Pro Phe
110                 115                 120                 125 gtt cca tgg gtt agt gat gta gct gct gaa cat aag gta cct tct gct       493
Val Pro Trp Val Ser Asp Val Ala Ala Glu His Lys Val Pro Ser Ala
                130                 135                 140 ttg ctc tgg att caa tct att gct gtc ttc act gct tat ttt agt tat       541
Leu Leu Trp Ile Gln Ser Ile Ala Val Phe Thr Ala Tyr Phe Ser Tyr
            145                 150                 155 ctc cac aaa ctt gta cct ttc cct tca gat gct gac cct ttt gtt gat       589
Leu His Lys Leu Val Pro Phe Pro Ser Asp Ala Asp Pro Phe Val Asp
        160                 165                 170
```

| | | |
|---|---|---|
| gct cta ttg cct tct ata act ctc aaa tac aat gaa att cca gac ttt<br>Ala Leu Leu Pro Ser Ile Thr Leu Lys Tyr Asn Glu Ile Pro Asp Phe<br>175                     180                    185 | | 637 |
| ttg cat cct ttt agc cca tat cca ttt ctt ggg aca ctc ata ttg gaa<br>Leu His Pro Phe Ser Pro Tyr Pro Phe Leu Gly Thr Leu Ile Leu Glu<br>190                     195                    200                    205 | | 685 |
| caa att aag aaa ctg tcc aaa ccg ttc tgt gtt ctg gtg gac agt ttt<br>Gln Ile Lys Lys Leu Ser Lys Pro Phe Cys Val Leu Val Asp Ser Phe<br>                   210                    215                    220 | | 733 |
| gag gaa cta gag cat gag ttc atc acc tat ctg tcg aag ttt gtg aac<br>Glu Glu Leu Glu His Glu Phe Ile Thr Tyr Leu Ser Lys Phe Val Asn<br>                   225                    230                    235 | | 781 |
| atg agg cct gtt ggg cct ctg ctc aag aac cca aaa gca ata acc gca<br>Met Arg Pro Val Gly Pro Leu Leu Lys Asn Pro Lys Ala Ile Thr Ala<br>      240                    245                    250 | | 829 |
| gga ggt att atc cgt ggt gat ttc atg aag agt gat gat tgc ata gag<br>Gly Gly Ile Ile Arg Gly Asp Phe Met Lys Ser Asp Asp Cys Ile Glu<br>      255                    260                    265 | | 877 |
| tgg cta aac tca cgt gag tca aaa tct gta gtg tac att tct ttt ggt<br>Trp Leu Asn Ser Arg Glu Ser Lys Ser Val Val Tyr Ile Ser Phe Gly<br>270                     275                    280                    285 | | 925 |
| agc att gtg tat ctg cct caa gaa caa gtg agt gaa att gca tat ggg<br>Ser Ile Val Tyr Leu Pro Gln Glu Gln Val Ser Glu Ile Ala Tyr Gly<br>                   290                    295                    300 | | 973 |
| ctg gcg gag tca aaa gtt tca ttt tta tgg gtt gta aag ccc ccc agt<br>Leu Ala Glu Ser Lys Val Ser Phe Leu Trp Val Val Lys Pro Pro Ser<br>                   305                    310                    315 | | 1021 |
| aag gaa tcg ggg ctc caa tct cat gtt ttg cca gat ggg ttc ctt gat<br>Lys Glu Ser Gly Leu Gln Ser His Val Leu Pro Asp Gly Phe Leu Asp<br>            320                    325                    330 | | 1069 |
| agc aca aaa gat aga ggg aag gtg gtg cag tgg agc cca caa gag gaa<br>Ser Thr Lys Asp Arg Gly Lys Val Val Gln Trp Ser Pro Gln Glu Glu<br>335                     340                    345 | | 1117 |
| gtg cta tct cat cct tca gtt gca tgt ttt gtg aca cac tgc ggg tgg<br>Val Leu Ser His Pro Ser Val Ala Cys Phe Val Thr His Cys Gly Trp<br>350                     355                    360                    365 | | 1165 |
| aac tct tca atg gaa gca att agt ttg gga gtg cca atg ttg aca ttt<br>Asn Ser Ser Met Glu Ala Ile Ser Leu Gly Val Pro Met Leu Thr Phe<br>                   370                    375                    380 | | 1213 |
| cca gca tgg ggg gac caa gtt aca aat gca aag ttc ttg gtt gat gta<br>Pro Ala Trp Gly Asp Gln Val Thr Asn Ala Lys Phe Leu Val Asp Val<br>                   385                    390                    395 | | 1261 |
| ttt gga gtt ggg ata agg ctt ggc tat agc aat gct gat aac aaa ttg<br>Phe Gly Val Gly Ile Arg Leu Gly Tyr Ser Asn Ala Asp Asn Lys Leu<br>      400                    405                    410 | | 1309 |
| gtg aca aga gaa gag gtg aag aag tgc ttg tta gaa gca ata caa ggg<br>Val Thr Arg Glu Glu Val Lys Lys Cys Leu Leu Glu Ala Ile Gln Gly<br>      415                    420                    425 | | 1357 |
| cca aaa gca gag gag ttg aaa gaa aac gtg cag aag tgg aag aag gct<br>Pro Lys Ala Glu Glu Leu Lys Glu Asn Val Gln Lys Trp Lys Lys Ala<br>430                     435                    440                    445 | | 1405 |
| gca atg gcc gca gtg gct ctt ggt ggc tcc tct gac aga cac ctt gct<br>Ala Met Ala Ala Val Ala Leu Gly Gly Ser Ser Asp Arg His Leu Ala<br>                   450                    455                    460 | | 1453 |
| gca ttt ctg gat gag att aga aac cgt ggt aac cct tagcattgtc<br>Ala Phe Leu Asp Glu Ile Arg Asn Arg Gly Asn Pro<br>                   465                    470 | | 1499 |

-continued

```
ttcggtttac aaaattaaaa acaaaaaagt tcgatatttt tttatgtatg tgacatgtct    1559
atgttactgt gagagtgtag ggcaattatt gttacttaat aaatgttatg ttctgtattt    1619
cgatatgacc attgttatag ttcgcggttt actatgcaga catggtgcat gatgggtata    1679
attatgactt gattctgaaa tattactacc aataatatta tatgttttct cttaaaaaaa    1739
aaaaaaaaaa aaaaaaaaaa aaaaaaaaaa aaaaaaaaaa aaaaaaaaa               1788
```

<210> SEQ ID NO 14
<211> LENGTH: 473
<212> TYPE: PRT
<213> ORGANISM: Clitoria ternatea cv. Double Blue
<220> FEATURE:
<221> NAME/KEY: misc_feature
<223> OTHER INFORMATION: Amino acid sequence of UDP-glucose:
      hydroxycinnamic acid 1-O-glucosyltransferase

<400> SEQUENCE: 14

```
Met Gly Ser Glu Ala Ser Phe His Val Leu Met Val Ser Phe Pro Ala
1               5                   10                  15

Gln Gly His Ile Asn Pro Leu Leu Arg Leu Gly Lys Phe Leu Ala Ala
            20                  25                  30

Gln Gly Leu Phe Val Thr Phe Ala Thr Thr Glu Thr Ala Gly Lys Asn
        35                  40                  45

Met Arg Thr Ala Asn Glu Asn Ile Thr Lys Lys Ser Val Thr Pro Leu
    50                  55                  60

Gly Asp Gly Phe Leu Lys Phe Asp Phe Phe Asp Asp Gly Leu Ala Glu
65                  70                  75                  80

Asp Asp Pro Ile Arg Lys Asn Leu Ser Asp Phe Cys Ala Gln Leu Glu
                85                  90                  95

Val Val Gly Lys Lys Tyr Val Ser Glu Met Ile His Phe His Val Glu
            100                 105                 110

Ser Asn Gln Pro Ile Ser Cys Ile Ile Asn Asn Pro Phe Val Pro Trp
        115                 120                 125

Val Ser Asp Val Ala Ala Glu His Lys Val Pro Ser Ala Leu Leu Trp
    130                 135                 140

Ile Gln Ser Ile Ala Val Phe Thr Ala Tyr Phe Ser Tyr Leu His Lys
145                 150                 155                 160

Leu Val Pro Phe Pro Ser Asp Ala Asp Pro Phe Val Asp Ala Leu Leu
                165                 170                 175

Pro Ser Ile Thr Leu Lys Tyr Asn Glu Ile Pro Asp Phe Leu His Pro
            180                 185                 190

Phe Ser Pro Tyr Pro Phe Leu Gly Thr Leu Ile Leu Glu Gln Ile Lys
        195                 200                 205

Lys Leu Ser Lys Pro Phe Cys Val Leu Val Asp Ser Phe Glu Glu Leu
    210                 215                 220

Glu His Glu Phe Ile Thr Tyr Leu Ser Lys Phe Val Asn Met Arg Pro
225                 230                 235                 240

Val Gly Pro Leu Leu Lys Asn Pro Lys Ala Ile Thr Ala Gly Gly Ile
                245                 250                 255

Ile Arg Gly Asp Phe Met Lys Ser Asp Asp Cys Ile Glu Trp Leu Asn
            260                 265                 270

Ser Arg Glu Ser Lys Ser Val Val Tyr Ile Ser Phe Gly Ser Ile Val
        275                 280                 285

Tyr Leu Pro Gln Glu Gln Val Ser Glu Ile Ala Tyr Gly Leu Ala Glu
    290                 295                 300
```

```
Ser Lys Val Ser Phe Leu Trp Val Val Lys Pro Ser Lys Glu Ser
305                 310                 315                 320

Gly Leu Gln Ser His Val Leu Pro Asp Gly Phe Leu Asp Ser Thr Lys
            325                 330                 335

Asp Arg Gly Lys Val Val Gln Trp Ser Pro Gln Glu Glu Val Leu Ser
        340                 345                 350

His Pro Ser Val Ala Cys Phe Val Thr His Cys Gly Trp Asn Ser Ser
    355                 360                 365

Met Glu Ala Ile Ser Leu Gly Val Pro Met Leu Thr Phe Pro Ala Trp
370                 375                 380

Gly Asp Gln Val Thr Asn Ala Lys Phe Leu Val Asp Val Phe Gly Val
385                 390                 395                 400

Gly Ile Arg Leu Gly Tyr Ser Asn Ala Asp Asn Lys Leu Val Thr Arg
            405                 410                 415

Glu Glu Val Lys Lys Cys Leu Leu Glu Ala Ile Gln Gly Pro Lys Ala
        420                 425                 430

Glu Glu Leu Lys Glu Asn Val Gln Lys Trp Lys Lys Ala Ala Met Ala
    435                 440                 445

Ala Val Ala Leu Gly Gly Ser Ser Asp Arg His Leu Ala Ala Phe Leu
450                 455                 460

Asp Glu Ile Arg Asn Arg Gly Asn Pro
465                 470

<210> SEQ ID NO 15
<211> LENGTH: 1574
<212> TYPE: DNA
<213> ORGANISM: Lobelia erinus cv.Riviera Midnight Blue
<220> FEATURE:
<221> NAME/KEY: CDS
<222> LOCATION: (2)..(1459)
<223> OTHER INFORMATION: Nucleotide sequence of gene coding for
      UDP-glucose:hydroxycinnamic acid 1-O-glucosyltransferase

<400> SEQUENCE: 15 g atg ggc tca ctg cag ggt act act acc gtc gaa aat ctc acc cat gtc     49
  Met Gly Ser Leu Gln Gly Thr Thr Thr Val Glu Asn Leu Thr His Val
  1               5                   10                  15 ttc cta gtg tct ttc ccc ggt caa ggc cac gtc aac ccc ctc ctc cgt      97
Phe Leu Val Ser Phe Pro Gly Gln Gly His Val Asn Pro Leu Leu Arg
            20                  25                  30 ctc ggc aag atc ctt gcc ttc aag ggc ctc tta gta aca ttc tcc gcc     145
Leu Gly Lys Ile Leu Ala Phe Lys Gly Leu Leu Val Thr Phe Ser Ala
        35                  40                  45 cca gaa atg gtg ggc gaa atc ata aaa ggc gcc aac aag tac atc tcc     193
Pro Glu Met Val Gly Glu Ile Ile Lys Gly Ala Asn Lys Tyr Ile Ser
    50                  55                  60 gac gac gag ctc act ccc atc ggc gac ggc atg att cgc ttc gag ttc     241
Asp Asp Glu Leu Thr Pro Ile Gly Asp Gly Met Ile Arg Phe Glu Phe
65                  70                  75                  80 ttc tcc gac ggc ctt ggc aac acc aaa gag gac aac tct ttg cgc ggc     289
Phe Ser Asp Gly Leu Gly Asn Thr Lys Glu Asp Asn Ser Leu Arg Gly
                85                  90                  95 aac atg gat ctt tat atg ccc caa cta gct acc ttc gcc aag aaa tcg     337
Asn Met Asp Leu Tyr Met Pro Gln Leu Ala Thr Phe Ala Lys Lys Ser
            100                 105                 110 tta tct gaa ata cta ata aag cac gag aaa cat ggc cgc ccc gtc gcc     385
Leu Ser Glu Ile Leu Ile Lys His Glu Lys His Gly Arg Pro Val Ala
        115                 120                 125
```

```
tgc ctt ata aac aac cca ttt ata cct tgg att tcg gag ttg gcc gaa    433
Cys Leu Ile Asn Asn Pro Phe Ile Pro Trp Ile Ser Glu Leu Ala Glu
    130             135                 140 gag ttt aat atc cct tcc gcc gtt ctg tgg gta caa tct tgt gct tct    481
Glu Phe Asn Ile Pro Ser Ala Val Leu Trp Val Gln Ser Cys Ala Ser
145                 150                 155                 160 ttt tca gct tat tat cac tac cac cat ggt tta gta cct ttt ccg acc    529
Phe Ser Ala Tyr Tyr His Tyr His His Gly Leu Val Pro Phe Pro Thr
                165                 170                 175 gaa aac gag ccg gag cgt gat gtt cag ctc cca aac atg cca ttg tta    577
Glu Asn Glu Pro Glu Arg Asp Val Gln Leu Pro Asn Met Pro Leu Leu
            180                 185                 190 aag tac gat gag atc cct ggc ttc ttg ctc cct tcc agt ccg tac ggc    625
Lys Tyr Asp Glu Ile Pro Gly Phe Leu Leu Pro Ser Ser Pro Tyr Gly
        195                 200                 205 ttc ttg agg agg gct att ttg ggt cag ttc aaa ctt ttg tct aaa cca    673
Phe Leu Arg Arg Ala Ile Leu Gly Gln Phe Lys Leu Leu Ser Lys Pro
    210                 215                 220 ata tgc att tta gtt gaa tct ttt caa gaa ctg gaa aat gat tgc att    721
Ile Cys Ile Leu Val Glu Ser Phe Gln Glu Leu Glu Asn Asp Cys Ile
225                 230                 235                 240 aat tac tta tct acc ctc tgc cct att aaa ccc att ggc cct tta ttc    769
Asn Tyr Leu Ser Thr Leu Cys Pro Ile Lys Pro Ile Gly Pro Leu Phe
                245                 250                 255 agc aac ccg agt gtc aga aac ggg tcc tcc att cga ggg gat ttt atg    817
Ser Asn Pro Ser Val Arg Asn Gly Ser Ser Ile Arg Gly Asp Phe Met
            260                 265                 270 aaa gta gag gac tgt att gat tgg ctg aac acc aga gct gac tcc tct    865
Lys Val Glu Asp Cys Ile Asp Trp Leu Asn Thr Arg Ala Asp Ser Ser
        275                 280                 285 gtt gtg tac gta tcg ttc ggg agt att gta tac gtg aag cag gag cag    913
Val Val Tyr Val Ser Phe Gly Ser Ile Val Tyr Val Lys Gln Glu Gln
    290                 295                 300 att act gaa ata gcc cgt ggg ctt gcg gat tcg ggc ctt tct ttc ttg    961
Ile Thr Glu Ile Ala Arg Gly Leu Ala Asp Ser Gly Leu Ser Phe Leu
305                 310                 315                 320 tgg gct ttc aaa cag ccc ggt ata gat atg ggc ctc act ccg cct tcg   1009
Trp Ala Phe Lys Gln Pro Gly Ile Asp Met Gly Leu Thr Pro Pro Ser
                325                 330                 335 tta ccg gac gga ttc ctg gag gag gtg aag ggg agg ggg aaa gtg gtg   1057
Leu Pro Asp Gly Phe Leu Glu Glu Val Lys Gly Arg Gly Lys Val Val
            340                 345                 350 gag tgg tgt tcg cag gag gct gtg ttg agt cac ccg gca gtt tcc tgc   1105
Glu Trp Cys Ser Gln Glu Ala Val Leu Ser His Pro Ala Val Ser Cys
        355                 360                 365 ttc atg tct cac tgc ggt tgg aac tcc acc atg gag gca ctg tcg tct   1153
Phe Met Ser His Cys Gly Trp Asn Ser Thr Met Glu Ala Leu Ser Ser
    370                 375                 380 ggt gtt ccg gtg gcg gcg ttt ccc att tgg gga gac cag gtg acg gac   1201
Gly Val Pro Val Ala Ala Phe Pro Ile Trp Gly Asp Gln Val Thr Asp
385                 390                 395                 400 gcc aag ttc ttg gtc gat gag ttt aaa gtt gga att agg atg tgt cga   1249
Ala Lys Phe Leu Val Asp Glu Phe Lys Val Gly Ile Arg Met Cys Arg
                405                 410                 415 ggg gag gct gac att aac aag aag gtg gtt acc agg gaa gag att gcg   1297
Gly Glu Ala Asp Ile Asn Lys Lys Val Val Thr Arg Glu Glu Ile Ala
            420                 425                 430 agg tgt ttg tta gcg gcg aca agt ggg cct aag gcg gag gaa ctt aag   1345
Arg Cys Leu Leu Ala Ala Thr Ser Gly Pro Lys Ala Glu Glu Leu Lys
        435                 440                 445
```

```
agg aat gcg ttg aaa tgg aag aag gcg gcg gca gat tcg gtg ggg gct    1393
Arg Asn Ala Leu Lys Trp Lys Lys Ala Ala Ala Asp Ser Val Gly Ala
    450                 455                 460 ggt ggt tct tcg gac cgg aac tta gaa gag ttt gtt ggc agt att aga    1441
Gly Gly Ser Ser Asp Arg Asn Leu Glu Glu Phe Val Gly Ser Ile Arg
465                 470                 475                 480 aaa gat gtt gtt ggg cac tagttgtacc gtacttttg acttttgtt             1489
Lys Asp Val Val Gly His
                485 gaccggccac tcttcagacg ttgtattacc gacttttaat tcttgtgaat tgaactggta  1549 ttatcattaa aaaaaaaaaa aaaaa                                        1574

<210> SEQ ID NO 16
<211> LENGTH: 486
<212> TYPE: PRT
<213> ORGANISM: Lobelia erinus cv.Riviera Midnight Blue
<220> FEATURE:
<221> NAME/KEY: misc_feature
<223> OTHER INFORMATION: Amino acid sequence of UDP-glucose:
      hydroxycinnamic acid 1-O-glucosyltransferase

<400> SEQUENCE: 16

Met Gly Ser Leu Gln Gly Thr Thr Thr Val Glu Asn Leu Thr His Val
1               5                   10                  15

Phe Leu Val Ser Phe Pro Gly Gln Gly His Val Asn Pro Leu Leu Arg
            20                  25                  30

Leu Gly Lys Ile Leu Ala Phe Lys Gly Leu Leu Val Thr Phe Ser Ala
        35                  40                  45

Pro Glu Met Val Gly Glu Ile Ile Lys Gly Ala Asn Lys Tyr Ile Ser
    50                  55                  60

Asp Asp Glu Leu Thr Pro Ile Gly Asp Gly Met Ile Arg Phe Glu Phe
65                  70                  75                  80

Phe Ser Asp Gly Leu Gly Asn Thr Lys Glu Asp Asn Ser Leu Arg Gly
                85                  90                  95

Asn Met Asp Leu Tyr Met Pro Gln Leu Ala Thr Phe Ala Lys Lys Ser
            100                 105                 110

Leu Ser Glu Ile Leu Ile Lys His Glu Lys His Gly Arg Pro Val Ala
        115                 120                 125

Cys Leu Ile Asn Asn Pro Phe Ile Pro Trp Ile Ser Glu Leu Ala Glu
    130                 135                 140

Glu Phe Asn Ile Pro Ser Ala Val Leu Trp Val Gln Ser Cys Ala Ser
145                 150                 155                 160

Phe Ser Ala Tyr Tyr His Tyr His His Gly Leu Val Pro Phe Pro Thr
                165                 170                 175

Glu Asn Glu Pro Glu Arg Asp Val Gln Leu Pro Asn Met Pro Leu Leu
            180                 185                 190

Lys Tyr Asp Glu Ile Pro Gly Phe Leu Leu Pro Ser Ser Pro Tyr Gly
        195                 200                 205

Phe Leu Arg Arg Ala Ile Leu Gly Gln Phe Lys Leu Leu Ser Lys Pro
    210                 215                 220

Ile Cys Ile Leu Val Glu Ser Phe Gln Glu Leu Glu Asn Asp Cys Ile
225                 230                 235                 240

Asn Tyr Leu Ser Thr Leu Cys Pro Ile Lys Pro Ile Gly Pro Leu Phe
                245                 250                 255

Ser Asn Pro Ser Val Arg Asn Gly Ser Ser Ile Arg Gly Asp Phe Met
            260                 265                 270
```

```
Lys Val Glu Asp Cys Ile Asp Trp Leu Asn Thr Arg Ala Asp Ser Ser
        275                 280                 285

Val Val Tyr Val Ser Phe Gly Ser Ile Val Tyr Val Lys Gln Glu Gln
    290                 295                 300

Ile Thr Glu Ile Ala Arg Gly Leu Ala Asp Ser Gly Leu Ser Phe Leu
305                 310                 315                 320

Trp Ala Phe Lys Gln Pro Gly Ile Asp Met Gly Leu Thr Pro Pro Ser
            325                 330                 335

Leu Pro Asp Gly Phe Leu Glu Val Lys Gly Arg Gly Lys Val Val
                340                 345                 350

Glu Trp Cys Ser Gln Glu Ala Val Leu Ser His Pro Ala Val Ser Cys
            355                 360                 365

Phe Met Ser His Cys Gly Trp Asn Ser Thr Met Glu Ala Leu Ser Ser
    370                 375                 380

Gly Val Pro Val Ala Ala Phe Pro Ile Trp Gly Asp Gln Val Thr Asp
385                 390                 395                 400

Ala Lys Phe Leu Val Asp Glu Phe Lys Val Gly Ile Arg Met Cys Arg
                405                 410                 415

Gly Glu Ala Asp Ile Asn Lys Lys Val Val Thr Arg Glu Glu Ile Ala
            420                 425                 430

Arg Cys Leu Leu Ala Ala Thr Ser Gly Pro Lys Ala Glu Glu Leu Lys
    435                 440                 445

Arg Asn Ala Leu Lys Trp Lys Lys Ala Ala Ala Asp Ser Val Gly Ala
    450                 455                 460

Gly Gly Ser Ser Asp Arg Asn Leu Glu Glu Phe Val Gly Ser Ile Arg
465                 470                 475                 480

Lys Asp Val Val Gly His
                485
```

<210> SEQ ID NO 17
<211> LENGTH: 1700
<212> TYPE: DNA
<213> ORGANISM: Lobelia erinus cv.Riviera Midnight Blue
<220> FEATURE:
<221> NAME/KEY: CDS
<222> LOCATION: (2)..(1459)
<223> OTHER INFORMATION: Nucleotide sequence of gene coding for
      UDP-glucose:hydroxycinnamic acid 1-O-glucosyltransferase

<400> SEQUENCE: 17

```
g atg ggc tca ctg cag ggt act act acc gtt gaa aat ctc acc cat gtc        49
  Met Gly Ser Leu Gln Gly Thr Thr Thr Val Glu Asn Leu Thr His Val
  1               5                   10                  15 ttc cta gta tct ttc ccc ggt caa ggc cac gtc aac ccc ctc ctc cgt         97
Phe Leu Val Ser Phe Pro Gly Gln Gly His Val Asn Pro Leu Leu Arg
            20                  25                  30 ctg ggc aag att ctt gcc tcc aag ggc ctc tta gta acc ttc tcc gcc        145
Leu Gly Lys Ile Leu Ala Ser Lys Gly Leu Leu Val Thr Phe Ser Ala
        35                  40                  45 cca gaa atg gtg ggt gaa atc ata aaa ggc gcc aac aag tac atc tcc        193
Pro Glu Met Val Gly Glu Ile Ile Lys Gly Ala Asn Lys Tyr Ile Ser
    50                  55                  60 gac gac gag ctc act ccc atc ggc gac ggc atg atc cgc ttc gag ttc        241
Asp Asp Glu Leu Thr Pro Ile Gly Asp Gly Met Ile Arg Phe Glu Phe
65                  70                  75                  80 ttc tcc gac agt ctt ggc aac acc aaa gag gac aac gct ttg cgc ggc        289
Phe Ser Asp Ser Leu Gly Asn Thr Lys Glu Asp Asn Ala Leu Arg Gly
                85                  90                  95
```

```
aac atg gat ctt tat atg ccc caa cta gct acc ttt gcc aag aag tcg      337
Asn Met Asp Leu Tyr Met Pro Gln Leu Ala Thr Phe Ala Lys Lys Ser
        100                 105                 110 ctc tcc gac atc ctt gta aag cac caa cac cat ggc cgc ccc gtc gcc      385
Leu Ser Asp Ile Leu Val Lys His Gln His His Gly Arg Pro Val Ala
        115                 120                 125 tgc ctt atc aac aac cca ttt atc cct tgg att tcg gag tta gcc gaa      433
Cys Leu Ile Asn Asn Pro Phe Ile Pro Trp Ile Ser Glu Leu Ala Glu
130                 135                 140 gag ttt aac atc cct tct gcc gtt ctg tgg gtt caa tct tgt gct tct      481
Glu Phe Asn Ile Pro Ser Ala Val Leu Trp Val Gln Ser Cys Ala Ser
145                 150                 155                 160 ttt tca gct tat tat cac tac cac cat aat ctt gtc cct ttt ccg acg      529
Phe Ser Ala Tyr Tyr His Tyr His His Asn Leu Val Pro Phe Pro Thr
                165                 170                 175 gaa aac gag ccg gag cgt gat gtt cag ctc cca agc atg cca ttg ttg      577
Glu Asn Glu Pro Glu Arg Asp Val Gln Leu Pro Ser Met Pro Leu Leu
        180                 185                 190 aag tac gat gag atc cct ggc ttc tta ctc cct tcc agt ccg tac ggc      625
Lys Tyr Asp Glu Ile Pro Gly Phe Leu Leu Pro Ser Ser Pro Tyr Gly
        195                 200                 205 ttc ttg agg agg gct att ttg ggt cag ttc aaa ctt ttg tct aaa cca      673
Phe Leu Arg Arg Ala Ile Leu Gly Gln Phe Lys Leu Leu Ser Lys Pro
210                 215                 220 ata tgc att tta gtt gaa tct ttt caa gaa ctg gaa gat gat tgc att      721
Ile Cys Ile Leu Val Glu Ser Phe Gln Glu Leu Glu Asp Asp Cys Ile
225                 230                 235                 240 aat tac tta tct acc ctc tgc ccc att aaa ccc att ggc cca tta ttc      769
Asn Tyr Leu Ser Thr Leu Cys Pro Ile Lys Pro Ile Gly Pro Leu Phe
                245                 250                 255 atc aac ccg aat gtc aaa acc ggg tcc tcc att cga gga gac ttt atg      817
Ile Asn Pro Asn Val Lys Thr Gly Ser Ser Ile Arg Gly Asp Phe Met
        260                 265                 270 aaa gtt gag gac tgt att gat tgg ctt aac acc aga gct gac tcc tct      865
Lys Val Glu Asp Cys Ile Asp Trp Leu Asn Thr Arg Ala Asp Ser Ser
        275                 280                 285 gtt gtg tac atc tct ttc ggg agt att gtt tac gtg aag cag gag cag      913
Val Val Tyr Ile Ser Phe Gly Ser Ile Val Tyr Val Lys Gln Glu Gln
290                 295                 300 att act gaa ata gct cgt ggg ctt gcg gac tcg ggc ctt tct ttt tta      961
Ile Thr Glu Ile Ala Arg Gly Leu Ala Asp Ser Gly Leu Ser Phe Leu
305                 310                 315                 320 tgg gct ttt aaa cag ccc ggt gta gat atg ggc ctt aag cca cct tca     1009
Trp Ala Phe Lys Gln Pro Gly Val Asp Met Gly Leu Lys Pro Pro Ser
                325                 330                 335 tta ccg gac gga ttc ttg gag gag gtg aag ggg agg ggg aaa gta gtg     1057
Leu Pro Asp Gly Phe Leu Glu Glu Val Lys Gly Arg Gly Lys Val Val
        340                 345                 350 gag tgg tgt tcg cag gag gcg gta ttg gga cac ccg gcg gtt tct tgc     1105
Glu Trp Cys Ser Gln Glu Ala Val Leu Gly His Pro Ala Val Ser Cys
        355                 360                 365 ttc atg tct cac tgc ggc tgg aac tcc acc atg gag gcg ctg tcg tct     1153
Phe Met Ser His Cys Gly Trp Asn Ser Thr Met Glu Ala Leu Ser Ser
370                 375                 380 ggg gtt ccg gtg gcg gcg ttt cct att tgg ggt gac caa gtg acg gac     1201
Gly Val Pro Val Ala Ala Phe Pro Ile Trp Gly Asp Gln Val Thr Asp
385                 390                 395                 400 gct aag ttc ttg gtg gac gag ttt aaa gtt ggg att agg atg tgc cga     1249
Ala Lys Phe Leu Val Asp Glu Phe Lys Val Gly Ile Arg Met Cys Arg
                405                 410                 415
```

```
ggg gag gct gac att aac aag aag gtg gtt ccc agg gaa gag att gcg     1297
Gly Glu Ala Asp Ile Asn Lys Lys Val Val Pro Arg Glu Glu Ile Ala
            420                 425                 430 agg tgt ttg tta gcg gcg aca agt ggg ccc aag gcg gag gaa ctt agg     1345
Arg Cys Leu Leu Ala Ala Thr Ser Gly Pro Lys Ala Glu Glu Leu Arg
    435                 440                 445 agg aac gcg ttg aaa tgg aag aag gcg gcg gca gat tcg gtg ggg gct     1393
Arg Asn Ala Leu Lys Trp Lys Lys Ala Ala Ala Asp Ser Val Gly Ala
450                 455                 460 ggt ggt tct tcc gac cgg aac tta gaa gag ttt gtt ggc agt att aaa     1441
Gly Gly Ser Ser Asp Arg Asn Leu Glu Glu Phe Val Gly Ser Ile Lys
465                 470                 475                 480 aaa ggt gtt att ggg cac tagttgtacc gtgtactctt tgttgaccg             1489
Lys Gly Val Ile Gly His
                485 gccacccctt tagacgttgt attacccaca tttatttctt gtgaatcgaa ttggtttatt    1549 atctgtaata tcggctttat gactttacgg agatatgatt ggttttgtga ttttggcttt   1609 gtatgccgat tctaaatatc ttagggaaat aattatattt aaatcaaata gaaatttata   1669 aaataaaaaa aaaaaaaaaa aaaaaaaaaa a                                  1700

<210> SEQ ID NO 18
<211> LENGTH: 486
<212> TYPE: PRT
<213> ORGANISM: Lobelia erinus cv.Riviera Midnight Blue
<220> FEATURE:
<221> NAME/KEY: misc_feature
<223> OTHER INFORMATION: Amino acid sequence of UDP-glucose:
      hydroxycinnamic acid 1-O-glucosyltransferase

<400> SEQUENCE: 18

Met Gly Ser Leu Gln Gly Thr Thr Thr Val Glu Asn Leu Thr His Val
1               5                   10                  15

Phe Leu Val Ser Phe Pro Gly Gln Gly His Val Asn Pro Leu Leu Arg
            20                  25                  30

Leu Gly Lys Ile Leu Ala Ser Lys Gly Leu Leu Val Thr Phe Ser Ala
        35                  40                  45

Pro Glu Met Val Gly Glu Ile Ile Lys Gly Ala Asn Lys Tyr Ile Ser
    50                  55                  60

Asp Asp Glu Leu Thr Pro Ile Gly Asp Gly Met Ile Arg Phe Glu Phe
65                  70                  75                  80

Phe Ser Asp Ser Leu Gly Asn Thr Lys Glu Asp Asn Ala Leu Arg Gly
                85                  90                  95

Asn Met Asp Leu Tyr Met Pro Gln Leu Ala Thr Phe Ala Lys Lys Ser
            100                 105                 110

Leu Ser Asp Ile Leu Val Lys His Gln His Gly Arg Pro Val Ala
        115                 120                 125

Cys Leu Ile Asn Asn Pro Phe Ile Pro Trp Ile Ser Glu Leu Ala Glu
    130                 135                 140

Glu Phe Asn Ile Pro Ser Ala Val Leu Trp Val Gln Ser Cys Ala Ser
145                 150                 155                 160

Phe Ser Ala Tyr Tyr His Tyr His His Asn Leu Val Pro Phe Pro Thr
                165                 170                 175

Glu Asn Glu Pro Glu Arg Asp Val Gln Leu Pro Ser Met Pro Leu Leu
            180                 185                 190

Lys Tyr Asp Glu Ile Pro Gly Phe Leu Leu Pro Ser Ser Pro Tyr Gly
        195                 200                 205
```

```
Phe Leu Arg Arg Ala Ile Leu Gly Gln Phe Lys Leu Leu Ser Lys Pro
    210                 215                 220

Ile Cys Ile Leu Val Glu Ser Phe Gln Glu Leu Glu Asp Asp Cys Ile
225                 230                 235                 240

Asn Tyr Leu Ser Thr Leu Cys Pro Ile Lys Pro Ile Gly Pro Leu Phe
                245                 250                 255

Ile Asn Pro Asn Val Lys Thr Gly Ser Ser Ile Arg Gly Asp Phe Met
            260                 265                 270

Lys Val Glu Asp Cys Ile Asp Trp Leu Asn Thr Arg Ala Asp Ser Ser
        275                 280                 285

Val Val Tyr Ile Ser Phe Gly Ser Ile Val Tyr Val Lys Gln Glu Gln
    290                 295                 300

Ile Thr Glu Ile Ala Arg Gly Leu Ala Asp Ser Gly Leu Ser Phe Leu
305                 310                 315                 320

Trp Ala Phe Lys Gln Pro Gly Val Asp Met Gly Leu Lys Pro Pro Ser
                325                 330                 335

Leu Pro Asp Gly Phe Leu Glu Glu Val Lys Gly Arg Gly Lys Val Val
            340                 345                 350

Glu Trp Cys Ser Gln Glu Ala Val Leu Gly His Pro Ala Val Ser Cys
        355                 360                 365

Phe Met Ser His Cys Gly Trp Asn Ser Thr Met Glu Ala Leu Ser Ser
    370                 375                 380

Gly Val Pro Val Ala Ala Phe Pro Ile Trp Gly Asp Gln Val Thr Asp
385                 390                 395                 400

Ala Lys Phe Leu Val Asp Glu Phe Lys Val Gly Ile Arg Met Cys Arg
                405                 410                 415

Gly Glu Ala Asp Ile Asn Lys Lys Val Val Pro Arg Glu Glu Ile Ala
            420                 425                 430

Arg Cys Leu Leu Ala Ala Thr Ser Gly Pro Lys Ala Glu Glu Leu Arg
        435                 440                 445

Arg Asn Ala Leu Lys Trp Lys Lys Ala Ala Ala Asp Ser Val Gly Ala
    450                 455                 460

Gly Gly Ser Ser Asp Arg Asn Leu Glu Glu Phe Val Gly Ser Ile Lys
465                 470                 475                 480

Lys Gly Val Ile Gly His
                485

<210> SEQ ID NO 19
<211> LENGTH: 8
<212> TYPE: PRT
<213> ORGANISM: Clitoria ternatea cv. Double Blue

<400> SEQUENCE: 19

Arg Trp Leu Ile Asp His Pro Lys
1               5

<210> SEQ ID NO 20
<211> LENGTH: 8
<212> TYPE: PRT
<213> ORGANISM: Clitoria ternatea cv. Double Blue

<400> SEQUENCE: 20

Lys Trp Leu Ile Asp His Pro Lys
1               5
```

```
<210> SEQ ID NO 21
<211> LENGTH: 10
<212> TYPE: PRT
<213> ORGANISM: Clitoria ternatea cv. Double Blue

<400> SEQUENCE: 21

Arg Ile Ser Phe Ala His Ile Leu Glu Arg
1               5                   10

<210> SEQ ID NO 22
<211> LENGTH: 10
<212> TYPE: PRT
<213> ORGANISM: Clitoria ternatea cv. Double Blue

<400> SEQUENCE: 22

Lys Ile Ser Phe Ala His Ile Leu Glu Arg
1               5                   10

<210> SEQ ID NO 23
<211> LENGTH: 10
<212> TYPE: PRT
<213> ORGANISM: Clitoria ternatea cv. Double Blue
<220> FEATURE:
<221> NAME/KEY: UNSURE
<222> LOCATION: (7)..(7)
<223> OTHER INFORMATION: Xaa represents an undetermined amino acid

<400> SEQUENCE: 23

Arg Arg Pro Leu Tyr Glu Xaa Asn Thr Met
1               5                   10

<210> SEQ ID NO 24
<211> LENGTH: 10
<212> TYPE: PRT
<213> ORGANISM: Clitoria ternatea cv. Double Blue
<220> FEATURE:
<221> NAME/KEY: UNSURE
<222> LOCATION: (7)..(7)
<223> OTHER INFORMATION: Xaa represents an undetermined amino acid

<400> SEQUENCE: 24

Lys Arg Pro Leu Tyr Glu Xaa Asn Thr Met
1               5                   10

<210> SEQ ID NO 25
<211> LENGTH: 27
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (22)..(22)
<223> OTHER INFORMATION: n represents inosine
<220> FEATURE:
<221> NAME/KEY: modified_base
<222> LOCATION: (25)..(25)
<223> OTHER INFORMATION: n represents inosine

<400> SEQUENCE: 25
ggaccccgtg atgatctggy tnamngg                                      27

<210> SEQ ID NO 26
<211> LENGTH: 26
<212> TYPE: DNA
<213> ORGANISM: Artificial Sequence
<220> FEATURE:
<223> OTHER INFORMATION: Synthetic primer
```

```
<220> FEATURE:
<221> NAME/KEY: modified_base
<222> LOCATION: (18)..(18)
<223> OTHER INFORMATION: n represents inosine
<220> FEATURE:
<221> NAME/KEY: modified_base
<222> LOCATION: (21)..(21)
<223> OTHER INFORMATION: n represents inosine
<220> FEATURE:
<221> NAME/KEY: modified_base
<222> LOCATION: (24)..(24)
<223> OTHER INFORMATION: n represents inosine

<400> SEQUENCE: 26
ccgcagaagc aggagcancc nggncc                                        26

<210> SEQ ID NO 27
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (3)..(3)
<223> OTHER INFORMATION: n represents inosine
<220> FEATURE:
<221> NAME/KEY: modified_base
<222> LOCATION: (9)..(9)
<223> OTHER INFORMATION: n represents inosine
<220> FEATURE:
<221> NAME/KEY: modified_base
<222> LOCATION: (15)..(15)
<223> OTHER INFORMATION: n represents inosine
<220> FEATURE:
<221> NAME/KEY: modified_base
<222> LOCATION: (21)..(21)
<223> OTHER INFORMATION: n represents inosine

<400> SEQUENCE: 27
amnggwggnc ctggntgyws nws                                           23

<210> SEQ ID NO 28
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (3)..(3)
<223> OTHER INFORMATION: n represents inosine
<220> FEATURE:
<221> NAME/KEY: modified_base
<222> LOCATION: (6)..(6)
<223> OTHER INFORMATION: n represents inosine
<220> FEATURE:
<221> NAME/KEY: modified_base
<222> LOCATION: (9)..(9)
<223> OTHER INFORMATION: n represents inosine
<220> FEATURE:
<221> NAME/KEY: modified_base
<222> LOCATION: (12)..(12)
<223> OTHER INFORMATION: n represents inosine
<220> FEATURE:
<221> NAME/KEY: modified_base
<222> LOCATION: (15)..(15)
<223> OTHER INFORMATION: n represents inosine
<220> FEATURE:
<221> NAME/KEY: modified_base
<222> LOCATION: (18)..(18)
<223> OTHER INFORMATION: n represents inosine

<400> SEQUENCE: 28
ganwsnccng ynggnwsngg                                               20
```

```
<210> SEQ ID NO 29
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (3)..(3)
<223> OTHER INFORMATION: n represents inosine
<220> FEATURE:
<221> NAME/KEY: modified_base
<222> LOCATION: (6)..(6)
<223> OTHER INFORMATION: n represents inosine
<220> FEATURE:
<221> NAME/KEY: modified_base
<222> LOCATION: (9)..(9)
<223> OTHER INFORMATION: n represents inosine
<220> FEATURE:
<221> NAME/KEY: modified_base
<222> LOCATION: (12)..(12)
<223> OTHER INFORMATION: n represents inosine
<220> FEATURE:
<221> NAME/KEY: modified_base
<222> LOCATION: (15)..(15)
<223> OTHER INFORMATION: n represents inosine
<220> FEATURE:
<221> NAME/KEY: modified_base
<222> LOCATION: (21)..(21)
<223> OTHER INFORMATION: n represents inosine

<400> SEQUENCE: 29
rtngsnggng anwsntayds ngg                                             23

<210> SEQ ID NO 30
<211> LENGTH: 18
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (10)..(10)
<223> OTHER INFORMATION: n represents inosine
<220> FEATURE:
<221> NAME/KEY: modified_base
<222> LOCATION: (13)..(13)
<223> OTHER INFORMATION: n represents inosine

<400> SEQUENCE: 30
rtcrtgrtcn ccnswrwa                                                   18

<210> SEQ ID NO 31
<211> LENGTH: 26
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (12)..(12)
<223> OTHER INFORMATION: n represents inosine
<220> FEATURE:
<221> NAME/KEY: modified_base
<222> LOCATION: (15)..(15)
<223> OTHER INFORMATION: n represents inosine
<220> FEATURE:
<221> NAME/KEY: modified_base
<222> LOCATION: (18)..(18)
<223> OTHER INFORMATION: n represents inosine
<220> FEATURE:
<221> NAME/KEY: modified_base
<222> LOCATION: (24)..(24)
<223> OTHER INFORMATION: n represents inosine
```

```
<400> SEQUENCE: 31
ggyttrtayt cnggnrcngt rtgncc                                26

<210> SEQ ID NO 32
<211> LENGTH: 21
<212> TYPE: DNA
<213> ORGANISM: Artificial Sequence
<220> FEATURE:
<223> OTHER INFORMATION: Synthetic primer

<400> SEQUENCE: 32
tggaagaatt cgcggccgca g                                     21

<210> SEQ ID NO 33
<211> LENGTH: 23
<212> TYPE: DNA
<213> ORGANISM: Artificial Sequence
<220> FEATURE:
<223> OTHER INFORMATION: Synthetic primer

<400> SEQUENCE: 33
cgactggagc acgaggacac tga                                   23

<210> SEQ ID NO 34
<211> LENGTH: 26
<212> TYPE: DNA
<213> ORGANISM: Artificial Sequence
<220> FEATURE:
<223> OTHER INFORMATION: Synthetic primer

<400> SEQUENCE: 34
tactggaatg ggaataccag agtaag                                26

<210> SEQ ID NO 35
<211> LENGTH: 26
<212> TYPE: DNA
<213> ORGANISM: Artificial Sequence
<220> FEATURE:
<223> OTHER INFORMATION: Synthetic primer

<400> SEQUENCE: 35
ggcatggtga actaatgtcc agtcac                                26

<210> SEQ ID NO 36
<211> LENGTH: 22
<212> TYPE: DNA
<213> ORGANISM: Artificial Sequence
<220> FEATURE:
<223> OTHER INFORMATION: Synthetic primer

<400> SEQUENCE: 36
gtgtcgaccc agtcacagtt tg                                    22

<210> SEQ ID NO 37
<211> LENGTH: 26
<212> TYPE: DNA
<213> ORGANISM: Artificial Sequence
<220> FEATURE:
<223> OTHER INFORMATION: Synthetic primer

<400> SEQUENCE: 37
ctgatataac ctcattgtat gactcc                                26
```

```
<210> SEQ ID NO 38
<211> LENGTH: 25
<212> TYPE: DNA
<213> ORGANISM: Artificial Sequence
<220> FEATURE:
<223> OTHER INFORMATION: Synthetic primer

<400> SEQUENCE: 38
gctgtcaacg atacgctacg taacg                                         25

<210> SEQ ID NO 39
<211> LENGTH: 23
<212> TYPE: DNA
<213> ORGANISM: Artificial Sequence
<220> FEATURE:
<223> OTHER INFORMATION: Synthetic primer

<400> SEQUENCE: 39
cgctacgtaa cggcatgaca gtg                                           23

<210> SEQ ID NO 40
<211> LENGTH: 26
<212> TYPE: DNA
<213> ORGANISM: Artificial Sequence
<220> FEATURE:
<223> OTHER INFORMATION: Synthetic primer

<400> SEQUENCE: 40
tcataaggga agtattggtg aatggc                                        26

<210> SEQ ID NO 41
<211> LENGTH: 25
<212> TYPE: DNA
<213> ORGANISM: Artificial Sequence
<220> FEATURE:
<223> OTHER INFORMATION: Synthetic primer

<400> SEQUENCE: 41
gtttaccttt cacgtcggac attcc                                         25

<210> SEQ ID NO 42
<211> LENGTH: 22
<212> TYPE: DNA
<213> ORGANISM: Artificial Sequence
<220> FEATURE:
<223> OTHER INFORMATION: Synthetic primer

<400> SEQUENCE: 42
agtgcactac acattcgtaa gg                                            22

<210> SEQ ID NO 43
<211> LENGTH: 21
<212> TYPE: DNA
<213> ORGANISM: Artificial Sequence
<220> FEATURE:
<223> OTHER INFORMATION: Synthetic primer

<400> SEQUENCE: 43
gtaaatggcg tcgatgtacc c                                             21

<210> SEQ ID NO 44
<211> LENGTH: 37
<212> TYPE: DNA
<213> ORGANISM: Artificial Sequence
<220> FEATURE:
<223> OTHER INFORMATION: Synthetic primer
```

```
<400> SEQUENCE: 44
gacgacgaca agatgaccat agtagagttc cttcctg                               37

<210> SEQ ID NO 45
<211> LENGTH: 40
<212> TYPE: DNA
<213> ORGANISM: Artificial Sequence
<220> FEATURE:
<223> OTHER INFORMATION: Synthetic primer

<400> SEQUENCE: 45
gaggagaagc ccggttatta tagaatggat gccaagttgg                            40

<210> SEQ ID NO 46
<211> LENGTH: 17
<212> TYPE: DNA
<213> ORGANISM: Artificial Sequence
<220> FEATURE:
<223> OTHER INFORMATION: Synthetic primer

<400> SEQUENCE: 46
attaaaaaaa aaatatg                                                    17

<210> SEQ ID NO 47
<211> LENGTH: 29
<212> TYPE: DNA
<213> ORGANISM: Artificial Sequence
<220> FEATURE:
<223> OTHER INFORMATION: Synthetic primer

<400> SEQUENCE: 47
caccatggca gccttcagtt caactcata                                       29

<210> SEQ ID NO 48
<211> LENGTH: 26
<212> TYPE: DNA
<213> ORGANISM: Artificial Sequence
<220> FEATURE:
<223> OTHER INFORMATION: Synthetic primer

<400> SEQUENCE: 48
tagaatggat gccaagttgg tgtatg                                          26

<210> SEQ ID NO 49
<211> LENGTH: 29
<212> TYPE: DNA
<213> ORGANISM: Artificial Sequence
<220> FEATURE:
<223> OTHER INFORMATION: Synthetic primer

<400> SEQUENCE: 49
caccatggcg aggtttagtt caagtcttg                                       29

<210> SEQ ID NO 50
<211> LENGTH: 29
<212> TYPE: DNA
<213> ORGANISM: Artificial Sequence
<220> FEATURE:
<223> OTHER INFORMATION: Synthetic primer

<400> SEQUENCE: 50
ttacaaaggc cttttagata tccatctcc                                       29
```

```
<210> SEQ ID NO 51
<211> LENGTH: 25
<212> TYPE: DNA
<213> ORGANISM: Artificial Sequence
<220> FEATURE:
<223> OTHER INFORMATION: Synthetic primer

<400> SEQUENCE: 51
gcataaaccg ttgctttgat ccgcc                                          25

<210> SEQ ID NO 52
<211> LENGTH: 25
<212> TYPE: DNA
<213> ORGANISM: Artificial Sequence
<220> FEATURE:
<223> OTHER INFORMATION: Synthetic primer

<400> SEQUENCE: 52
catcaatgaa gccatcagcc acagg                                          25

<210> SEQ ID NO 53
<211> LENGTH: 24
<212> TYPE: DNA
<213> ORGANISM: Artificial Sequence
<220> FEATURE:
<223> OTHER INFORMATION: Synthetic primer

<400> SEQUENCE: 53
ttaagcacgt caggaatccg gagg                                           24

<210> SEQ ID NO 54
<211> LENGTH: 25
<212> TYPE: DNA
<213> ORGANISM: Artificial Sequence
<220> FEATURE:
<223> OTHER INFORMATION: Synthetic primer

<400> SEQUENCE: 54
tgaacgtcga atgccgtgaa acacc                                          25

<210> SEQ ID NO 55
<211> LENGTH: 24
<212> TYPE: DNA
<213> ORGANISM: Artificial Sequence
<220> FEATURE:
<223> OTHER INFORMATION: Synthetic primer

<400> SEQUENCE: 55
tggcatacag tggcgaccat gatc                                           24

<210> SEQ ID NO 56
<211> LENGTH: 24
<212> TYPE: DNA
<213> ORGANISM: Artificial Sequence
<220> FEATURE:
<223> OTHER INFORMATION: Synthetic primer

<400> SEQUENCE: 56
ctgatgagtg gcgtccatgg aaag                                           24

<210> SEQ ID NO 57
<211> LENGTH: 25
<212> TYPE: DNA
<213> ORGANISM: Artificial Sequence
<220> FEATURE:
<223> OTHER INFORMATION: Synthetic primer
```

```
<400> SEQUENCE: 57
cgttgtaacc gttcgttgcc attcg                                           25

<210> SEQ ID NO 58
<211> LENGTH: 24
<212> TYPE: DNA
<213> ORGANISM: Artificial Sequence
<220> FEATURE:
<223> OTHER INFORMATION: Synthetic primer

<400> SEQUENCE: 58
cgatggtgcc attcatggct actc                                            24

<210> SEQ ID NO 59
<211> LENGTH: 24
<212> TYPE: DNA
<213> ORGANISM: Artificial Sequence
<220> FEATURE:
<223> OTHER INFORMATION: Synthetic primer

<400> SEQUENCE: 59
caccatggcg gtgccggcgg tgcc                                            24

<210> SEQ ID NO 60
<211> LENGTH: 28
<212> TYPE: DNA
<213> ORGANISM: Artificial Sequence
<220> FEATURE:
<223> OTHER INFORMATION: Synthetic primer

<400> SEQUENCE: 60
caccatggcg gatacaaacg gcacagcc                                        28

<210> SEQ ID NO 61
<211> LENGTH: 24
<212> TYPE: DNA
<213> ORGANISM: Artificial Sequence
<220> FEATURE:
<223> OTHER INFORMATION: Synthetic primer

<400> SEQUENCE: 61
caatggagaa tccgagaaaa accg                                            24

<210> SEQ ID NO 62
<211> LENGTH: 27
<212> TYPE: DNA
<213> ORGANISM: Artificial Sequence
<220> FEATURE:
<223> OTHER INFORMATION: Synthetic primer

<400> SEQUENCE: 62
ttacaatgga gaatccgaga aaaaccg                                         27

<210> SEQ ID NO 63
<211> LENGTH: 23
<212> TYPE: DNA
<213> ORGANISM: Artificial Sequence
<220> FEATURE:
<223> OTHER INFORMATION: Synthetic primer

<400> SEQUENCE: 63
caacggttta tgagttatcc acc                                             23
```

<210> SEQ ID NO 64
<211> LENGTH: 25
<212> TYPE: DNA
<213> ORGANISM: Artificial Sequence
<220> FEATURE:
<223> OTHER INFORMATION: Synthetic primer

<400> SEQUENCE: 64
ctacaacggt ttatgagtta tccac                                           25

<210> SEQ ID NO 65
<211> LENGTH: 24
<212> TYPE: DNA
<213> ORGANISM: Artificial Sequence
<220> FEATURE:
<223> OTHER INFORMATION: Synthetic primer

<400> SEQUENCE: 65
aatgggttgc ctagcacgta tccc                                            24

<210> SEQ ID NO 66
<211> LENGTH: 25
<212> TYPE: DNA
<213> ORGANISM: Artificial Sequence
<220> FEATURE:
<223> OTHER INFORMATION: Synthetic primer

<400> SEQUENCE: 66
gattcgtgtt tggcatctgt ccagc                                           25

<210> SEQ ID NO 67
<211> LENGTH: 24
<212> TYPE: DNA
<213> ORGANISM: Artificial Sequence
<220> FEATURE:
<223> OTHER INFORMATION: Synthetic primer

<400> SEQUENCE: 67
aacgagccag ttgtccaaca agcc                                            24

<210> SEQ ID NO 68
<211> LENGTH: 26
<212> TYPE: DNA
<213> ORGANISM: Artificial Sequence
<220> FEATURE:
<223> OTHER INFORMATION: Synthetic primer

<400> SEQUENCE: 68
ctccacgtac gaaagggaac actaac                                          26

<210> SEQ ID NO 69
<211> LENGTH: 28
<212> TYPE: DNA
<213> ORGANISM: Artificial Sequence
<220> FEATURE:
<223> OTHER INFORMATION: Synthetic primer

<400> SEQUENCE: 69
caccatggcg tttggtatgc cattttcg                                        28

<210> SEQ ID NO 70
<211> LENGTH: 26
<212> TYPE: DNA
<213> ORGANISM: Artificial Sequence
<220> FEATURE:
<223> OTHER INFORMATION: Synthetic primer

```
<400> SEQUENCE: 70
caataaacta cgagtaagcc accttc                                         26

<210> SEQ ID NO 71
<211> LENGTH: 25
<212> TYPE: DNA
<213> ORGANISM: Artificial Sequence
<220> FEATURE:
<223> OTHER INFORMATION: Synthetic primer

<400> SEQUENCE: 71
tcacaataaa ctacgagtaa gccac                                          25

<210> SEQ ID NO 72
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (3)..(3)
<223> OTHER INFORMATION: n represents inosine
<220> FEATURE:
<221> NAME/KEY: modified_base
<222> LOCATION: (12)..(12)
<223> OTHER INFORMATION: n represents inosine

<400> SEQUENCE: 72 wncaytgyg gntggaaytc                                                 20

<210> SEQ ID NO 73
<211> LENGTH: 34
<212> TYPE: DNA
<213> ORGANISM: Artificial Sequence
<220> FEATURE:
<223> OTHER INFORMATION: Synthetic primer

<400> SEQUENCE: 73
gacgacgaca agatggggtc tgaagcttcg tttc                                34

<210> SEQ ID NO 74
<211> LENGTH: 35
<212> TYPE: DNA
<213> ORGANISM: Artificial Sequence
<220> FEATURE:
<223> OTHER INFORMATION: Synthetic primer

<400> SEQUENCE: 74
gaggagaagc ccggtctaag ggttaccacg gtttc                               35

<210> SEQ ID NO 75
<211> LENGTH: 42
<212> TYPE: DNA
<213> ORGANISM: Artificial Sequence
<220> FEATURE:
<223> OTHER INFORMATION: Synthetic primer

<400> SEQUENCE: 75
gacgacgaca agatgggctc actgcagggt actactaccg tc                       42

<210> SEQ ID NO 76
<211> LENGTH: 37
<212> TYPE: DNA
<213> ORGANISM: Artificial Sequence
<220> FEATURE:
<223> OTHER INFORMATION: Synthetic primer
```

```
-continued

<400> SEQUENCE: 76
gaggagaagc ccggttagtg cccaacaaca tcttttc                              37

<210> SEQ ID NO 77
<211> LENGTH: 42
<212> TYPE: DNA
<213> ORGANISM: Artificial Sequence
<220> FEATURE:
<223> OTHER INFORMATION: Synthetic primer

<400> SEQUENCE: 77
gacgacgaca agatgggctc actgcagggt actactaccg tt                        42

<210> SEQ ID NO 78
<211> LENGTH: 37
<212> TYPE: DNA
<213> ORGANISM: Artificial Sequence
<220> FEATURE:
<223> OTHER INFORMATION: Synthetic primer

<400> SEQUENCE: 78
gaggagaagc ccggttagtg cccaataaca cctttt                               37
```

AROMATIC ACYLTRANSFERASE GENES

TECHNICAL FIELD

The present invention relates to a gene encoding a protein having an activity of transferring an aromatic acyl group to sugar residue of flavonoid using 1-O-acyl-β-D-glucose as an acyl donor; a gene encoding a protein that has an activity of transferring a glucosyl group to a hydroxyl group at position 1 of hydroxycinnamic acid using UDP-glucose as a glucosyl donor; and a method of using the same.

BACKGROUND ART

Plant color is one of the most important characters from an industrial viewpoint. As seen from pursuit of diversified flower colors, good expression of fruit colors, stabilization and uniformity of expressed colors, and so on, plant color is a big economical factor in flowers and ornamental plant, fruit trees and vegetables. Among plant pigments, the most abundantly seen are compounds generically termed anthocyanin. Cells and tissues where anthocyanin is accumulated present various colors from light blue to dark red. To date, almost 500 types of anthocyanin have been reported from various plant species, and their colors are mainly depending on the chemical structures thereof. Anthocyanidin (an aglycone that is the skeleton of anthocyanin) does not exist in plant bodies as it is, but exists in a modified form which has undergone glucosylation or acylation. Through glucosylation, anthocyanidin becomes nontoxic anthocyanin and stabilized; also, it becomes water-soluble and dissolved in cell vacuoles. A large number of glycosylated anthocyanins undergo further modification such as glycosylation, acylation or methylation. In particular, acylation increases the stability of anthocyanin molecules in vacuoles. Acylation by an aromatic acyl group bathochromically shifts the UV/visible absorption maximum of anthocyanins as a result of intramolecular association of the aglycone and the aromatic acyl group(s). Therefore, plant tissues with accumulation of acylated anthocyanin with aromatic acyl groups present a purple to blue color in many occasions. Anthocyanins form complex pigments through intramolecular association with aromatic acyl groups; intermolecular association with co-pigments (such as acylglucose, flavone or flavonol) or metal ions; coordinate bond with metal ions; bond with polypeptides; etc. in vacuoles and presents diversified colors. Therefore, acylation of anthocyanin is one of the important chemical reactions in expanding the diversity of flower colors with anthocyanin.

Color expression with anthocyanin, a character which can be directly confirmed with eyes, has become a target for a great number of genetic, biochemical and molecular biological studies. To date, genes involved in flavonoid including anthocyanin biosynthesis have been cloned from floricultural plants and experimental model plants such as petunia (Petunia x hybrida), snapdragon (Antirrhinum majus), morning glory (Pharbitis nil or Ipomoea nil), Arabidopsis thaliana; fruits such as apple (Malus x domestica), grape (Vitis vinifera); vegetables such as egg plant (Solanum melongena), perilla (Perilla frutescens); and so on. The mechanism of flower color expression with anthocyanin is now being elucidated by analysis by means of natural product chemistry and physiology.

Difference in color expression via accumulation of anthocyanin in plant species such as gentian (Gentiana spp.), prairie gentian (Eustoma grandiflorum), morning glory, lobelia (Lobelia erinus), verbena (Verbena x hybrida) or cineraria (Senecio cruentus or Pericallis cruenta) is basically attributable to difference in the aglycone (pelargonidin, cyanidin, delphinidin, petunidin, malvidin, etc.) of anthocyanin, and it is known that accumulation of delphinidin-type pigments is effective for blue color expression. On the other hand, difference in flower color expression in plants such as petunia, delphinium (Delphinium spp.) or butterfly pea (Clitoria ternatea) is attributable to difference in the binding pattern of sugar and acyl group to anthocyanidin and the number of bonds thereof. Acyl groups do not directly bind to anthocyanin aglycone; in many cases they bind to sugar residues (such as glucose) bound to anthocyanidin. It is reported that the caffeoyl group (an aromatic acyl group) binding to a glucosyl group at position 3' of anthocyanin B ring in Gentiana triflora and the p-coumaroyl group (an aromatic acyl group) binding to glucosyl groups at positions 3' and 5' in butterfly pea and Dianella spp. are intramolecularly associating with anthocyanin aglycone at closer positions than other aromatic acyl groups binding to other glucosyl groups at positions 3, 5, 7, etc. (Yoshida et al., (2000) Phytochemistry 54: 85-92; Terahara et al., (1996) Journal of Natural Products 59: 139-144; Bloor (2001) Phytochemistry 58: 923-927). Therefore, it is reasonably presumed that modification of glucosyl groups at positions 3' and 5' of anthocyanin with aromatic acyl groups will be able to express purple or blue colors in cells, tissues and organs of plants. However, genes to be used for such a purpose have not been isolated yet.

With respect to acylation of anthocyanin, there have been reported acylation with aliphatic acyl groups (such as acetyl, malyl, malonyl, methylmalonyl or succinyl) and acylation with aromatic acyl groups (such as p-coumaroyl, caffeoyl, feruloyl, sinapoyl, p-hydroxybenzoyl or galloyl).

As a gene encoding acylation of anthocyanin sugar residue with an aliphatic acyl group, there is reported a gene encoding a protein having an activity of transferring a malonyl group to a sugar residue at position 3 of flavonoid using an aliphatic acyl-CoA thioester as an acyl donor in dahlia (Dahlia variabilis) (Suzuki et al., (2002) Plant Physiology 13: 2142-2151; Japanese Unexamined Patent Publication No. 2002-233381), cineraria (PCT/WO96/25500; Suzuki et al., (2003) Plant Biotechnology 20: 229-234), chrysanthemum (Dendranthema x morifolium) (Suzuki et al., (2004) Plant Science 166: 89-96) and verbena and deadnettle (Lamium purpureum) (Suzuki et al., (2004) Journal of Molecular Catalysis B: Enzymatic 28: 87-93). Further, a gene encoding a protein having an activity of transferring a malonyl group to a sugar residue at position 5 of flavonoid using aliphatic acyl-CoA thioester as an acyl donor has been reported from Salvia splendens (Suzuki et al., (2001) Journal of Biological Chemistry 276: 49013-49019; Suzuki et al., (2004) Plant Journal 38: 994-1003; PCT/WO01/92536); and Salvia guaranitica, lavender (Lavendula angustifolia) and perilla (PCT/JP01/04677).

Further, as a gene encoding acylation of anthocyanin sugar residue with an aromatic acyl group, there is reported a gene encoding a protein having an activity of transferring an aromatic acyl group to a sugar residue at position 3 of flavonoid using aromatic acyl-CoA thioester as an acyl donor in perilla and lavender (PCT/WO96/125500; Yonekura-Sakakibara et al., (2000) Plant Cell Physiology 41: 495-502) and petunia (PCT/WO01/72984). Still further, a gene encoding a protein having an activity of transferring an aromatic acyl group to a sugar residue at position 5 of flavonoid using an aromatic acyl-CoA thioester as an acyl donor in Gentiana triflora (PCT/WO96/25500; Fujiwara et al., (1998) Plant Journal 16: 421-431) and prairie gentian (Noda et al., (2000) Breeding Research 3 (Supplement 1): 61; Noda et al., (2002) The 20th Annual Meeting of the Japanese Society of Plant Cell and Molecular Biology: Abstract: 145).

Thus, those reported genes and its proteins catalyzes the acyl transfer to the anthocyanin sugar residues using acyl-CoA thioester as acyl-donor. However, it is reported that acyl donors include, in addition to acyl-CoA thioester, chlorogenic acid and 1-$O$-acyl-β-D-glucose (Steffens (2000) Plant Cell 12: 1253-1255).

With respect to proteins having an acyl transfer activity using chlorogenic acid as an acyl donor, purification and biochemical analysis of chlorogenic acid:glucaric acid caffeoyltransferase (5-O-caffeoylquinic acid:glucaric acid caffeoyltransferase) from tomato (*Lycopersicon esculentum*) have been reported (Strack and Gross (1990) Plant Physiology 92: 41-47).

As proteins having an activity of 1-$O$-acyl-β-D-glucose dependent acyltransferase activity, the following reports have been made. With respect to choline sinapoyltransferase involved in 1-$O$-sinapic acid ester metabolism (1-$O$-sinapoyl-β-D-glucose:choline 1-$O$-sinapoyltransferase), partial purification and characterization from seeds of wild radish (*Raphanus sativus*) and white mustard (*Sinapis alba*) (Gräwe and Strack (1986) Zeitschrift für Naturforchung 43c: 28-33); analysis of *Arabidopsis thaliana* mutants and cloning of the gene (Shirley et al., (2001) Plant Journal 28:83-94) and biochemical analysis using a recombinant protein (Shirley and Chapple (2003) Journal of Biological Chemistry 278: 19870-19877); and cloning of SNG2 gene from *Brassica napus* (Milkowski et al., (2004) Plant Journal 38: 80-92) have been reported.

With respect to malate sinapoyltransferase involved in sinapic acid ester metabolism (1-$O$-sinapoyl-β-D-glucose: malate 1-$O$-sinapoyltransferase), localization in *Raphanus sativus* cells (Sharma and Strack (1985) Planta 163: 563-568), measurement of activity in *Brassica napus* seeds and seedlings (Strack et al., (1990) Planta 180: 217-219), measurement of enzyme activity in seedlings and plantlets of *Arabidopsis thaliana* and *Brassica rapa* ssp. *oleifera* (Mock et al., (1992) Zeitschrift für Naturforchung 47c: 680-682), protein purification and biochemical analysis from wild radish hypocotyls (Gräwe et al., (1992) Planta 187: 236-241), analysis of *Arabidopsis thaliana* mutants and cloning of SNG1 gene (Lehfeldt et al., (2000) Plant Cell 12: 1295-1306; PCT/WO02/04614), and localization in cells of leaf tissue in *Arabidopsis thaliana* (Hause et al., (2002) Planta 215: 26-32) have been reported.

With respect to glucose acyltransferase involved in fatty acid metabolism (1-$O$-butyryl-β-D-glucose: 1-$O$-butyryl-β-D-glucose 2-O-butyryltransferase), measurement of enzyme activity in *Lycopercsicon pennellii* (Ghangas and Steffens (1995) Archives of Biochemistry and Biophysics 316: 370-377; Ghangas (1999) Phytochemistry 52: 785-792), purification and determination of partial amino acid sequences (Li et al., (1999) Plant Physiology 121:453-460) and cloning of gene (Li and Steffens (2000) PNAS 97: 6902-6907; PCT/WO97/48811) have been reported.

With respect to 1-$O$-indole-3-acetyl-β-D-glucose:myo-inositol indole-3-acetyltransferase involved in indoleacetic acid metabolism, measurement of enzyme activity from corn (*Zea mays*) (Michalczuk and Bandurski (1980) Biochemical Biophysics Research Communication 93: 588-592), and purification and biochemical analysis of protein and analysis of partial amino acid sequence (Kowalczyk et al., (2003) Physiologia Plantarum 119:165-174) have been reported.

With respect to 1-$O$-hydroxycinnamoyl-β-D-glucose:bethanidine diglucoside O-hydroxycinnamoyltransferase involved in betalain biosynthesis, detection of activity from suspension culture cells of wild spinach (*Chenopodium rubrum*) or petals of *Lampranthus sociorum* (Bokern and Strack (1988) Planta 174:101-105; Bokern et al., (1991) Planta 184: 261-270), and purification of protein and analysis of biochemical properties thereof (Bokern et al., (1992) Botanica Acta 105: 146-151) have been reported.

With respect to β-glucogallin (1-$O$-galloyl-β-D-glucose) dependent galloyltransferase involved in gallotannin biosynthesis, purification of protein and analysis of biochemical properties thereof from Stag's horn sumach (*Rhus typhina*) leaves (Niemetz and Gross (2001) Phytochemistry 58: 657-661; Fröhlich et al., (2002) Planta 216: 168-172) and English oak (*Quercus robur*) leaves (Gross et al., (1986) Journal of Plant Physiology 126: 173-179) have been reported.

As described above, purification of proteins having an activity of catalyzing acyl transfer reaction using 1-$O$-acyl-β-D-glucose as an acyl donor; elucidation of the biochemical properties of such proteins; and cloning of genes encoding such proteins have already been reported. However, with respect to detection of the activity of 1-$O$-acyl-β-D-glucose dependent acyltransferase that transfers an acyl group to sugar residues of flavonoids (such as anthocyanin), there has been only one report about 1-$O$-sinapoyl-β-D-glucose:anthocyanidin triglucoside sinapoyltransferase in cultured cells of carrot (*Daucus carota*) (Glaessgen and Seitz (1992) Planta 186: 582-585). Purification of such a protein with activity or cloning of genes encoding the same has not been performed yet.

[Patent Document 1] Japanese Unexamined Patent Publication No. 2002-233381
[Patent Document 2] PCT/WO 01/92536
[Patent Document 3] PCT/WO 01/72984
[Patent Document 4] PCT/WO 02/04614
[Patent Document 5] PCT/WO 97/48811

DISCLOSURE OF THE INVENTION

Problem for Solution by the Invention

It is an object of the present invention to obtain a gene encoding a protein having an activity of transferring an acyl group to a sugar residue of a flavonoid, preferably, a protein having an activity of transferring an aromatic acyl group to one or more positions of a sugar residue of a flavonoid (inducing anthocyanin) not using acyl-CoA but using 1-$O$-acyl-β-D-glucose as an acyl donor. By introducing the gene obtained by the invention encoding a protein having aromatic acyl transfer activity or a gene similar thereto into a plant and expressing therein, it is possible to modify the types of flavonoid compounds accumulated therein to thereby modify the plant color, such as flower color or fruit color. Further, by regulating gene expression by RNAi method or the like with the gene of the invention and transferring genes encoding known modification enzymes in anthocyanin (such as glucosyltransferase, acyltransferase, methyltransferase), it is possible to allow biosynthesis of non-inherent anthocyanins in various plant species to thereby create plants presenting novel colors.

Means to Solve the Problem

The present inventors have found an enzyme activity in butterfly pea petals that catalyzes a reaction transferring an aromatic acyl group to a sugar residue of anthocyanin using 1-$O$-acyl-β-D-glucose as an acyl donor. Then, the inventors have purified the enzyme and determined a partial amino acid sequences thereof The nucleotide sequences of genes encoding proteins that catalyze reactions using 1-$O$-acyl-β-D-glucose as an acyl donor are highly homologous to the nucleotide sequences of genes encoding serine carboxypeptidase (SCPase). Thus, those proteins that catalyze reactions using 1-O-acyl-β-D-glucose as an acyl donor are called serine carboxypeptidase-like acyltransferase (SCPL-AT) (Milkowski and Strack (2004) Phytochemistry 65: 517-524). Then, the inventors synthesized degenerate primers based on the predicted amino acid sequences and nucleotide sequences existing in common in SCPase and SCPL-AT. Using these primers, RT-PCR was performed to amplify cDNA fragments, followed by determination of the nucleotide sequences thereof Based on the resultant nucleic acid sequence information, the entire protein-encoding region of the gene of interest was cloned by screening of cDNA library, rapid amplification of cDNA end (RACE) and reverse transcription-polymerase chain reaction (RT-PCR). Subsequently, cDNA fragments that have all of the partial amino acid sequences of the purified protein and homologues of the cDNA fragments were cloned. In the same manner, cDNA homologues were also cloned from *Gentiana triflora* and lobelia. For functional analysis of resultant clones, recombinant proteins obtained with Baculovirus-insect sell recombinant proteins produced by the Baculocirus-insect cell expression system were used to confirm enzyme activities. The present invention has been achieved based on the above-described findings.

The present invention provides the following [1] to [19].

[1] The 1st aspect of the present invention relates to a gene encoding a protein having an activity of transferring an aromatic acyl group to a sugar residue of a flavonoid using 1-O-acyl-β-D-glucose as an acyl donor.

[2] The 2nd aspect of the present invention relates to the gene of [1] above, which encodes any one of the following proteins (a) to (d):
(a) a protein having the amino acid sequence as shown in SEQ ID NO: 2, 4, 6, 8, 10 or 12;
(b) a protein having the amino acid sequence as shown in SEQ ID NO: 2, 4, 6, 8, 10 or 12 which has addition, deletion and/or substitution of one or plurality of amino acids;
(c) a protein having an amino acid sequence which shows 20% or more homology to the amino acid sequence as shown in SEQ ID NO: 2, 4, 6, 8, 10 or 12;
(d) a protein having an amino acid sequence which shows 70% or more homology to the amino acid sequence as shown in SEQ ID NO: 2, 4, 6, 8, 10 or 12.

[3] The 3rd aspect of the present invention relates to a gene which hybridizes to a part or the whole of a nucleic acid represented by the nucleotide sequence as shown in SEQ ID NO: 1, 3, 5, 7, 9 or 11, or a nucleic acid encoding the amino acid sequence as shown in SEQ ID NO: 2, 4, 6, 8, 10 or 12 under stringent conditions and encodes a protein having an activity of transferring an aromatic acyl group to a sugar residue of a flavonoid using 1-O-acyl-β-D-glucose as an acyl donor.

[4] The 4th aspect of the present invention relates to a gene from butterfly pea or lobelia encoding a protein that has an activity of transferring a glucosyl group to a hydroxyl group at position 1 of hydroxycinnamic acid using UDP-glucose as a glucosyl donor and synthesizes an acyl donor.

[5] The 5th aspect of the present invention relates to the gene of [4] above, which encodes any one of the following proteins (a) to (d):
(a) a protein having the amino acid sequence as shown in SEQ ID NO: 14, 16 or 18;
(b) a protein having the amino acid sequence as shown in SEQ ID NO: 14, 16 or 18 which has addition, deletion and/or substitution of one or plurality of amino acids;
(c) a protein having an amino acid sequence which shows 20% or more homology to the amino acid sequence as shown in SEQ ID NO: 14, 16 or 18;
(d) a protein having an amino acid sequence which shows 70% or more homology to the amino acid sequence as shown in SEQ ID NO: 14, 16 or 18.

[6] The 6th aspect of the present invention relates to a gene from butterfly pea or lobelia which hybridizes to a part or the whole of a nucleic acid represented by the nucleotide sequence as shown in SEQ ID NO: 13, 15 or 17 or a nucleic acid encoding the amino acid sequence as shown in SEQ ID NO: 14, 16 or 18 under stringent conditions and encodes a protein having an activity of transferring a glucosyl group to a hydroxyl group at position 1 of hydroxycinnamic acid using UDP-glucose as a glucosyl donor and synthesizing an acyl donor.

[7] The 7th aspect of the present invention relates to a vector comprising the gene of any one of [1] to [3] above.

[8] The 8th aspect of the present invention relates to a vector comprising the gene of any one of [4] to [6] above.

[9] The 9th aspect of the present invention relates to a host cell which has been transformed by the vector of [7] or [8] above.

[10] The 10th aspect of the present invention relates to a protein encoded by the gene of any one of [1] to [6] above.

[11] The 11th aspect of the present invention relates to a method of preparing a protein having an activity of transferring an aromatic acyl group to a sugar residue of a flavonoid using 1-O-acyl-β-D-glucose as an acyl donor or a protein having an activity of transferring a glucosyl group to a hydroxyl group at position 1 of hydroxycinnamic acid using UDP-glucose as a glucosyl donor, which comprises culturing or growing the host cell of [9] above and recovering the protein from the host cell.

[12] The 12th aspect of the present invention relates to a method of preparing a protein by in vitro translation using the gene of any one of [1] to [6] above.

[13] The 13th aspect of the present invention relates to a plant which has been transformed by introducing thereinto the gene of any one of [1] to [6] above or the vector of [7] or [8] above.

[14] The 14th aspect of the present invention relates to a offspring of the plant of [13] above, which has the same nature as that of the plant.

[15] The 15th aspect of the present invention relates to a tissue of the plant of [13] above or the offspring of [14] above.

[16] The 16th aspect of the present invention relates to a cut flower of the plant of [13] above or the offspring of [14] above.

[17] The 17th aspect of the present invention relates to a method of transferring an aromatic acyl group to a sugar residue of a flavonoid using 1-O-acyl-β-D-glucose as an acyl donor, which comprises introducing the gene of any one of [1] to [3] above or the vector of [7] above into a plant or plant cell and expressing the gene.

[18] The 18th aspect of the present invention relates to a method of modifying the flower color of plant, comprising introducing the gene of any one [1] to [6] above or the vector of [7] or [8] above into a plant or plant cell and expressing the gene.

[19] The 19th aspect of the present invention relates to a method of modifying the flower color of a plant body in a plant having the gene of any one of [1] to [6] above, comprising inhibiting the expression of the gene.

Hereinbelow, the present invention will be described in detail.

(1) Gene (1-1) First Gene

The first gene of the present invention encodes a protein having an activity of transferring an aromatic acyl group to a sugar residue of a flavonoid using 1-O-acyl-β-D-glucose as an acyl donor. As examples of the first gene of the present invention, the following genes (A) to (D) may be given.

(A) A gene encoding a protein having the amino acid sequence as shown in SEQ ID NO: 2, 4, 6, 8, 10 or 12 and having the above-described acyltransferase activity.

The expression "having the amino acid sequence as shown in SEQ ID NO: 2, 4, 6, 8, 10 or 12" used herein is intended to include not only a protein consisting of the amino acid sequence as shown in SEQ ID NO: 2, 4, 6, 8, 10 or 12 alone but also a protein which has a plurality of amino acids added to the N-terminus or C-terminus of the above protein. The number of amino acids added is not particularly limited as long as the protein retains the above-described acyltransferase activity Usually, the number is within 400, preferably within 50.

(B) A gene encoding a protein having the amino acid sequence as shown in SEQ ID NO: 2, 4, 6, 8, 10 or 12 which has addition, deletion and/or substitution of one or plurality of amino acids; and yet having the above-described acyltransferase activity.

Such a protein having the amino acid sequence with addition, deletion and/or substitution may be either a natural protein or artificial protein. The number of amino acids added, deleted and/or substituted is not particularly limited as long as the protein retains the above-described acyltransferase activity. Usually, the number is within 20, preferably within 5.

(C) A gene encoding a protein having an amino acid sequence showing a specific homology to the amino acid sequence as shown in SEQ ID NO: 2, 4, 6, 8, 10 or 12 and yet having the above-described acyltransferase activity.

The term "specific homology" used herein means usually 20% or more homology, preferably 50% or more homology, more preferably 60% or more homology, most preferably 70% or more homology.

(D) A gene which hybridizes to a part or the whole of a nucleic acid represented by the nucleotide sequence as shown in SEQ ID NO: 1, 3, 5, 7, 9 or 11 or a nucleic acid encoding the amino acid sequence as shown in SEQ ID NO: 2, 4, 6, 8, 10 or 12 under stringent conditions and encodes a protein having the above-described acyltransferase activity.

The term "a part of a nucleic acid" used herein means, for example, a part encoding 6 or more consecutive amino acids within the consensus sequence region. The term "stringent conditions" used herein means those conditions under which specific hybridization alone takes place and non-specific hybridization does not occur. For example, conditions such as temperature 50° C. and salt concentration 5×SSC (or concentration equivalent thereto) may be given. It should be noted that appropriate hybridization temperature varies depending on the nucleotide sequence, length, etc. of the nucleic acid. For example, when a DNA fragment consisting of 18 nucleotides encoding 6 amino acids is used as a probe, 50° C. or less is preferable.

Examples of genes selected by such hybridization include natural genes, e.g., plant-derived genes, especially genes derived from butterfly pea, lobelia and gentian. Genes selected by hybridization may be either cDNA or genomic DNA.

Of the above genes, genes occurring in nature may be obtained, for example, by screening cDNA library as described later in Examples. Genes not occurring in nature may also be obtained by using site directed mutagenesis, PCR or the like.

(1-2) Second Gene

The second gene of the present invention is a gene derived from butterfly pea or lobelia encoding a protein that has an activity of transferring a glucosyl group to a hydroxyl group at position 1 of hydroxycinnamic acid using UDP-glucose as a glucosyl donor and synthesizes 1-$O$-acyl-$\beta$-D-glucose as an acyl donor of the enzyme that catalyzes a reaction transferring an aromatic acyl group to a sugar residue of anthocyanin.

As examples of the second gene of the present invention, the following genes (E) to (H) may be given.

(E) A gene encoding a protein having the amino acid sequence as shown in SEQ ID NO: 14, 16 or 18 and having the above-described glucosyltransferase activity.

The expression "having the amino acid sequence as shown in SEQ ID NO: 14, 16 or 18" used herein is intended to include not only a protein consisting of the amino acid sequence as shown in SEQ ID NO: 14, 16 or 18 alone but also a protein which has a plurality of amino acids added to the N-terminus or C-terminus of the above protein. The number of amino acids added is not particularly limited as long as the protein retains the above-described glucosyltransferase activity Usually, the number is within 400, preferably within 50.

(F) A gene encoding a protein having the amino acid sequence as shown in SEQ ID NO: 14, 16 or 18 which has addition, deletion and/or substitution of one or plurality of amino acids; and yet having the above-described glucosyltransferase activity.

Such a protein having the amino acid sequence with addition, deletion and/or substitution may be either a natural protein or artificial protein. The number of amino acids added, deleted and/or substituted is not particularly limited as long as the protein retains the above-described glucosyltransferase activity. Usually, the number is within 20, preferably within 5.

(G) A gene encoding a protein having an amino acid sequence showing a specific homology to the amino acid sequence as shown in SEQ ID NO: 14, 16 or 18 and yet having the above-described glucosyltransferase activity.

The term "specific homology" used herein means usually 20% or more homology, preferably 50% or more homology, more preferably 60% or more homology, most preferably 70% or more homology.

(H) A gene which hybridizes to a part or the whole of a nucleic acid represented by the nucleotide sequence as shown in SEQ ID NO: 13, 15 or 17 or a nucleic acid encoding the amino acid sequence as shown in SEQ ID NO: 14, 16 or 18 under stringent conditions and encodes a protein having the above-described glucosyltransferase activity.

The term "a part of a nucleic acid" used herein means, for example, a part encoding 6 or more consecutive amino acids within the consensus sequence region. The term "stringent conditions" used herein means those conditions under which specific hybridization alone takes place and non-specific hybridization does not occur. For example, conditions such as temperature 50° C. and salt concentration 5×SSC (or concentration equivalent thereto) may be given. It should be noted that appropriate hybridization temperature varies depending on the nucleotide sequence, length, etc. of the nucleic acid. For example, when a DNA fragment consisting of 18 nucleotides encoding 6 amino acids is used as a probe, 50° C. or less is preferable.

Examples of genes selected by such hybridization include natural genes, e.g., plant-derived genes, especially genes derived from butterfly pea, lobelia and gentian. Genes selected by hybridization may be either cDNA or genomic DNA.

Of the above genes, genes occurring in nature may be obtained, for example, by screening cDNA library as described later in Examples. Genes not occurring in nature may also be obtained by using site directed mutagenesis, PCR or the like.

(2) Vector

The vector of the present invention may be prepared by inserting the gene described in (1) above into a known expression vector.

The known expression vector to be used is not particularly limited as long as it comprises an appropriate promoter, terminator, replication origin, etc. As the promoter, trc promoter, tac promoter, lac promoter or the like may be used when the gene is to be expressed in bacteria; glycelaldehyde 3-phosphate dehydrogenase promoter, PH05 promoter or the like may be used when the gene is to be expressed in yeasts; amylase promoter, trpC promoter or the like may be used when the gene is to be expressed in filamentous fungi; and SV40 early promoter, SV40 late promoter, polyhedrin promoter or the like may be used when the gene is to be expressed in animal cells.

(3) Transformed Host Cell

The transformed host cell of the present invention is a host cell transformed by the vector described in (2) above.

The host cell may be either a prokaryote or eukaryote. Examples of prokaryotes which may be used as a host cell include, but are not limited to, *Escherichia coli* and *Bacillus subtilis*. Examples of eukaryotes which may be used as a host cell include, but are not limited to, yeasts, filamentous fungi, and cultured cells of animals and plants. Examples of yeasts include, but are not limited to, *Saccharomyces cerevisiae*, *Pichia patoris*, *Pichia methanolica* and *Schizosaccharomyces pombe*. Examples of filamentous fungi include, but are not limited to, *Aspergillus oryzae* and *Aspergillus niger*. Examples of animal cells include, but are not limited to, rodents such as mouse (*Mus musculus*), Chinese hamster (*Cricetulus griseus*); primates such as monkey and human (*Homo sapiens*); amphibians such as *Xenopus laevis*; insects such as *Bombyx mori*, *Spodoptera frugiperda* and *Drosophila melonogaster*.

The method of transformation by the vector is not particularly limited. The transformation may be performed according to conventional methods.

(4) Protein

The protein encoded by the gene described in (1) above is also included in the present invention. This protein may be prepared, for example, by the method described in (5) below.

(5) Method of Preparation of Protein

The method of preparing a protein according to the present invention comprises culturing or growing the host cell described in (3) above and then recovering from the host cell a protein having an activity of transferring an aromatic acyl group to a sugar residue of a flavonoid using 1-O-acyl-β-D-glucose as an acyl donor or a protein having an activity of transferring a glucosyl group to a hydroxyl group at position 1 of hydroxycinnamic acid using UDP-glucose as a glucosyl donor and synthesizing an acyl donor. Alternatively, the method may be characterized by in vitro translation or the like. Culturing or growing the host cell may be performed by methods suitable for the type of the host cell. The recovery of the protein may be performed by conventional methods. For example, the protein may be recovered and purified from the cultured cells or medium by techniques such as filtration, centrifuge, cell disruption, gel filtration chromatography, ion exchange chromatography, affinity chromatography or hydrophobic chromatography, etc. Thus, the protein of interest may be obtained.

(6) Plant

The plant of the present invention is a plant which has been transformed by introducing thereinto the gene described (1) above or the vector described in (2) above.

The target plant into which the gene or vector is to be introduced is not particularly limited. For example, rose, chrysanthemum, cineraria, snapdragon, cyclamen, orchid, prairie gentian, freesia, gerbera, gladiolus, babies'-breath, *Kalanchoe blossfeldiana*, lily, pelargonium, geranium, petunia, tulip, lobelia, *Torenia foumieri*, rice, barley, wheat, rapeseed, potato, tomato, aspen, banana, eucalyptus, sweet potato, soybean, alfalfa, lupine, corn, cauliflower, lobelia, apple, grape, peach, Japanese persimmon, plum and citrus may be enumerated.

(7) Offspring of Plant

The offspring of the plant described in (6) above is also included in the present invention.

(8) Tissue of Plant, etc.

Cells, tissues and organs of the plant described in (6) above or the offspring of the plant described in (7) above are also included in the present invention.

(9) Cut Flower of Plant, etc.

Cut flowers of the plant described in (6) above or the offspring of the plant described in (7) above are also included in the present invention.

(10) Method of Transfer of Aromatic Acyl Group

A method of transferring an aromatic acyl group to a sugar residue of a flavonoid using 1-O-acyl-β-D-glucose as an acyl donor, which comprises introducing the gene described in (1-1) above or the vector described in (2) above (comprising the first gene) into a plant or plant cell and expressing the gene, is also included in the present invention.

(11) Method of Modification of Flower Color

The method of modifying a flower color according to the present invention is a method of modifying the color of flower or fruit of a plant, comprising introducing the gene described in (1) above or the vector described in (2) above into a plant or plant cell and expressing the gene; or inhibiting the expression of the gene described in (1) above in a plant having the gene. The target plant for gene transfer is not particularly limited. For example, the plants enumerated in (6) above may be used. The target plant in which expression of the gene described in (1) is to be inhibited is not particularly limited as long as the plant has the gene.

Transfer and expression of the gene described in (1) above may be performed by conventional methods. Inhibition of the expression of the gene described in (1) above may also be performed by conventional methods (e.g., antisense method, co-suppression method or RNAi method).

Effect of the Invention

By using the expression product of the gene obtained by the present invention, it is possible to transfer an aromatic acyl group to a sugar residue of a flavonoid using 1-O-acyl-β-D-glucose as an acyl donor. As a result, it has become possible to modify plant tissues (such as flower and fruit) which are expressing colors via accumulation of flavonoids.

BEST MODE FOR CARRYING OUT THE INVENTION

Hereinbelow, the present invention will be described in more detail with reference to the following Examples. The invention of the present patent application is not limited by the following Examples. Analytical chemical techniques, molecular biological techniques and biochemical techniques were according to those described in Japanese Unexamined Patent Publication No. 2005-95005 unless otherwise specified.

Example 1

Preparation of Substrates for Enzyme Reaction and Standard Compounds (1) Preparation of Plant Materials Seeds of butterfly pea (*Clitoria ternatea*) cv. Double blue (Sakata Seed Corporation) were sown aseptically and rooted, and then seedlings were raised and grown in a glass greenhouse by conventional methods. With respect to *Gentiana triflora* cv. Hakkoda, cut flowers were collected from plants cultivated in Aomori Prefecture and petals alone were prepared for experiments. Seeds of *Lobelia erinus* cv. Riviera Midnight Blue, *L. erinus* cv. Aqua White, *L. erinus* cv. Aqua Lavender and *L. erinus* cv. Aqua Blue (all from Takii Seed) were sown in glass greenhouses and then grown up to flowering in plastic pots. Flower petals and flower bud petals were collected and frozen instantaneously with liquid nitrogen, followed by storage at −80° C.

(2) Isolation of Compounds

As authentic samples of 1-O-hydroxycinnamoyl-β-D-glucoses (Milkowski et al., (2000) FEBS Letters 486: 183-184; Bokern and Strack (1988) Planta 174:101-105; Bokern et al., (1991) Planta 184: 261-270; and Bokem et al., (1992) Botanica Acta 105: 146-151), i.e. 1-O-p-coumaroyl-β-D-glucose, 1-O-caffeoyl-β-D-glucose, 1-O-feruloyl-β-D-glucose and 1-O-sinapoyl-β-D-glucose, compounds released from Dr. Alfred Baumert and Prof Dieter Strack (Leibniz IPB, Halle, Germany) were used. 1-O-p-Coumaroyl-β-D-glucose was purified and isolated from petals of butterfly pea; and 1-O-caffeoyl-β-D-glucose and 1-O-feruloyl-β-D-glucose were purified and isolated from petals of lobelia (Kazuma et al., (2005) Abstracts of Japan Society for Bioscience, Biotechnology and Agrochemistry 2005 Annual Conference: 3). Delphinidin 3-(6-malonyl)glucoside 3',5'-diglucoside (ternatin C5: Terahara et al., (1998) Journal of Natural Products 61: 1361-1367), delphinidin 3,3',5'-triglucoside (preternatin C5: Terahara et al., (1990) Phytochemistry 29: 3686-3687) and delphinidin 3-(6-malonyl)glucoside-3'-glucoside (Kazuma et al., (2005) Chemistry & Biodiversity 1: 1762-1770) were purified and isolated from petals of butterfly pea.

Example 2

Standard Enzyme Activity Measurement

A reaction solution (20 µl) containing 100 mM phosphate buffer (pH 6.5), 0.4 mM anthocyanin (4 µl), 0.5 mM 1-O-acyl-β-D-glucose (4 µl) and an enzyme solution (8 µl) was reacted at 30° C. The reaction was terminated by adding 4 µl of 1M aqueous hydrochloric acid solution. After addition of 24 µl of 5% acetonitrile containing 0.05 M TFA, the reaction solution was filtered with Millex-LH filter (Millipore) and then analyzed by HPLC by feeding a 10 µl aliquot.

HPLC analysis of anthocyanin acyltransferase reaction products were performed with Develosil ODS-UG-5 column (3.0 i.d.×250 mm; Nomura Chemical) at a column temperature of 35° C. Against an initial solvent that was 0.05 M trifluoroacetate (TFA)-containing 5% acetonitrile (MeCN) aqueous solution, 0.05 M TFA-containing 40% MeCN was added with a linear concentration gradient from 14 to 86% (20 min) and the reaction products were eluted at a flow rate of 0.5 ml/min. The reaction products were detected with PDA and their molecular weights were confirmed by LC-MS/MS.

Example 3

Examination of Substrates to Be Used in Enzyme Activity Measurement

In order to detect an enzyme activity of transferring an aromatic acyl group to the sugar residue of flavonoids using 1-O-acyl-β-D-glucose as an acyl donor, various types of 1-O-acyl-β-D-glucose and anthocyanin were examined. Briefly, enzyme activities were measured using 35-70% ammonium sulfate precipitation fraction of the protein extracted from butterfly pea petals as an enzyme solution, preternatin C5 as an acyl receptor, and various 1-O-acyl-β-D-glucoses as an acyl donor. As a result, acyltransferase activity was detected in all of the 1-O-acyl-β-D-glucoses tested. Specific activity was higher in the following order: 1-O-sinapoyl-β-D-glucose, 1-O-feruloyl-β-D-glucose, 1-O-p-coumaroyl-β-D-glucose and 1-O-caffeoyl-β-D-glucose. Further, enzyme activities were measured using 1-O-p-coumaroyl-β-D-glucose as an acyl donor and various types of anthocyanin as an acyl acceptor. As a result, acyltransferase activity was detected in all of the anthocyanins tested (preternatin C5, ternatin C5 and delphinidin 3-(6-malonyl)glucoside-3'-glucoside).

Example 4

Purification of Protein 3'AT Having Enzyme Activity of Transferring Aromatic Acyl Group to Glucosyl Group at Position 3' of Anthocyanin From butterfly pea petals, an acyltransferase (3'AT) that is a protein having an activity of transferring p-coumaroyl to position 3 of glucosyl group at position 3' was purified using preternatin C5 and 1-O-p-coumaroyl-β-D-glucose as substrates for enzyme activity measurement, based on the purification methods for a glucose acyltransferase that biosynthesizes 1,2-di-O-acyl-β-D-glucose (Li et al., (1999) Plant Physiology 121: 453-460; Li and Steffens (2000) Proceedings of the National Academy of Sciences of the United States of America 97: 6902-6907; PCT/WO97/48811). Protein purification processes were performed at 0-4° C. Purification was achieved by carrying out protein extraction, ammonium sulfate fractionation, ion exchange chromatography using TSK gel DEAE-TOYOPEARL 650M (Tosoh), chromatography using concanavalin A (ConA)-agarose (Honen), chromatography using Mono P HR 5/20 (Amersham Bioscience) and ion exchange chromatography using Mono Q HR 5/5 (Amersham Bioscience) in this order. For column chromatography using TSK gel DEAE-TOYOPEARL 650M, Mono P and Mono Q, FPLC (Pharmacia) was used. For column chromatography using ConA-agarose, an open column was used.

(1) Preparation of Crude Enzyme Solution

Frozen petals (510.5 g) from butterfly pea were ground in a mortar with a pestle in the presence of liquid nitrogen. Then, after addition of about 1,000 ml of buffer A [100 mM Tris-HCl (pH 7.5), 5 mM dithiothreitol (DTT), 10 µM p-amidinophenyl methylsulfonyl fluoride (pAPMSF)], 5 g of polyvinylpolypyrrolidone (PVPP) and an appropriate amount of sea sand, they were ground further. An extract suspension was prepared therefrom and centrifuged at 7,000 rpm for 15 min. The resultant supernatant was filtered with quadruply layered gauze. To the supernatant of the resultant filtrate, 800 g of Dowex 1×2 (100-200 mesh; Muromachi Chemical) was added. The mixture was left stationary for 15 min and then filtered with a nylon mesh to thereby obtain a crude enzyme solution (1240 ml).

(2) Ammonium Sulfate Fractionation

The crude enzyme solution was subjected to salting out with 35% saturated ammonium sulfate for 30 min. Then, insoluble matters were removed by centrifuging at 7,000 rpm for 20 min. After further salting out with 70% saturated ammonium sulfate overnight, the solution was centrifuged at 7,000 rpm for 20 min to thereby obtain a protein precipitate. This precipitate was redissolved in buffer B [20 mM Tris-HCl (pH 7.5), 1 mM DTT, 10 μM pAPMSF] and desalted with Sephadex G-25 Fine column (70 mm×40 mm i.d.; Amersham Bioscience) equilibrated with buffer B. Protein fractions (1598.4 mg/144 ml) were collected and subjected to the following chromatographies.

(3) DEAE Anion Exchange FPLC

TSK gel DEAE-TOYOPEARL 650M (30 ml) was packed in a column (XK16/20, 180 mm×16 mm i.d.) and equilibrated with buffer B. The enzyme solution was applied to the column and the protein was fractionated with a linear gradient of NaCl concentration changing from 0 mM to 200 mM in 45 min at a flow rate of 8 m/min. After measurement of acyltransferase activity in each fraction, active fractions (840 ml) were collected and subjected to salting out with 90% saturated ammonium sulfate overnight. The resultant solution was centrifuged at 7,000 rpm for 20 min to thereby obtain a protein precipitate. This precipitate was redissolved in 40 ml of buffer B. The thus dissolved protein solution was divided into 5 ml aliquots and stored at −80° C. until subsequent purification.

(4) ConA Agarose Column Chromatography

The cryopreserved DEAE active fraction (5 ml) was dissolved and then desalted with a gel-filtration column PD-10 (Amersham Bioscience) equilibrated with buffer C [50 mM HEPES-NaOH (pH 7.5), 10% glycerol, 0.2 M KCl]. The desalted protein solution (7 ml) was concentrated to 0.5 ml by ultracentrifugal filtration. The resultant concentrated protein solution (0.5 ml) was applied to ConA agarose (4 ml) packed in a column and equilibrated with buffer C. After application of the concentrated protein solution, the column was washed with 4-bed volumes of buffer C (16 ml). The protein adsorbed onto ConA agarose was eluted with 3-bed volumes of buffer D [50 mM HEPES-NaOH (pH 7.5), 10% glycerol, 0.2 M KCl, 1 M α-D-methylglucoside] (12 ml). The eluate was poured into a dialysis column SnakeSkin Dialysis Tubing MWCO 10,000 (PIERCE Biotechnology) and dialyzed with buffer E [25 mM piperazine-HCl (pH 5.5)] (3,000 ml) overnight. After further desalting with PD-10, centrifugal concentration with Amicon Ultra (molecular weight cut off 10,000; Millipore) was performed to thereby obtain 0.5 ml of a protein solution (0.5 mg/ml).

(5) Mono P FPLC

The thus obtained ConA active fraction (0.5 ml) was applied to a Mono P column equilibrated with buffer E, at a flow rate of 0.8 ml/min. After the application of this protein, the column was washed with buffer E (6 ml). The protein was eluted with a 1:10 (v/v) dilution of Polybuffer 74-HCl (pH 4.0) (32 ml). The eluate was divided into 0.8 ml aliquots, which were fractionated in test tubes each containing 0.08 ml of 0.5 M HEPES-NaOH (pH 7.5) and 0.08 ml of glycerol. Then, active fractions were collected (8.8 ml) and concentrated into 1.5 ml of a protein solution by centrifugal concentration.

(6) Mono Q Strong Anion Exchange FPLC

The thus obtained Mono P active fraction (1.5 ml) was applied to Mono Q HR5/5 column equilibrated with buffer F [10 mM Tris-HCl (pH 7.5), 1 mM DTT, 10 μM pAPMSF], at a flow rate of 1.0 ml/min. The protein solution was fractionated by 1 ml with a linear concentration gradient of liquid B from 0% to 25% in 60 min using buffer F [10 mM Tris-HCl (pH 7.5), 1 mM DTT, 10 μM pAPMSF] as liquid A and buffer G [10 mM Tris-HCl (pH 7.5), 1 mM DTT, 10 μM pAPMSF, 1M NaCl] as liquid B. Active fractions (6 ml) were collected and concentrated into 0.1 ml of a protein solution (0.9 μg/ml) by centrifugal concentration.

The specific activity of the 3'AT protein was found to be 1492.6 pkat/mg. Compared to the specific activity of the DEAE active fraction of 0.252 pkat/mg, this represents 5923-fold purification. Further, when silver-staining was performed after active fractions were fractionated by SDS-PAGE, a clear 30.8 kDa band and a thin 24.1 kDa band alone were detected. It is reported that serine carboxypeptidase-like acyltransferase (SCPL-AT) is a protein which functions as a hetero-tetramer composed of a 34 kDa and a 24 kDa polypeptides (Li et al., (1999) Plant Physiology 121: 453-460) or a hetero-dimer composed of a 30 kDa and a 17 kDa polypeptides (Shirley and Chapple (2003) Journal of Biological Chemistry 278: 19870-19877). Thus, the analytical results by SDS-PAGE demonstrated that the 3'AT protein purified from butterfly pea petals was sufficiently uniformly purified. It is reported that SCPL-AT, like serine carboxypeptidase (SCPase), is modified by sugar chains, and the 3'AT protein binds to ConA resin. Therefore, it is highly possible that the 3'AT protein is modified by sugar chains. Further, since silver-staining weakly stains those polypeptides with sugar chain modification, it was shown that the 24.1 kDa subunit may be modified with sugar chains.

Example 5

Partial Purification of 3'5'AT Protein Having Sequential Acyl Transfer Activity to Glucosyl Group at Positions 3' and 5' of Anthocyanin In the process of purification of 3' AT protein, an activity was detected which acylates the glucosyl groups at positions 3' and 5' of the B ring of preternatin C5 in succession. Although 3'5'AT activity was also detected in the 3'AT active fraction after ammonium sulfate fractionation, DEAE anion exchange FPLC, ConA chromatography and Mono P FPLC, 3'5'AT activity was not detected in the 3'AT active fraction after Mono Q FPLC. Then, the inventors performed fractionation and partial purification of an acyltransferase that is a protein having an activity of transferring a feruloyl group to position 6 of glucosyl group at position 3' of anthocyanin (3' AT) and a 3'5'AT protein that is a protein having activity to transferring a feruloyl group to position 6 of both glucosyl groups at positions 3' and 5' of anthocyanin from the 3'AT protein obtained, using preternatin C5 and 1-$O$-feruloyl-β-D-glucose as substrates for enzyme activity measurement.

(1) Preparation of Crude Enzyme Solution and Ammonium Sulfate Fractionation

A fraction (50 ml) containing a protein (269.15 mg) which has both 3'AT and 3'5'AT activities was obtained from 101.4 g of butterfly pea petals according to the methods described in (1) Preparation of Crude Enzyme Solution and (2) Ammonium Sulfate Fractionation in Example 3 with necessary modifications.

(2) DEAE Anion Exchange FPLC

The enzyme solution was applied to TSK gel DEAE-TOYOPEARL 650M column equilibrated with buffer B, and the protein was fractionated with a linear gradient of NaCl concentration from 0 mM to 200 mM in 360 min at a flow rate of 1 ml/min. The recovered 3'AT active fraction (54 ml) and 3'5'AT active fraction (42 ml) were subjected to salting out with 90% saturated ammonium sulfate overnight and then centrifuged at 7,000 rpm for 20 min to thereby obtain. The resultant protein precipitates were redissolved by the method described in (3) in Example 3 with necessary modifications and then desalted and concentrated by the method described in (4) in Example 3 with necessary modifications.

(3) ConA Agarose Chromatography

Concentrated protein solutions of 3'AT and 3'5'AT, respectively, were applied to ConA agarose (5 ml) separately. Chromatography, dialysis and desalting were performed as described in (4) in Example 3.

(4) Mono P FPLC

ConA active fraction was subjected to chromatography, desalting and concentration according to the methods described in (5) in Example 3. The specific activity of 3'AT activity in the 3'AT active fraction was 45.9 pkat/mg, which represents 100-fold purification compared to the specific activity of 0.46 pkat/mg after ammonium sulfate fractionation. 3'5'AT activity was also detected in the 3'AT active fraction, and the specific activity thereof was 3.6 pkat/mg. On the other hand, the specific activity of 3'5'AT activity in the 3'5'AT active fraction was 9.6 pkat/mg, which represents 74-fold purification compared to the specific activity of 0.13 pkat/mg after ammonium sulfate fractionation. 3'AT activity was also detected in the 3'5'AT active fraction, and the specific activity thereof was 4.1 pkat/mg.

Therefore, existence of the following two proteins was recognized in butterfly pea petals: 3'AT having an acyl transfer activity to glucosyl group at position 3' of anthocyanin B ring and 3'5'AT having a sequential acyl transfer activity to glucosyl groups at positions 3' and 5' in succession.

Example 6

Determination of the Amino Acid Sequence of Anthocyanin 3'AT Protein

The 3'AT protein purified in Example 4 (approx. 65 ng) was fractionated by SDS-PAGE and stained with PAGE Blue83 (CBB R-250; Daiichi Pure Chemicals). The stained bands (30.8 kDa and 24.1 kDa) were cut out. These samples were designated CTDCPQ-30 and CTDCPQ-24, respectively They were treated with trypsin-containing Tris buffer (pH 8.0) at 35° C. for 20 hr. Subsequently, the total volume of the solution was subjected to reversed phase HPLC to separate fragment peptides. As a control, a portion of the gel without any band was cut out and treated in the same manner. The conditions of HPLC separation of fragment peptides were as described below. Briefly, as a column, Symmetry C18 3.5 µm (1.0×150 mm; Waters) was used. The flow rate was 50 µl/min. Solvent A was 0.1% TFA-containing 2% acetonitrile solution. Solvent B was 0.09% TFA-containing 90% acetonitrile solution. For the initial 6 min, the concentration of solvent B was 0%; in the subsequent 5 min, the concentration was raised to 10%; in the subsequent 75 min, the concentration was raised to 50%; in the subsequent 5 min, the concentration was raised to 100%; then, the concentration of solvent B was retained at 100% for 5 min. Detection was carried out at 210 nm and 280 nm. Fractionation was performed by 50 µl.

Fraction No. 35 and No. 44+45 of CTDCPQ-30 and fraction No. 18+19 of CTDCPQ-24 were subjected to determination of amino acid sequences. N-terminal amino acid sequences of individual fragment peptides were analyzed using Procise 494 cLC Protein Sequencing System. The determined amino acid sequences are shown below.

```
                          (SEQ ID NOs: 19 and 20)
CTDCPQ-30-T35:            (R/K)WLIDHPK (SEQ ID NOs: 21 and 22)
CTDCPQ-30-T44+45:         (R/K)ISFAHILER (SEQ ID NOs: 23 and 24)
CTDCPQ-24-T18+19:         (R/K)RPLYEXNTM
```

Example 7

Design of Primers for Amplifying SCPL-AT cDNA Fragment

Nucleotide sequences for genes encoding proteins that catalyze reactions using 1-O-acyl-β-D-glucose as an acyl donor are highly homologous to nucleotide sequences for genes encoding serine carboxypeptidase (SCPase). Proteins that catalyze reactions using 1-O-acyl-β-D-glucose as an acyl donor are designated SCPL-AT (Milkowski and Strack (2004) Phytochemistry 65: 517-524). Then, degenerate primers were designed based on regions and their nucleotide sequences highly conserved in SCPase and SCPL-AT. In order to specify highly conserved regions and to design primers, multiple alignment using CLUSTAL W program, Block Marker (blocks.fhcrc.org/blocks/) and CODEHOP (blocks.fhcrc.org/codehop.html) were used. Sequences used for multiple alignment were the amino acid sequences of NCBI/EMBL/DDBJ accession numbers AF242849, AF275313, AF248647, AY033947, AY383718 and X80836 (REGION: 12728.14326) and UniProt/Swiss-Prot accession numbers P07519, P08819 and P37890. The synthesized CODEHOP primers and degenerate primers are shown below.

```
                                      (SEQ ID NO: 25)
cdhp Fd:     GGACCCCGTGATGATCTGGYTIAMIGG (SEQ ID NO: 26)
cdhp Rv:     CCGCAGAAGCAGGAGCAICCIGGICC (SEQ ID NO: 27)
blockA Fd:   AMIGGWGGICCTGGITGYWSIWS (SEQ ID NO: 28)
blockB Fd:   GAIWSICCIGYIGGIWSIGG (SEQ ID NO: 29)
blockC Fd:   RTIGSIGGIGAIWSITAYDSIGG (SEQ ID NO: 30)
blockE Rv:   RTCRTGRTCICCISWRWA (SEQ ID NO: 31)
blockF Ry:   GGYTTRTAYTCIGGIRCIGTRTGICC
```

Example 8

Cloning of Butterfly Pea SCPL-AT cDNA (1) Preparation of RNA

Butterfly pea petals were divided into stages in terms of flower bud length by 5 mm. Briefly, flower bud lengths of 5-10 mm were regarded as stage 1; flower bud lengths of 10-15 mm were regarded as stage 2; flower bud lengths of 15-20 mm were regarded as stage 3; flower bud lengths of 20-25 mm were regarded as stage 4; flower bud lengths of 25-30 mm were regarded as stage 5; flower bud lengths of 30-35 mm were regarded as stage 6; flower bud lengths of 35-40 mm were regarded as stage 7; flower bud lengths of 40-45 mm were regarded as stage 8; flower bud lengths of 45-50 mm were regarded as stage 9; and the flowering stage was regarded as stage 10. Total RNA was prepared from several hundred milligrams of petals of each stage using TRIzol (Invitrogen). From the thus prepared total RNA (50 μg), poly(A)$^+$RNA was purified for each stage using Oligotex-dT30 super (Takara Bio) according to the method recommended by the manufacturer to thereby prepare 15 μl of poly(A)$^+$RNA solution.

(2) Amplification of cDNA Fragment by Degenerate RT-PCR and Cloning Thereof

Using the purified poly(A)$^+$RNA solution (15 μl) as a template, a single-strand cDNA was prepared with 1st strand cDNA synthesis kit (Amersham Bioscience) according to the method recommended by the manufacturer. The cDNAs of all stages thus synthesized were mixed in equal amounts to thereby prepare a template for PCR reaction. For PCR reaction, the CODEHOP primers and degenerate primers as shown in Example 7 and NotI-d(T)$_{18}$ primer (Amersham Bioscience) were used.

First, PCR reaction was performed with various primer pairs selected from the following: cdhp Fd and blockA Fd primers and three types of reverse primers. Using 2 μl of single strand cDNA solution as a template, 2 μl each of forward primer and reverse primer, and 2 units of ExTaq polymerase (Takara Bio), a 50 μl reaction solution was prepared and PCR was performed according to the method recommended by the manufacturer. Primer pairs used were 1: cdhp Fd and NotI-d(T)$_{18}$, 2: blockA Fd and NotI-d(T)$_{18}$, 3: cdhp Fd and blockE Rv, 4: cdhp Fd and blockF Rv, 5: blockA Fd and blockE Rv; and 6: blockA Fd and blockF Rv. The concentrations of CODEHOP primers and degenerate primers were adjusted to 50 μM, and the concentration of NotI-d(T)$_{18}$ primer was adjusted to 10 μM. Thermal conditions of the PCR reaction were as follows: 95° C. for 3 min, then 40 cycles of 95° C. for 30 sec, 55° C. for 45 sec and 72° C. for 80 sec, and finally 72° C. for 7 min. The resultant reaction products were subjected to agarose gel electrophoresis. Products of expected sizes obtained from reactions with the above-described primer pairs 3 to 6 were recovered from gel fragments.

Using the PCR product (1 μl) obtained with the above-described primer pair 1 or 2 as a template, nested PCR was performed. Combinations of forward and reverse primers were 1: blockA Fd and blockF Rv, 2: cdhp Fd and blockF Rv, and 3: cdhp Fd and NotI-R21 (5'-TGGAAGAATTCGCGGC-CGCAG-3': SEQ ID NO: 32). Using 1 μl of the PCR product as a template, 1 μl each of forward primer and reverse primer, and 1 unit of ExTaq polymerase (Takara Bio), a 25 μl reaction solution was prepared and PCR was performed according to the method recommended by the manufacturer. PCR products of expected sizes obtained from the reaction using the above-described primer pair 1 and as a template the PCR product obtained with the primer pair of cdhp Fd and NotI-d(T)$_{18}$ were recovered from gel fractions.

Subsequently, PCR was performed with various primer pairs selected from the following: blockB Fd and blockC Fd primers and three types of reverse primers. Using 2 μl of single strand cDNA as a template, 2 μl each of forward primer and reverse primer, and 2 units of LATaq polymerase (Takara Bio), a 50 μl reaction solution was prepared and subjected to PCR. Primer pairs were 1: blockB Fd and NotI-d(T)$_{18}$, 2: blockC Fd and NotI-d(T)$_{18}$, 3: blockB Fd and blockE Rv, 4: blockC Fd and blockE Rv, 5: blockB Fd and blockF Rv and 6: blockC Fd and blockF Rv. The concentrations of CODEHOP primers and degenerate primers were adjusted to 50 μM, and the concentration of NotI-d(T)$_{18}$ primer was adjusted to 10 μM. Thermal conditions of the PCR reaction were as follows: 95° C. for 3 min, then 40 cycles of 95° C. for 30 sec, 50° C. for 45 sec and 72° C. for 80 sec, and finally 72° C. for 7 min. The resultant reaction products were subjected to agarose gel electrophoresis. Products of expected sizes obtained from reactions with the above-described primer pairs 4, 5 and 6 were recovered from gel fractions.

Using the PCR product (1 μl) obtained with the above-described primer pair 1, 2 or 3 as a template, nested PCR was performed individually. Primer pairs used were 1: blockB Fd and blockE Rv, 2: blockC Fd and blockE Rv, 3: blockB Fd and blockF Rv and 4: blockC Fd and blockF Rv. Using 100 pmole each of forward primer and reverse primer and 1 unit of LATaq polymerase (Takara Bio), a 50 μl reaction solution was prepared and PCR was performed according to the method recommended by the manufacturer. PCR products were subjected to agarose gel electrophoresis and products of expected sizes were recovered from gel fragments. Then, purified PCR products were subcloned into pGEM-T Easy vector (Promega), followed by determination of their nucleotide sequences. In order to estimate the gene products encoded by the resultant clones, BLAST search (blast.genome.jp/) was used. Further, after multiple alignment using CLUSTAL X, molecular phylogenetic trees were created with TreeView program, followed by estimation of the functions of the cDNAs.

The following primer pairs generated clones homologous to the SCPase or SCPL-AT of interest in the following cases: when cdhp Fd and blockE Rv or blockA Fd and blockE Rv were used in the 1st PCR; when blockA Fd and blockF Rv were used in nested PCR using the 1st PCR product obtained with cdhp Fd and NotI-d(T)$_{18}$ as a template; when blockC Fd and NotI-d(T)$_{18}$ were used; or when blockB Fd or blockC Fd was used in combination with blockE Rv or blockF Rv. Twenty-nine cDNA fragment clones which were believed to encode SCPase or SCPL-AT were obtained. Analyses by multiple alignment and with molecular phylogenetic trees confirmed existence of 4 types of SCPL clones. These butterfly pea SCPL clones were designated CtSCPL1, 2, 3 and 4, respectively Among all, cDNA fragment clones CtSCPL1 and CtSCPL4 were highly homologous to SCPL-AT and positioned in the same crade as that of known SCPL-AT when molecular phylogenetic trees were created.

(3) RACE of CtSCPL1 and CtSCPL4 cDNA Fragments

Total RNA was prepared from butterfly pea petals by a modified CTAB method (Chang et al., (1993) Plant Molecular Biology Reporter; Mukai and Yamamoto, Plant Cell Engineering Series 7, pp. 57-62). From the total RNA (250 μg), poly(A)$^+$RNA was purified using Oligotex-dT super according to the method recommended by the manufacturer. From approx. 480 ng of the thus purified poly(A)$^+$RNA, Gene Racer Ready cDNA (GRR cDNA) was synthesized using GeneRacer kit (Invitrogen) according to the method recommended by the manufacturer.

The thus synthesized cDNA was diluted at 1:3 to prepare a cDNA solution. Using this cDNA solution as a template, PCR was performed with GeneRacer 5' primer (5'-CGACTG-GAGCACGAGGACACTGA-3': SEQ ID NO: 33; Invitrogen) and CtSCPL1-R1 primer (5'-TACTGGAATGG-GAATACCAGAGTAAG-3': SEQ ID NO: 34) or CtSCPL1-R2 primer (5'-GGCATGGTGAACTAATGTCCAGTCAC-3':SEQ ID NO: 35) each of which is specific to an internal sequence of CtSCPL1 cDNA fragment. Further, PCR was performed with GeneRacer 5' primer and CtSCPL4-R1 primer (5'-GTGTCGACCCAGTCACAGTTTG-3': SEQ ID NO: 36) or CtSCPL4-R2 primer (5'-CTGATATAACCTCATTGTATGACTCC-3': SEQ ID NO: 37) each of which is specific to an internal sequence of CtSCPL4 cDNA fragment. Briefly, using the GRR cDNA as a templete, a primer pair of GeneRacer 5' primer (30 pmole) and CtSCPL1-R1 (20 pmole) or a pair of GeneRacer 5' primer (30 pmole) and CtSCPL1-R2 (20 pmole) and LATaq polymerase, PCR was performed in a 50 µl reaction solution according to the method recommended by the polymerase manufacturer. Thermal conditions of the PCR reaction were as follows: 94° C. for 3 min, then 30 cycles of 94° C. for 30 sec, 65° C. for 45 sec and 72° C. for 80 sec, and finally 72° C. for 7 min. Further, nested PCR was performed using the 1st PCR product as a template and GeneRacer 5' nested primer in combination with CtSCPL1-R1, CtSCPL1-R2, CtSCPL4-R1 or CtSCPL4-R2. Briefly, PCR was performed in a 50 µl reaction solution in the same manner as in the 1st PCR using the 1st PCR product as a template and LATaq polymerase (Takara Bio) according to the method recommended by the manufacturer. Products from the 1st PCR and nested PCR were fractionated by 0.8% agarose gel electrophoresis. Bands of amplified products were cut out and the PCR products were recovered. The PCR products purified from gel were TA-cloned into pGEM-T Easy vector. Several clones obtained were analyzed to thereby determine the 5' terminal nucleotide sequences of CtSCPL1 and CtSCPL4 cDNA fragments, respectively.

The synthesized GRR cDNA was diluted at 1:3 to prepare a cDNA solution. Using this cDNA solution as a template, PCR was performed with GeneRacer 3' primer (5'-GCTGTCAACGATACGCTACGTAACG-3': SEQ ID NO: 38; Invitrogen) or Gene Racer 3' nested primer (Invitrogen; 5'-CGCTACGTAACGGCATGACAGTG-3': SEQ ID NO: 39) as a reverse primer and CtSCPL1-F1 primer (5'-TCATAAGGGAAGTATTGGTGAATGGC-3': SEQ ID NO: 40) or CtSCPL1-F2 primer (5'-GTTTACCTTTCACGTCGGACATTCC-3': SEQ ID NO: 41), each of which is specific to an internal sequence of CtSCPL1 cDNA fragment, as a forward primer. Further, PCR was performed using as a forward primer CtSCPL4-F1 primer (5'-AGTGCACTACACATTCGTAAGG-3': SEQ ID NO: 42) or CtSCPL4-F2 primer (5'-GTAAATGGCGTCGATGTACCC-3': SEQ ID NO: 43) each of which is specific to an internal sequence of CtSCPL4 cDNA fragment. PCR, cloning and sequencing were performed in the same manner as performed in 5'RACE to thereby determine the 3' terminal nucleotide sequences of CtSCPL1 and CtSCPL4 cDNA fragments, respectively (4) Cloning of the Entire Protein-Encoding Region in CtSCPL1 cDNA The inventors synthesized, as a forward primer, pE-CtSCPL1-F (5'-GACGACGACAAGATGACCATAGTAGAGTTCCTTCCTG-3': SEQ ID NO: 44) which contains the initiation codon of the protein predicted from the 5' and 3' terminal nucleotide sequences obtained by RACE and, as a reverse primer, pE-CtSCPL1-R (5'-GAGGAGAAGCCCGGTTATTATAGAATGGATGCCAAGTTGG-3': SEQ ID NO: 45) which contains the termination codon of the above protein. With the single strand cDNA as a template, PCR was performed in a 50 µl reaction solution using each 20 pmole of pE-CtSCPL1-F and pE-CtSCPL1-R and LATaq polymerase according to the method recommended by the polymerase manufacturer. Thermal conditions of the PCR reaction were as follows: 95° C. for 3 min, then 30 cycles of 95° C. for 30 sec, 55° C. for 45 sec and 72° C. for 80 sec, and finally 72° C. for 7 min. The resultant reaction products were fractionated by agarose gel electrophoresis and the bands of amplified products were cut out. Purified PCR products were subcloned into pET30 Ek/LIC (Novagen). Several pET-CtSCPL1 clones obtained were analyzed to thereby determine the nucleotide sequence of the entire protein-encoding region of CtSCPL1. As a result, it was confirmed that CtSCPL1 includes the entire internal amino acid sequence of the anthocyanin 3'AT protein obtained in Example 6. Further, the 6th cycle amino acid X which was not detected in CTDCPQ-24-T18+19:(R/K)RPLYEXNTM (SEQ ID NOS: 23 and 24) is N according to the amino acid sequence predicted from cDNA and it is believed that this amino acid is modified with sugar chains. The ORF of CtSCPL1 is 1464 bp and encodes a polypeptide consisting of 487 amino acid residues. This has three glycosylation sites and a secretion signal at the N terminal. The nucleotide sequence of CtSCPL1 is shown in SEQ ID NO: 1 and the amino acid sequence deduced therefrom is shown in SEQ ID NO: 2.

(5) Screening of cDNA Library

Approximately 100,000 clones in the butterfly pea petal cDNA library were screened using CtSCPL1, 2, 3 and 4 cDNA fragment clones and *Arabidopsis thaliana* SNG 1 and SNG 2 gene cDNAs as probes. Screening was performed for each probe with final washing conditions of 55° C., 0.1×SSC, 0.1% SDS. Finally, 14 positive clones were obtained. Of these, 13 clones were CtSCPL1 and the remaining one clone was CtSCPL3. The longest clone in the CtSCPL1 positive clones was CtSCPLA1-8 consisting of 1740 bp. When compared to the clone obtained by 5' RACE, CtSCPLA1-8 lacks a sequence upstream of the initiation Met (SEQ ID NO: 46: ATTAAAAAAAAATG). The nucleotide sequence of the open reading frame in the 13 positive clones including CtSCPLA1-8 was identical with the clone obtained by RACE and pET-CtSCPL1.

Example 9

Expression of Recombinant CtSCPL1 Protein in Baculovirus-Insect Cell System (1) Preparation of CtSCPL1 Recombinant Baculovirus For expression of recombinant proteins in Baculovirus-insect cell systems, BaculoDirect Baculovirus Expression Systems (BaculoDirect C-Term Expression Kit; Invitrogen) were used. The protein-encoding region predicted from the nucleotide sequence of the clone obtained in Example 8 was amplified by PCR using a forward primer (CtSCPL1-DTOPO-Fd: 5'-CACCATGGCAGCCTTCAGTTCAACTCATA-3': SEQ ID NO: 47) and a reverse primer (CtSCPL1-Rv-C-Tag: 5'-TAGAATGGATGCCAAGTTGGTGTATG-3': SEQ ID NO: 48). Using the single strand cDNA (1 µl) as a template, 20 pmole each of forward primer and reverse primer, and 2 units of *Pyrobest* Taq polymerase (Takara Bio), PCR was performed in a 50 µl reaction solution according to the method recommended by the manufacturer. Thermal conditions of the PCR reaction were as follows: 94° C. for 3 min. then 30 cycles of 94° C. for 30 sec, 65° C. for 45 sec and 72° C. for 80 sec, and finally 72° C. for 7 min. The resultant PCR product was subcloned into pENTR-D-TOPO vector (Invitrogen) according to the method recommended by the manufacturer. Resultant several pENTR-CtSCPL1 clones were analyzed to thereby confirm the nucleotide sequences thereof Using LR Clonase (Invitrogen), CtSCPL1 was recombined from pENTR-CtSCPL1 into BaculoDirect C-Term Linear DNA. The LR reaction product was transfected into *Spodoptera frugiperda* ovary cell-derived Sf9 cells using Cellfection. Removal of non-recombinant virus using ganciclovir, growth of recombinant virus and measurement of viral titer were performed according to the methods recommended by the manufacturer to thereby prepare 2-3×10⁷pfu/ml of recombinant CtSCPL1 virus.

(2) Expression of Recombinant CtSCPL1 Protein and Confirmation of Enzyme Activity Sf9 cells monolayer-cultured in complete Grace medium or Sf900II-SFM serum free medium (Gibco) in 6-well plates (3×10⁶ cells) were infected with the recombinant virus at a multiplicity of infection (MOI) of 5-10. After a five-day culture at 28° C., the culture broth and the Sf9 cells were recovered. The culture broth was concentrated by centrifugation. The cells were suspended in a buffer and sonicated. The resultant centrifugal supernatant was concentrated by centrifugation in the same manner as applied to the culture broth. Enzyme reaction was performed using the thus concentrated protein solution, and the reaction product was analyzed by HPLC and LC-MS.

When this protein was reacted with preternatin C5 or delphinidin 3-(6-malonyl)glucoside-3'-glucoside and 1-$O$-feruloyl-β-D-glucose as substrates, a reaction product was obtained which had a molecular mass indicating that one feruloyl group was attached to preternatin C5. Thus, 3'AT activity was confirmed. Further, when the protein was reacted ternatin C5 and 1-$O$-p-coumaroyl-β-D-glucose as substrates, 3'AT activity was also recognized. Thus, it was confirmed that CtSCPL1 cDNA is encoding a protein which has an enzyme activity of transferring an acyl group to a glucosyl group in the B ring of anthocyanin using 1-$O$-acyl-β-D-glucose as an acyl donor. No difference caused by different media was observed in activity. No activity was recognized in the recombinant virus-uninfected Sf9 cell extract solution or culture broth. Further, since the enzyme activity was recognized in both the Sf9 cell extract solution and the culture broth, this enzyme was found to be a secretory protein.

Example 10

Preparation of CtSCPL4 Recombinant Baculovirus

The protein-coding region (open reading frame) predicted from the nucleotide sequence of the clone obtained in Example 8 was amplified by PCR using a forward primer (CtSCPL4-DTOPO-Fd: 5'-CACCATGGCGAGGTTTAGT-TCAAGTCTTG-3': SEQ ID NO: 49) and a reverse primer (CtSCPL4-Rv-Stop: 5'-TTACAAAGGCCTTTTAGATATC-CATCTCC-3'SEQ ID NO: 50). PCR was performed in the same manner as in Example 9, and the resultant PCR product was subcloned into pENTR-D-TOPO vector according to the method recommended by the manufacturer. Resultant several pENTR-CtSCPL4 clones were analyzed to thereby confirm the entire nucleotide sequence of CtSCPL4. The nucleotide sequence in the ORF of CtSCPL4 is shown SEQ ID NO: 3 and the amino acid sequence deduced therefrom is shown in SEQ ID NO: 4. The ORF of CtSCPL4 is 1410 bp and encodes a polypeptide consisting of 469 amino acid residues. This has three sugar chain modification sites and a secretion signal at the N terminal. CtSCPL4 has 79.1% homology to CtSCPL1 at the amino acid level and is located most adjacent to CtSCPL1 in SCPL-AT crade in molecular phylogenic analysis. Therefore, it is possible to say that, like CtSCPL1, CtSCPL4 is also encoding a protein which has an enzyme activity of transferring an acyl group especially to a glucosyl group in the B ring of anthocyanin using 1-$O$-acyl-β-D-glucose as an acyl donor. CtSCPL4 was recombined from pENTR-CtSCPL4 into BaculoDirect Secreted Linear DNA using BaculoDirect Baculovirus Expression Systems, and recombinant CtSCPL4 virus was prepared according to the method recommended by the manufacturer.

Example 11

Cloning of Gentian SCPL-AT cDNA (1) Amplification and Cloning of cDNA Fragment Using Degenerate RT-PCR Gentian petals were divided into two stages, i.e., flower bud length 2.5 mm or less and flower bud length 2.5-3.5 mm. Total RNA was prepared from 1.5 g of petals of each stage using TRIzol (Invitrogen). Using 5 μg of the thus obtained total RNA as a template, a single strand cDNA was synthesized with 1st strand cDNA synthesis kit (Amersham Bioscience) according to the method recommended by the manufacturer. The synthesized cDNAs from both stages were mixed in equal amounts to thereby prepare a template for PCR. For PCR reaction, the CODEHOP primers, degenerate primers and NotI-d(T)₁₈ primer described in Example 6 were used. Briefly, using 2 μl of the single strand cDNA as a template and 2 μl each of forward primer and reverse primer and 1 unit of LATaq polymerase, PCR reaction was performed in a 50 μl reaction solution. Thermal conditions of the PCR reaction were as follows: 95° C. for 3 min, then 35 cycles of 95° C. for 30 sec, 48° C. for 45 sec and 72° C. for 80 sec, and finally 72° C. for 7 min. The reaction products obtained from nested PCR using the 1st PCR product as a template were agarose gel electrophoresed. Gel fragments which have those sizes as expected from the primer pairs used were recovered. Purified PCR products were subcloned into pGEM-T Easy vector, followed by determination of nucleotide sequences thereof.

The following primer pairs generated homologous clones to SCPase or SCPL-AT of interest in the following cases: when blockA Fd and blockF Rv, or blockC Fd and blockF Rv were used in the 1st PCR; when blockC Fd and blockF Rv were used in nested PCR using as a template the 1st PCR product obtained using blockA Fd and NotI-d(T)₁₈; when blockC Fd and blockE Rv, or blockC Fd and blockF Rv were used in nested PCR using as a template the 1st PCR product obtained using blockC Fd and NotI-d(T)₁₈. The number of cDNA fragment clones which were believed to encode SCPase or SCPL-AT was 17. As a result of analysis by multiple alignment and with molecular phylogenetic trees, existence of four SCPL clones was confirmed. These gentian SCPL clones were designated GentrSCPL1, 2, 3 and 4, respectively. Among all, cDNA fragment clones GentrSCPL1 and GentrSCPL2 were highly homologous to SCPL-AT and positioned in the same crade as that of known SCPL-AT when molecular phylogenetic trees were created.

(2) RACE of GentrSCPL1 and GentrSCPL2 cDNA Fragments

Poly(A)⁺RNA was purified from the total RNA (total 550 μg) prepared from each stage in (1) in Example 11, using Oligotex-dT30 super according to the method recommended by the manufacturer. From approx. 210 ng of the purified poly(A)⁺RNA, GRR cDNA was synthesized using GeneRacer kit according to the method recommended by the manufacturer. The synthesized GRR cDNA was diluted at 1:3 to prepare a cDNA solution. Using this cDNA solution as a template, PCR was performed with GeneRacer 5' primer and a reverse primer specific to an internal sequence of GentrSCPL1 cDNA fragment (GentrSCPL1-R1 primer: 5'-GCAT-AAACCGTTGCTTTGATCCGCC-3': SEQ ID NO: 51 or GentrSCPL1-R2 primer: 5'-CATCAATGAAGCCATCAGC-CACAGG-3': SEQ ID NO: 52). Further, PCR was performed with GeneRacer 5' primer and a reverse primer specific to an internal sequence of GentrSCPL2 cDNA fragment (GentrSCPL2-R1 primer: 5'-TTAAGCACGTCAGGAATCCGGAGG-3': SEQ ID NO: 53 or GentrSCPL2-R2 primer: 5'-TGAACGTCGAATGCCGTGAAACACC-3': SEQ ID NO: 54). Briefly, using GGR cDNA (as a template), GeneRacer 5' primer (30 pmole), a reverse primer (20 pmole) and LATaq polymerase, PCR was performed in a 50 µl reaction solution according to the method recommended by the polymerase manufacturer. Thermal conditions of the PCR reaction were as follows: 94° C. for 3 min, then 30 cycles of 94° C. for 30 sec, 65° C. for 45 sec and 72° C. for 80 sec, and finally 72° C. for 7 min. Further, nested PCR was performed using the 1st PCR product as a template and GeneRacer 5' nested primer in combination with a reverse primer. The 1st PCR and nested PCR products were fractionated by agarose gel electrophoresis. The bands of amplified products were cut out to thereby recover PCR products. The PCR products purified from gel were subjected to TA cloning. Resultant several clones were analyzed to thereby determine the 5' terminal nucleotide sequences of GentrSCPL1 and GentrSCPL2 cDNA fragments, respectively.

Using a 1:3 dilution of the synthesized GRR cDNA as a template, PCR was performed with GeneRacer 3' primer or GeneRacer 3' nested primer as a reverse primer and GentrSCPL1-F1 primer (5'-TGGCATACAGTGGCGACCATGATC-3': SEQ ID NO: 55) or GentrSCPL1-F2 primer (5'-CTGATGAGTGGCGTCCATGGAAAG-3': SEQ ID NO: 56) each of which is specific to an internal sequence of GentrSCPL1 cDNA fragment, as a forward primer. Further, PCR was performed using as a forward primer GentrSCPL2-F1 primer (5'-CGTTGTAACCGTTCGTTGCCATTCG-3': SEQ ID NO: 57) or GentrSCPL2-F2 primer (5'-CGATGGTGCCATTCATGGCTACTC-3': SEQ ID NO: 58) each of which is specific to an internal sequence of GentrSCPL2 cDNA fragment. PCR, cloning and sequencing were performed in the same manner as in 5'RACE to thereby determine the 3' terminal nucleotide sequences of GentrSCPL1 and GentrSCPL2 cDNA fragments, respectively.

(3) Cloning of Entire Protein-Encoding Region in GentrSCPL1 and GentrSCPL2 cDNA Fragments The inventors synthesized forward primers containing the initiation codon of the protein predicted from the 5' and 3' terminal nucleotide sequences obtained by RACE (Gentr1-DTOPO-F: 5'-CACCATGGCGGTGCCGGCGGTGCC-3': SEQ ID NO: 59 and Gentr2-DTOPO-F: 5'-CACCATGGCGGATACAAACGGCACAGCC-3': SEQ ID NO: 60) and reverse primers containing the predicted termination codon (Gentr1-Rv-CTag: 5'-CAATGGAGAATCCGAGAAAAACCG-3': SEQ ID NO: 61, Gentr1-Rv-Stop: 5'-TTACAATGGAGAATCCGAGAAAAACCG-3': SEQ ID NO: 62, Gentr2-Rv-CTag: 5'-CAACGGTTTATGAGTTATCCACC-3': SEQ ID NO: 63 and Gentr2-Rv-Stop: 5'-CTACAACGGTTTATGAGTTATCCAC-3': SEQ ID NO: 64). Using 1 µl of the single strand cDNA as a template, 20 pmole each of a forward primer and a reverse primer, and 2 units of *Pyrobest* Taq polymerase, PCR was performed in a 50 µl reaction solution according to the method recommended by the polymerase manufacturer. Thermal conditions of the PCR reaction were as follows: 94° C. for 3 min, then 30 cycles of 94° C. for 30 sec, 65° C. for 45 sec and 72° C. for 80 sec, and finally 72° C. for 7 min. The PCR products were subcloned into pENTR-D-TOPO vector according to the method recommended by the manufacturer. Resultant several pENTR-GentrSCPL1 and pENTR-GentrSCPL2 clones were analyzed to confirm nucleotide sequences thereof. Two ORFs were confirmed in GentrSCPL2 and designated GentrSCPL2-1 and GentrSCPL2-2, respectively The nucleotide sequences in the ORFs in GentrSCPL1, GentrSCPL2-1 and GentrSCPL2-2 are shown in SEQ ID NOS: 5, 7 and 9, respectively. The amino acid sequences deduced therefrom are shown in SEQ ID NOS: 6, 8 and 10. The sizes of ORFs in GentrSCPL1, GentrSCPL2-1 and GentrSCPL2-2 were 1446 bp, 1485 bp and 1455 bp, respectively. They were encoding polypeptides consisting of 481, 494 and 484 amino acid residues, respectively. A secretion signal sequence was present in the N-terminal in GentrSCPL1, GentrSCPL2-1 and GentrSCPL2-2. They had 2, 3 and 3 glycosylation sites, respectively, in their active protein coding region. It was found that GentrSCPL2-2 is a clone where amino acids from position 226 to 235 of GentrSCPL2-1 are missing. GentrSCPL2-1 and GentrSCPL2-2 have 41% homology to CtSCPL1 at the amino acid level. It was also found in the molecular phylogenic analysis that they are positioned adjacent to CtSCPL1, next to CtSCPL4, in SCPL-AT crade. Therefore, it is possible to describe that, like CtSCPL1, GentrSCPL2-1 and GentrSCPL2-2 are encoding a protein which has an enzyme activity of transferring an acyl group especially to a glucosyl group in the B ring of anthocyanin using 1-$O$-acyl-$\beta$-D-glucose as an acyl donor. GentrSCPL1 is also positioned in the SCPL-AT grade and has 32% homology to GentrSCPL2 at the amino acid level. Thus, it is possible to describe that GentrSCPL1 is encoding an acyltransferase which uses 1-$O$-acyl-$\beta$-D-glucose as an acyl donor. GentrSCPL1 and GentrSCPL2-1 were recombined from pENTR-GentrSCPL1 and pENTR-GentrSCPL2-1 into BaculoDirect C-Tag Linear DNA and BaculoDirect Secreted Linear DNA using BaculoDirect Baculovirus Expression Systems, followed by preparation of recombinant GentrSCPL1 virus and recombinant GentrSCPL2-1 virus according to the method recommended by the manufacturer.

Example 12

Cloning of Lobelia SCPL-AT cDNA (1) Amplification of cDNA Fragment by Degenerate PCR and Cloning Poly(A)$^+$RNA was prepared from petals of lobelia (Lobelia erinus cv. Riviera Midnight Blue) using QuickPrep Micro mRNA Purification Kit (Amersham Bioscience) according to the method recommended by the manufacturer. Using the resultant poly(A)$^+$RNA as a template, single strand cDNA was synthesized with 1st strand cDNA synthesis kit according to the method recommended by the manufacturer. For the PCR reaction, the CODEHOP primers, degenerate primers and NotI-d(T)$_{18}$ primer described in Example 6 were used. Briefly, using 2 µl of the single strand cDNA as a template, 2 µl each of a forward primer and a reverse primer, and 1 unit of ExTaq polymerase, PCR was performed in a 50 µl reaction solution. Thermal conditions of the PCR reaction were as follows: 95° C. for 3 min, then 30 cycles of 95° C. for 30 sec, 50° C. for 45 sec and 72° C. for 90 sec, and finally 72° C. for 7 min. PCR products obtained by nested PCR using 1st PCR products as templates were agarose gel electrophoresed. Gel fragments with those sizes as expected from individual primer pairs used were recovered. Purified PCR products were subcloned into pGEM-T Easy vector to thereby determine nucleotide sequences thereof.

The following primer pairs generated homologous clones to SCPase or SCPL-AT of interest in the following cases: when blockA Fd and blockF Rv, blockC Fd and blockF Rv, or blockC Fd and NotI-d(T)$_{18}$ were used in the 1st PCR, and when blockA Fd and blockF Rv, blockB Fd and blockE Rv, blockC Fd and blockE Rv, or blockC Fd and blockF Rv were used in nested PCR. The number of cDNA fragment clones which were believed to encode SCPase or SCPL-AT was 21. Among those clones, existence of LeSCPL1 (a SCPL-AT clone positioned in the same crade as that of known SCPL-AT) was confirmed.

(2) RACE of LeSCPL1 cDNA

Total RNA was prepared from 5 g of lobelia petals (2 g of flowered petals and 3 g of flower bud petals) by a modified CTAB method. From the resultant total RNA, poly(A)$^+$RNA was purified using Oligotex-dT30 super according to the method recommended by the manufacturer. GRR cDNA was synthesized from approx. 480 ng of the purified poly(A)$^+$ RNA using GeneRacer kit according to the method recommended by the manufacturer.

The synthesized GRR cDNA was diluted at 1:3 to prepare a cDNA solution. Using this cDNA solution as a template, PCR was performed with GeneRacer 5' primer and a reverse primer specific to an internal sequence of LeSCPL1 cDNA fragment (LeSCPL1-R1 primer: 5'-AATGGGTTGCCTAG-CACGTATCCC-3': SEQ ID NO: 65 or LeSCPL1-R2 primer: 5'-GATTCGTGTTTGGCATCTGTCCAGC-3': SEQ ID NO: 66). Briefly, using the GRR cDNA as a template, 30 pmole of GeneRacer 5' primer, 20 pmole of a reverse primer, and LATaq polymerase, PCR was performed in a 50 µl reaction solution. Thermal conditions of the PCR reaction were as follows: 94° C. for 3 min, then 30 cycles of 94° C. for 30 sec, 65° C. for 45 sec and 72° C. for 80 sec, and finally 72° C. for 7 min. Further, using the 1st PCR product as a template, nested PCR was performed with a combination of GeneRacer 5' nested primer and a reverse primer. The 1st PCR and nested PCR products were fractionated by agarose gel electrophoresis, and the bands of amplified products were cut out to thereby recover the PCR products. The PCR products purified from gel were TA-cloned. Resultant several clones were analyzed to determine the 5' terminal nucleotide sequence of the LeSCPL1.

Using a 1:3 dilution of the synthesized GRR cDNA as a template, PCR was performed with GeneRacer 3' primer or GeneRacer 3' nested primer as a reverse primer and LeSCPL1-F1 primer (5'-AACGAGCCAGTTGTCCAA-CAAGCC-3': SEQ ID NO: 67) or LeSCPL1-F2 primer (5'-CTCCACGTACGAAAGGGAACACTAAC-3': SEQ ID NO: 68), each of which is specific to an internal sequence of LeSCPL1 cDNA fragment, as a forward primer. PCR, cloning and sequencing were performed in the same manner as in 5'RACE to thereby determine the 3' terminal nucleotide sequence of LeSCPL1 cDNA.

(3) Cloning of the Entire Protein-Encoding Region in LeSCPL1 cDNA

The inventors synthesized a forward primer which contains the initiation codon of the protein predicted from the 5' and 3' terminal nucleotide sequences obtained by RACE (LeSCPL-DTOPO-F: 5'-CACCATGGCGTTTGGTATGC-CATTTTCG-3': SEQ ID NO: 69) and reverse primers which contain the termination codon of the above protein (LeSCPL-Rv-CTag: 5'-CAATAAACTACGAGTAAGCCACCTTC-3': SEQ ID NO: 70 and LeSCPL-Rv-Stop: 5'-TCA-CAATAAACTACGAGTAAGCCAC-3': SEQ ID NO: 71). Using 1 µl of the single strand cDNA as a template, 20 pmole each of a forward primer and a reverse primer, and 2 units of *Pyrobest* Taq polymerase (Takara Bio), PCR was performed in a 50 µl reaction solution according to the method recommended by the manufacturer. The resultant PCR products were subcloned into pENTR-D-TOPO vector according to the method recommended by the manufacturer. Resultant several pENTR-LeSCPL1 clones were analyzed to confirm the nucleotide sequences thereof. The nucleotide sequence of the ORF of LeSCPL1 is shown in SEQ ID NO: 11, and the amino acid sequence deduced therefrom is shown in SEQ ID NO: 12. The ORF of LeSCPL1 is 1466 bp, encoding a polypeptide consisting of 481 amino acid residues. It contains 3 glycosylation sites. LeSCPL1 has 26% homology to CtSCPL1 at the amino acid level and is positioned in the SCPL-AT crade in molecular phylogenic analysis. Therefore, it is possible to describe that LeSCPL1 is encoding an acyltransferase which uses 1-*O*-acyl-p-D-glucose as an acyl donor. LeSCPL1 was recombined from pENTR-LeSCPL1 into BaculoDirect C-Tag Linear DNA and BaculoDirect Secreted Linear DNA using BaculoDirect Baculovirus Expression Systems. Then, recombinant virus was prepared according to the method recommended by the manufacturer.

Example 13

Cloning of 1-*O*-Acyl-β-D-Glucose Synthase (UDP-Glucose:Hydroxycinnamate 1O-Glucosyltransferase) cDNA (1) Isolation of Butterfly Pea 1-*O*-Acyl-β-D-Glucose Synthase cDNA A degenerate primer GT-SPF (5'-WCICAYTGYGGITG-GAAYTC-3': SEQ ID NO: 72) was synthesized based on the amino acid sequence of PSPG-box (Huges and Huges (1994) DNA Seq., 5: 41-49), a region highly conserved in plant secondary metabolite glucosyltransferases. Using single strand cDNA as a template, 100 pmole of Gt-SPF primer, 14 pmole of NotI-d(T)$_{18}$ primer and 1 unit of ExTaq polymerase, PCR was performed in a 50 µl reaction solution. Thermal conditions of the PCR reaction were as follows: 94° C. for 5 min, then 38 cycles of 94° C. for 30 sec, 42° C. for 30 sec and 72° C. for 60 sec, and finally 72° C. for 10 min. The resultant PCR product was subcloned into pGEM-T easy vector according to the method recommended by the manufacturer. Several resultant clones were analyzed to confirm the nucleotide sequences thereof. As a result, a cDNA fragment clone GTC600-11 was obtained which shows high homology to UDP-glucose:hydroxycinnamate 1-*O*-glucosyltransferase (NCBI/EMBL/DDBJ Accession No. AF287143; PIR Accession Nos. D71419, E71419 and F71419) found in plants such as *Brassica napus* and *Arabidopsis thaliana*. Using this cDNA fragment as a probe, 250,000 clones in butterfly pea petal cDNA library were screened with washing conditions of 2×SSC, 1% SDS and 60° C. Finally, 7 clones were obtained in which the size of insert subcloned into pBluescript SK- is 1.5 kbp or more. The predicted amino acid sequences encoded by the ORFs of these clones were found identical; the longest clone containing the initiation codon was designated CtGT11-4. The screening of the library was performed by known methods (see, for example, Japanese Unexamined Patent Publication No. 2005-95005). CtGT11-4 gene was 1788 bp, encoding a polypeptide consisting of 473 amino acid residues. The nucleotide sequence of this gene is shown in SEQ ID NO: 13, and the deduced amino acid sequence therefrom is shown in SEQ ID NO: 14.

(2) Confirmation of 1-*O*-Acyl-β-D-Glucose Synthase Activity in CtGT11-4 Gene Product For expressing CtGT11-4 gene, pET30Ek/LIC System was used. First, PCR was performed using the following primers for amplifying the ORF cDNA of CtGT11-4: pEGTC11-4F (5'-GACGACGACAAGATGGGGTCTGAAGCT-TCGTTTC-3': SEQ ID NO: 73) and pETGTC11-4R (5'-GAGGAGAAGCCCGGTCTAAGGGTTACCACGGTTTC-3': SEQ ID NO: 74). Briefly, using the plasmid obtained in (1) in Example 12 as a template, 40 pmole each of pEGTC11-4F and pETGTC 11-4R, and 1 unit of ExTaq polymerase, PCR was performed in a 50 μl reaction solution according to the method recommended by the manufacturer. The resultant PCR product was subcloned into pET30Ek/LIC vector according to the method recommended by the manufacturer. Resultant several clones were analyzed to confirm the nucleotide sequences thereof, followed by transformation into *Escherichia coli* BL21-CodonPlus(DE3)-RP (Stratagene).

The transformed *E. coli* was shaking-cultured overnight in 3 ml of LB medium containing 50 μg/ml kanamycin and 34 μg/ml chloramphenicol. This culture broth (500 μl) was inoculated into LB medium (50 ml) and shaking-cultured until absorbance at 600 nm reached 0.4. Then, isopropyl-β-D-thiogalactoside (IPTG) was added to give a final concentration of 0.4 mM. The cells were shaking-cultured at 25° C. for 16 hr and then harvested by refrigerated centrifugation (8000 rpm, 4° C., 20 min). CtGT11-4 protein was partially purified from the cells using Ni-NTA mini-column according to the method recommended by the manufacturer. Subsequently, the resultant protein was subjected to centrifugal concentration with an ultrafilter and used in enzyme activity measurement.

For measuring enzyme activity, a 30 μl reaction solution containing 100 mM potassium phosphate buffer (pH 7.4), 30 pmole of UDP-glucose, 30 pmole of hydroxycinnamic acid and 15 μl of recombinant protein solution was reacted at 30° C. (for 10 min, 20 min or 30 min), followed by termination of the reaction by adding 6 μl of 1 M aqueous HCl solution. As hydroxycinnamic acid, p-coumaric acid, caffeic acid, ferulic acid and sinapic acid were used. The enzyme reaction products were analyzed by reversed-phase high performance liquid chromatography (Shiseido NanoSpace system) using Develosil C30-UG-5 (1.5 i.d.×250 mm). The solvent retained a flow rate of 0.125 ml/min. Using 5% MeCN aqueous solution as liquid A and 0.05 M TFA-containing 40% MeCN aqueous solution as liquid B, a linear gradient was provided in such a manner that the concentration of liquid B became 14% and 86% at 0 min and 20 min from the start of separation, respectively. The eluted materials were detected with a PDA detector, and the resultant data were analyzed to thereby quantitatively determine 1-*O*-acyl-β-D-glucose. 1-*O*-Hydroxycinnamoyl-β-D-glucoses (1-*O*-β-coumaroyl-β-D-glucose: Rt 8.1 min; 1-*O*-caffeoyl-β-D-glucose: Rt 5.7 min; 1-*O*-feruloyl-β-D-glucose: Rt 9.3 min; and 1-*O*-sinapoyl-β-D-glucose: Rt 9.8 min) were detected in the reaction products generated by recombinant CtGT11-4. As the reaction time increased, the amounts of reaction products 1-*O*-hydroxycinnamoyl-β-D-glucoses increased linearly. From these results, it was confirmed that CtGT11-4 gene is encoding an enzyme having UDP-glucose:hydroxycinnamate 1-*O*-glucosyltransferase activity Thus, it has become clear that CtGT11-4 gene is a 1-*O*-acyl-β-D-glucose synthase gene.

(3) Isolation of Lobelia 1-*O*-Acyl-β-D-Glucose Synthase cDNA

According to the method described in (1) in Example 12, degenerate RT-PCR was performed using lobelia petal-derived single strand cDNA as a template. Then, cDNA fragments highly homologous to known genes were cloned. A cDNA library derived from petals of *Lobelia erinus* cv. Riviera Midnight Blue was constructed, and approx. 500,000 clones were screened using a cDNA fragment clone LeGT13 obtained above as a probe. Finally, 28 positive clones were obtained. Predicted amino acid sequences encoded by their ORFs could be classified into two groups. The longest clones in these two groups were designated LeGT13-20 and LeGT13-30, respectively LeGT13-20 and LeGT13-30 were 1574 bp and 1700 bp in size, respectively. They both had an initiation codon; their ORF was 1461 bp encoding a polypeptide consisting of 486 amino acid residues. Since LeGT13-20 and LeGT13-30 showed 95% homology to each other at the amino acid level, it was believed that they are alleles encoding the same enzyme. The nucleotide sequences of LeGT13-20 and LeGT13-30 are shown in SEQ ID NOs: 15 and 17, and the amino acid sequences deduced therefrom are shown in SEQ ID NOs: 16 and 18.

(4) Confirmation of 1-*O*-Acyl-β-D-Glucose Synthase Activity in LeGT13-20 and LeGT 13-30 Gene Products LeGT13-20 and LeGT13-30 genes were expressed using pET30Ek/LIC System (Novagen). PCR was performed using the following primers for amplifying the ORF cDNA of LeGT13-20: pELeGT13A-F (5'-GACGACGACAA-GATGGGCTCACTGCAGGGTACTACTACCGTC-3' (SEQ ID NO: 75) and pELeGT13A-R (5'-GAGGGAGAAGCCCG-GTTAGTGCCCAACAACATCTTTTC-3' (SEQ ID NO: 76). Further, PCR was performed using the following primers for amplifying the ORF cDNA of LeGT13-30: pELeGT13B-F (5'-GACGACGACAAGATGGGCTCACTG-CAGGGTACTACTACCGTT-3' (SEQ ID NO: 77) and pELeGT13B-R (5'-GAGGGAGAAGCCCGGTTAGTGC-CCAATAACACCTTTTT-3' (SEQ ID NO: 78). Briefly, using the plasmid obtained in (3) in Example 12 as a template, 20 pmole of pELeGT13A-F or pELeGT13B-F as a forward primer, 20 pmole of pELeGT13A-R or pELeGT13B-R as a reverse primer, and 1 unit of ExTaq polymerase, PCR was performed in a 50 μl reaction solution according to the method recommended by the polymerase manufacturer. The resultant PCR products were subcloned into pET30Ek/LIC vector according to the method recommended by the manufacturer. Resultant several clones were analyzed to confirm the nucleotide sequences thereof, and then transformed into *E. coli* BL21-CodonPlus(DE3)-RP. Expression of the transferred genes in transformed *E. coli*, partial purification of the recombinant proteins, and analysis of enzyme reaction and reaction products were performed in the same manner as described in (2) in Example 12. As a result, glucosyltransferase activity was confirmed against all of the four types of hydroxycinnamic acid used. From these results, it was confirmed that LeGT13-20 gene and LeGT13-30 gene are encoding an enzyme having UDP-glucose:hydroxycinnamate 1-*O*-glucosyltransferase activity. Thus, it has become clear that both LeGT13-20 gene and LeGT13-30 gene are a 1-*O*-acyl-β-D-glucose synthase gene.

The invention claimed is:

1. An isolated gene encoding a protein having an activity of transferring an aromatic acyl group to a sugar residue of a flavonoid using 1-$O$-acyl-$\beta$-D-glucose as an acyl donor, wherein the gene comprises:
   (a) a nucleotide sequence selected from the group consisting of SEQ ID NOS: 1, 3, 5, 7, 9 and 10;
   (b) a nucleotide sequence encoding an amino acid sequence selected from the group consisting of SEQ ID NOS: 2, 4, 6, 8, 10 and 12; or
   (c) a nucleotide sequence encoding an amino acid sequence having 70% or more homology with any one of SEQ ID NOS: 2, 6, 8, 10 and 12 or an amino acid sequence having at least 79.1% homology with SEQ ID NO:4.

2. A vector comprising the gene according to claim 1.

3. A host cell which has been transformed by the vector according to claim 2.

4. A method of preparing a protein having an activity of transferring an aromatic acyl group to a sugar residue of a flavonoid using 1-$O$-acyl-$\beta$-D-glucose as an acyl donor or a protein having an activity of transferring a glucosyl group to a hydroxyl group at position 1 of hydroxycinnamic acid using UDP-glucose as a glucosyl donor, which comprises culturing or growing the host cell according to claim 3 and recovering said protein from said host cell.

5. A protein encoded by the gene according to claim 1.

6. A method of preparing a protein by in vitro translation using the gene according to claim 1.

7. A plant which has been transformed by introducing thereinto the gene according to claim 1 or a vector comprising the gene according to claim 1 or an offspring of the plant.

8. An offspring of the plant according to claim 7, wherein the offspring expresses the gene.

9. A tissue of the plant or the offspring according to claim 7.

10. A cut flower of the plant or the offspring according to claim 7.

11. A method of transferring an aromatic acyl group to a sugar residue of a flavonoid using 1-$O$-acyl-$\beta$-D-glucose as an acyl donor, which comprises introducing the gene according to claim 1 or a vector comprising the gene according to claim 1 into a plant or plant cell and expressing said gene.

12. A method of modifying the flower color, comprising introducing the gene according to claim 1 or a vector comprising the gene according to claim 1 into a plant or plant cell and expressing said gene.

13. A method of modifying the flower color in a plant having the gene according to claim 1, comprising inhibiting the expression of said gene.

14. An isolated gene encoding a protein having an activity of transferring an aromatic acyl group to a sugar residue of a flavonoid using 1-$O$-acyl-$\beta$-D-glucose as an acyl donor, wherein the gene comprises:
   (a) a nucleotide sequence selected from the group consisting of SEQ ID NOS: 1, 5, 7, 9 and 10;
   (b) a nucleotide sequence encoding an amino acid sequence selected from the group consisting of SEQ ID NOS: 2, 6, 8, 10 and 12; or
   (c) a nucleotide sequence encoding an amino acid sequence having 70% or more homology with any one of SEQ ID NOS: 2, 6, 8, 10 and 12.

* * * * *